(12) United States Patent
Bonanomi et al.

(10) Patent No.: US 7,947,683 B2
(45) Date of Patent: May 24, 2011

(54) 3-(1,2,4-TRIAZOL-3-YLALKYL) AZABICYCLO (3.1.0) HEXANE DERIVATIVES AS MODULATORS OF DOPAMINE D3 RECEPTORS

(75) Inventors: Giorgio Bonanomi, Verona (IT); Anna Checchia, Verona (IT); Elettra Fazzolari, Verona (IT); Dieter Hamprecht, Verona (IT); Fabrizio Micheli, Verona (IT); Luca Tarsi, Verona (IT); Silvia Terreni, Verona (IT)

(73) Assignee: Glaxo Group Limted, Greenford, Middlesex (GB)

( * ) Notice: Subject to any disclaimer, the term of this patent is extended or adjusted under 35 U.S.C. 154(b) by 608 days.

(21) Appl. No.: 11/911,027

(22) PCT Filed: Apr. 12, 2006

(86) PCT No.: PCT/EP2006/003554
§ 371 (c)(1),
(2), (4) Date: Oct. 9, 2007

(87) PCT Pub. No.: WO2006/108701
PCT Pub. Date: Oct. 19, 2006

(65) Prior Publication Data
US 2009/0124629 A1  May 14, 2009

(30) Foreign Application Priority Data

Apr. 14, 2005 (GB) .................................. 0507602.1

(51) Int. Cl.
C07D 249/08 (2006.01)
C07D 403/14 (2006.01)
C07D 401/14 (2006.01)
C07D 263/30 (2006.01)
C07D 417/14 (2006.01)
A61K 31/4196 (2006.01)
A61K 31/501 (2006.01)
A61K 31/4439 (2006.01)
A61K 31/426 (2006.01)
A61K 31/4709 (2006.01)
A61P 25/18 (2006.01)

(52) U.S. Cl. ............... 514/252.06; 548/265.8; 548/235; 548/181; 548/266.2; 514/383; 514/339; 514/374; 514/365; 514/314; 544/338; 546/272.4; 546/167

(58) Field of Classification Search .............. 548/266.4, 548/266.6, 265.8, 235, 181, 266.2; 514/383, 514/252.06, 339, 374, 365, 314; 544/338; 546/272.4, 167

See application file for complete search history.

(56) References Cited

U.S. PATENT DOCUMENTS

| | | | |
|---|---|---|---|
| 4,435,419 A | 3/1984 | Epstein et al. | |
| 2007/0142438 A1 | 6/2007 | Arista et al. | 514/341 |
| 2007/0249642 A1 | 10/2007 | Bertani et al. | 514/269 |
| 2008/0058398 A1 | 3/2008 | Anderton et al. | 514/374 |
| 2008/0167357 A1 | 7/2008 | Hamprecht et al. | 514/384 |
| 2008/0176917 A1 | 7/2008 | Andreotti et al. | 514/384 |
| 2008/0227837 A1 | 9/2008 | Arista et al. | 514/384 |
| 2008/0242715 A1 | 10/2008 | Capelli et al. | 514/384 |
| 2009/0030062 A1 | 1/2009 | Gentile et al. | 514/412 |
| 2009/0036461 A1 | 2/2009 | Hamprecht et al. | 514/252.06 |
| 2009/0221593 A1 | 9/2009 | Bonanomi et al. | 514/249 |
| 2009/0221618 A1 | 9/2009 | Arista et al. | 514/274 |
| 2009/0326011 A1* | 12/2009 | Arista et al. | 514/339 |
| 2010/0004224 A1* | 1/2010 | Jagerovic et al. | 514/217.09 |

FOREIGN PATENT DOCUMENTS

| WO | WO 95/15327 A | 6/1995 |
|---|---|---|
| WO | WO 00/42036 A | 7/2000 |
| WO | WO 02/40471 A | 5/2002 |
| WO | WO 2005/080382 A | 9/2005 |

OTHER PUBLICATIONS

U.S. Appl. No. 11/917,352, filed Jun. 13, 2006, Arista, et al.
U.S. Appl. No. 12/295,024, filed Mar. 30, 2007, Bertani, et al.
U.S. Appl. No. 12/295,304, filed Mar. 30, 2007, Bertani, et al.

* cited by examiner

*Primary Examiner* — James O Wilson
*Assistant Examiner* — Cecilia M Jaisle
(74) *Attorney, Agent, or Firm* — Bonnie L. Deppenbrock

(57) ABSTRACT

The present invention relates to novel compounds of formula (I) or pharmaceutically acceptable salt thereof:

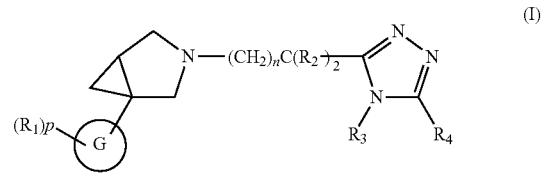

processes for their preparation, intermediates used in these processes, pharmaceutical compositions containing them and their use in therapy, as modulators of dopamine $D_3$ receptors, e.g. to treat drug dependency, as antipsychotic agents, to treat obsessive compulsive spectrum disorders, premature ejaculation or cognition impairment.

10 Claims, No Drawings

3-(1,2,4-TRIAZOL-3-YLALKYL) AZABICYCLO (3.1.0) HEXANE DERIVATIVES AS MODULATORS OF DOPAMINE D3 RECEPTORS

This application is a 35 U.S.C. 371 application of International Application No. PCT/EP2006/003554, filed 12 Apr. 2006, and which claims the benefit of Provisional Application No. GB0507602.1, filed 14 Apr. 2005.

The present invention relates to novel compounds, processes for their preparation, intermediates used in these processes, pharmaceutical compositions containing them and their use in therapy, as modulators of dopamine $D_3$ receptors.

WO 2002/40471 (SmithKline Beecham) discloses certain benzazepine compounds having activity at the dopamine $D_3$ receptor.

Recently a patent application has been published as WO2005/080382 discloses the following compounds:

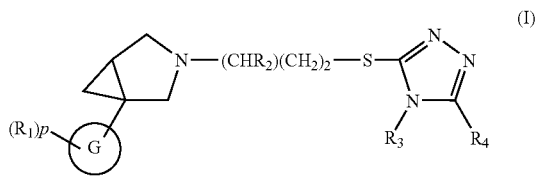

None of the above references disclosed compounds falling into the scope of the present invention.

A new class of compounds which have affinity for dopamine receptors, in particular the dopamine $D_3$ receptor has been found. These compounds have potential in the treatment of conditions wherein modulation of the $D_3$ receptor is beneficial, e.g. to treat drug dependency or as antipsychotic agents.

The present invention provides a compound of formula (I) or a pharmaceutically acceptable salt thereof:

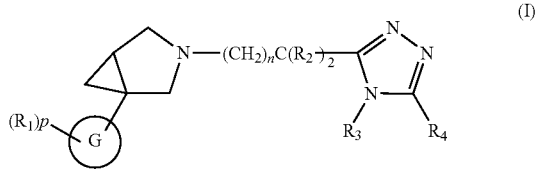

wherein

G is selected from a group consisting of: phenyl, pyridyl, benzothiazolyl and indazolyl;

p is an integer ranging from 0 to 5;

$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alakanoyl and $SF_5$; or corresponds to a group $R_5$;

each $R_2$ is independently hydrogen, fluorine or $C_{1-4}$alkyl;

n is 2, 3, 4, or 5;

$R_3$ is $C_{1-4}$alkyl;

$R_4$ is hydrogen, or a $C_{1-4}$alkyl group, a benzyl group, a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or $R_4$ is a $-SR_6$ group;

$R_5$ is selected from a group consisting of: isoxazolyl, $-CH_2-$N-pyrrolyl, 1,1-dioxido-2-isothiazolidinyl, thienyl, thiazolyl, pyridyl and 2-pyrrolidinonyl, and such a group is optionally substituted by one or two substituents selected from a group consisting of: halogen, cyano, $C_{1-4}$alkyl, halo$C_{1-4}$alkyl, $C_{1-4}$alkoxy and $C_{1-4}$alkanoyl;

$R_6$ is $C_{1-4}$alkyl or $-CH_2C_{3-4}$cycloalkyl;

and when $R_1$ is chlorine and p is 1, such $R_1$ is not present in the ortho position with respect to the linking bond to the rest of the molecule; and when $R_1$ corresponds to $R_5$, p is 1.

Because of the presence of the fused cyclopropane compounds of formula (I) are believed to have a "cis" disposition of the substituents (both groups linked to the bicyclic ring system are on the same face of this bicyclic ring system).

In another embodiment of the present invention compounds of formula (I)' are provided which correspond to the compounds of formula (I) having "cis" disposition, represented by the bold highlight of the bonds

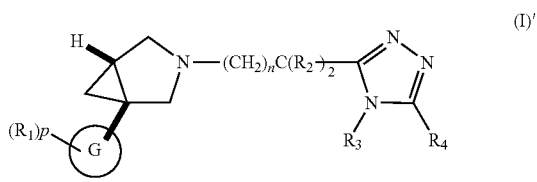

wherein G, p, $R_1$, $R_2$, $R_3$, $R_4$, and $R_5$ are defined as above for compounds of formula (I).

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds means the "cis" configuration):

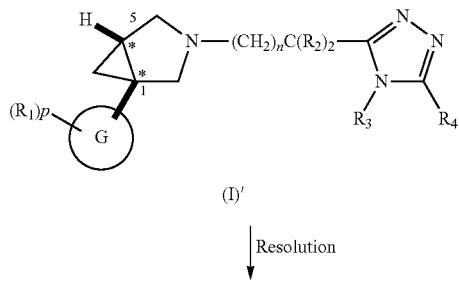

-continued

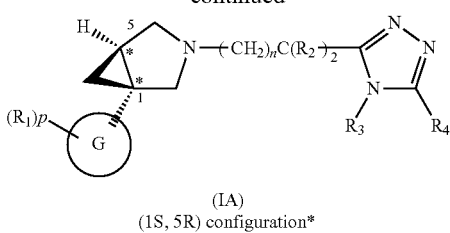

(IA)
(1S, 5R) configuration*

*when G is a 2-pyridyl derivative the configuration becomes (1R, 5R) due to different Cahn-Ingold-Prelog nomenclature priorities In a further embodiment of the present invention compounds of formula (IA) or a pharmaceutically acceptable salt thereof are provided that correspond to stereochemical isomers of compounds of formula (I)', enriched in configuration (1S,5R) (or (1R,5R) when G is 2-pyridyl):

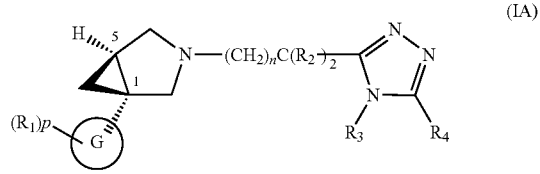

(IA)

wherein G, p, $R_1$, $R_2$, $R_3$, $R_4$, and $R_5$ are defined as above for compounds of formula (I)'.

It is intended in the context of the present invention that stereochemical isomers enriched in configuration (1S,5R) or (1R,5R) of formula (IA) correspond in one embodiment to at least 90% e.e. In another embodiment the isomers correspond to at least 95% e.e. In another embodiment the isomers correspond to at least 99% e.e.

The term "5- or 6-membered heteroaromatic group" refers to a monocyclic 5- or 6-membered heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term '$C_{1-4}$ alkanoyl group' as used herein may be a linear or a branched chain alkanoyl group, for example acetyl, ethylcarbonyl, n-propylcarbonyl, i-propyl carbonyl, n-butylcarbonyl or t-butylcarbonyl and the like.

The term '$C_{3-4}$ cycloalkyl group' as used herein means a non aromatic monocyclic hydrocarbon ring of 3 to 4 carbon atom such as, for example, cyclopropyl, cyclobutyl.

The term '$C_{1-4}$ alkoxy group' as used herein may be a linear or a branched chain alkoxy group, for example methoxy, ethoxy, propoxy, prop-2-oxy, butoxy, but-2-oxy or methylprop-2-oxy and the like.

The term 'halo $C_{1-4}$ alkyl' as used herein means an alkyl group having one or more carbon atoms and wherein at least one hydrogen atom is replaced with halogen such as for example a trifluoromethyl group and the like.

The term 'halo $C_{1-4}$ alkoxy group' as used herein may be a $C_{1-4}$ alkoxy group as defined before substituted with at least one halogen, preferably fluorine, such as $OCHF_2$, or $OCF_3$.

The term "$SF_5$" refers to pentafluorosulfanyl.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "8- to 11-membered bicyclic group" refers to a bicyclic ring system containing a total of 8, 9, 10 or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl. Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "heterocyclyl" refers to a 5 or 6-membered monocyclic or 8 to 11-membered bicyclic group wherein 1, 2, 3, 4 or 5 of the carbon atoms are replaced by a heteroatom independently selected from O, S and N and which is partially or fully saturated. Examples of "heterocyclyl" which are fully saturated 5 or 6-membered monocyclic rings include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "heterocyclyl" groups which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl. Examples of "heterocyclyl" groups which are fully saturated 8 to 11-membered bicyclic rings include decahydroquinolinyl, octahydro-2H-1,4-benzoxazinyl and octahydro-1H-cyclopenta-[b]pyridinyl. Examples of "heterocyclyl" groups which are partially saturated 8 to 11-membered bicyclic rings include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Pharmaceutically acceptable salts are particularly suitable for medical applications because of their greater aqueous solubility relative to the parent compounds. Such salts must clearly have a pharmaceutically acceptable anion or cation. Suitably pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic(pamoic), methanesulfonic, ethanesulfonic, pantothenic, stearic, sulfinylic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine(N-methylglucamine), lysine and procaine; and internally formed salts. Salts having a non-pharmaceutically acceptable anion or cation are within the scope of the invention as useful intermediates for the preparation of pharmaceutically acceptable salts and/or for use in non-therapeutic, for example, in vitro, situations.

In one embodiment, G is phenyl or pyridyl.

In one embodiment, p is 1 or 2.

In another embodiment, p is 0.

In one embodiment, $R_1$ is halogen, cyano, acetyl, trifluoromethyl or trifluoromethoxy.

When $R_1$ is chlorine and p is 1, such $R_1$ is not present in the ortho position with respect to the linking bond to the rest of the molecule. In one embodiment, when $R_1$ is $SF_5$ and p is 1, the $SF_5$ group is not present in the ortho position with respect to the linking bond to the rest of the molecule.

Suitably, $R_1$ is bromo, fluoro, trifluoromethoxy, cyano, hydroxy, chloro, methoxy, tert-butyl or trifluoromethyl.

In one embodiment, each $R_2$ is hydrogen.

In one embodiment, n is 3 or 4.

In one embodiment, a compound of formula (IB) or a pharmaceutically acceptable salt thereof is provided, wherein $R_1$, $R_2$, $R_3$, $R_4$, p and n are as defined for formula (I):

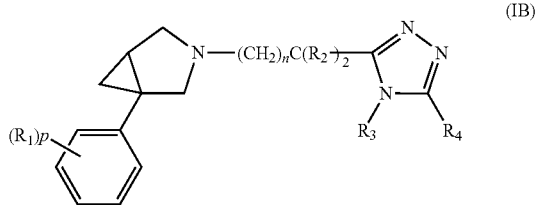

(IB)

In Formula (IB), in one embodiment, $R_3$ is methyl; $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.

In one embodiment, n is 3 or 4.

In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In Formula (IB), in a further embodiment, $R_3$ is methyl; $R_4$ may be a $C_{1-4}$alkyl group, a benzyl group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$, or a group —$SR_6$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.

In one embodiment, n is 3 or 4.

In one embodiment, $R_1$ is halogen or trifluoromethyl.

Examples of $R_4$ include an an optionally substituted benzyl group, an optionally substituted alkyl group (i.e. t-butyl), a thioalkyl group (i.e. thiomethylcyclopropyl, thiomethyl).

In Formula (IB), in a still further embodiment, $R_3$ is methyl; both $R_2$ are at the same time methyl or fluorine.

In Formula (IB), in another embodiment, both $R_2$ are at the same time methyl or fluorine; $R_3$ is methyl; $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.

In one embodiment, n is 3 or 4.

In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In another embodiment, a compound of formula (IC) or a pharmaceutically acceptable salt thereof is provided, wherein $R_1$, p, n, $R_3$ and $R_4$ are as defined for formula (I):

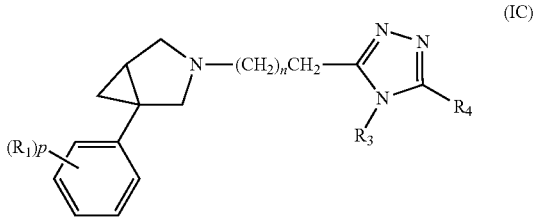

(IC)

In Formula (IC), in one embodiment, $R_3$ is methyl; $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.

In one embodiment, n is 3 or 4.

In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazoly! (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In Formula (IC), in another embodiment, $R_3$ is methyl; $R_4$ may be a $C_{1-4}$alkyl group, a benzyl group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$, or a group —$SR_6$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.

In one embodiment, n is 3 or 4.

In one embodiment, $R_1$ is halogen or trifluoromethyl.

Examples of $R_4$ include an optionally substituted benzyl group, an optionally substituted alkyl group (i.e. t-butyl), a thioalkyl group (i.e. thiomethylcyclopropyl, thiomethyl).

In another embodiment, a compound of formula (ID) or a pharmaceutically acceptable salt thereof is provided, wherein G is 2-pyridyl or 3-pyridyl and $R_1$, p, n, $R_3$ and $R_4$ are as defined for formula (I):

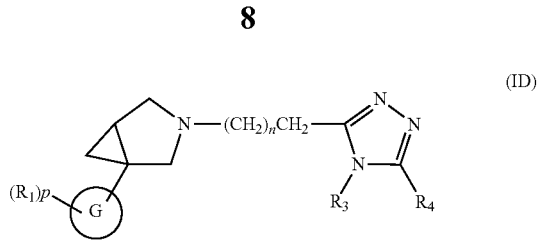

In Formula (ID), in one embodiment, G corresponds to 2-pyridyl (Compounds (ID1)) and in another embodiment to 3-pyridyl (Compounds (ID2)), as illustrated below:

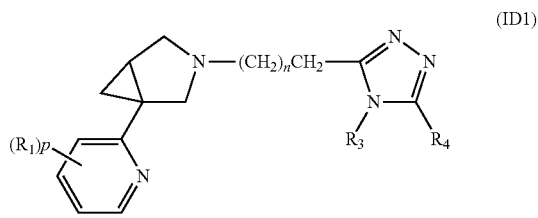

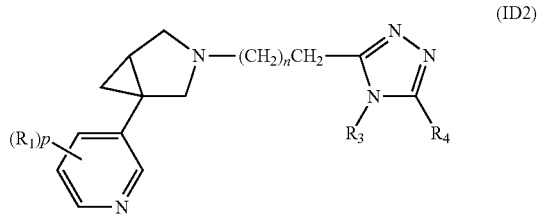

In Formulae (ID), (ID1) and (ID2), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.

In one embodiment, n is 3 or 4.

In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

The strategy for determining the absolute configuration of the compounds of the present invention comprised as a first step the preparation of the chiral intermediate, (1S,5R)-1-[4-(trifluoromethyl)phenyl]-3-azabicyclo[3.1.0]hexane (Preparation 40, Enantiomer 2):

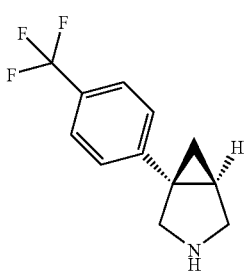

by using (S)-(+) acetyl mandelic acid as resolving agent.

In the literature the absolute configuration of a series of compounds similar to this chiral intermediate is known, see J. Med Chem 1981, 24(5), 481-90. For some compounds disclosed in the reference the absolute configuration was proved by single crystal X-ray analysis.

Among them, 1-(3,4-dichlorophenyl)-3-azabicyclo[3.1.0] hexane was disclosed.

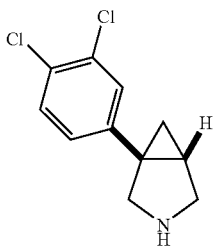

The absolute configuration of the optical isomers of the compounds of the present invention was assigned using comparative VCD (vibrational circular dichroism) and OR (optical rotation) analyses.

The configuration of (1S,5R)-1-(3,4-dichlorophenyl)-3-azabicyclo[3.1.0]hexane was assigned by comparing its experimental VCD spectrum and observed specific rotation to ab initio derived calculated data for (1S,5R)-1-(3,4-dichlorophenyl)-3-azabicyclo[3.1.0]hexane (see Preparation 50, Enantiomer 2) as the reference sample.

The assignment of the absolute configuration of the title compound was confirmed by a single crystal X-ray structure obtained from a crystal of (1S,5R)-1-[4-(trifluoromethyl) phenyl]-3-azabicyclo[3.1.0]hexane, (S)-(+)-mandelic acid salt. Both the analysis based on the known configuration of the (S)-(+)-mandelic acid and on the basis of anomalous dispersion effects confirmed the assignment of the title compound as being (1S,5R)-1-[4-(trifluoromethyl)phenyl]-3-azabicyclo[3.1.0]hexane.

For those compounds which were subjected to detailed analysis (VCD; OR included in the experimental details) a common trend was recognised between absolute configuration of the 3-azabicyclo[3.1.0]hexane moiety and measured binding activity at the dopamine D3 receptor for each pair of enantiomers. For the remainder of the compounds of the present invention, where stereoisomers were evaluated separately, absolute configuration was assigned based on a reasonable assumption by a skilled person in the art, i.e. absolute configuration was then assigned based on measured binding activity at the dopamine $D_3$ receptor for both enantiomers and comparison with the data of those compounds which were subjected to detailed analysis.

Chiral molecules exhibit vibrational circular dichroism (VCD). Vibrational circular dichroism (VCD) is the differential interaction of a chiral molecule with left and right circularly polarized infrared radiation during vibrational excitation.

The VCD spectrum of a chiral molecule is dependent on its three-dimensional structure. Most importantly, the VCD spectrum of a chiral molecule is a sensitive function of its absolute configuration and, in the case of flexible molecules, of its conformation. In principle, therefore, VCD permits the determination of the structure of a chiral molecule. VCD spectra were first measured in the 1970s. Subsequently, VCD instrumentation has developed enormously in spectral range and in sensitivity. Currently, VCD spectra of liquids and solutions can be measured over the majority of the fundamental infrared (IR) spectral range (v≧650 cm-1) with high sensitivity at acceptable resolution (1-5 cm-1) using both dispersive and Fourier Transform (FT) VCD instrumentation. Very recently, commercial FT VCD instrumentation has become available, greatly enhancing the accessibility of VCD spectra.

The use of VCD as a reliable method for the determination of absolute configuration of chiral molecules is now well established (see for example Shah R D, et al., Curr Opin Drug Disc Dev 2001;4:764-774; Freedman T B, et al., Helv Chim Acta 2002; 85:1160-1165; Dyatkin A B, et al. Chirality 2002; 14:215-219; Solladié -Cavallo A, Balaz M et al., Tetrahedron Assym 2001;12:2605-2611; Nafie L A, et al. Circular dichroism, principles and applications, 2nd ed. New York: John Wiley & Sons; 2000. p 97-131; Nafie L A, et al. in: Yan B, Gremlish H-U, editors. Infrared and Raman spectroscopy of biological materials. New York: Marcel Dekker; 2001. p 15-54; Polavarapu P L, et al., J Anal Chem 2000;366:727-734; Stephens P J, et al., Chirality 2000;12:172-179; Solladié -Cavallo A, et al., Eur J Org Chem 2002: 1788-1796).

The method entails comparison of observed IR and VCD spectra with calculations of the spectra for a specific configuration and provides information both on the absolute configuration and on the solution conformation.

Given an experimental spectrum of a chiral molecule whose absolute configuration and/or conformation are unknown and to be determined, the general procedure is as follows: 1) all possible structures are defined; 2) the spectra of these structures are predicted; and 3) predicted spectra are compared to the experimental spectrum. The correct structure will give a spectrum in agreement with experiment; incorrect structures will give spectra in disagreement with experiment.

VCD spectra are always measured simultaneously with vibrational unpolarized absorption spectra ("infrared (IR) spectra") and the two vibrational spectra together provide more information than does the VCD spectrum alone. In addition, vibrational unpolarized absorption spectra are automatically predicted simultaneously with VCD spectra.

For ab initio assignments, VCD and unpolarized IR spectra were calculated using the Gaussian 98 software package.

When chiral organic molecules are synthesized (or, if natural products, isolated) their optical rotations are routinely measured at one frequency or at a small number of discrete frequencies in the visible-near ultraviolet spectral region. Most commonly, the specific rotation at one frequency, that of the sodium D line, $[\alpha]_D$, is measured. The frequencies used lie below the threshold for electronic absorption, i.e., they are in the "transparent" spectral region. Optical rotation is a reflection of the enantiomeric excess (ee) of the sample and of the absolute configuration (AC) of the predominant enantiomer.

When the optical rotation at a given frequency for 100% ee is available, the measured optical rotation at the same frequency enables the sample ee to be determined. The determination of ee is the predominant application of discrete frequency, transparent spectral region optical rotations. In principle, the AC of the predominant enantiomer, if unknown, can also be determined. However, the determination of AC from optical rotation requires an algorithm which reliably predicts the optical rotations of molecules of known AC and a number of methodologies have been proposed for predicting discrete frequency, transparent spectral region optical rotations (Eliel E L, Wilen S H. Stereochemistry of organic compounds. New York: John Wiley & Sons; 1994. Chapter 13).

Very recently, developments in ab initio Density Functional Theory (DFT) have radically improved the accuracy of optical rotation calculation. As a result, for the first time it has become possible to routinely obtain ACs from optical rotations.

For ab initio OR assignments, the Dalton Quantum Chemistry Program was used.

Further embodiments of the present invention are compounds of formula (IB)' and (IC)' which, respectively, correspond to the stereochemical isomers of compounds of formula (IB) and (IC) as defined above enriched in configuration (1S, 5R).

Compounds of formula (ID)' correspond to the stereochemical isomers of compounds of formula (ID) as above defined, enriched in configuration (1R, 5R) or (1R, 5S) depending on the presence of a 2-pyridine ring.

In one embodiment, a stereochemical isomer enriched in the (1S,5R) configuration of formula (IB)' or a pharmaceutically acceptable salt thereof is provided, wherein $R_1$, $R_2$, $R_3$, $R_4$, p and n are as defined for formula (I):

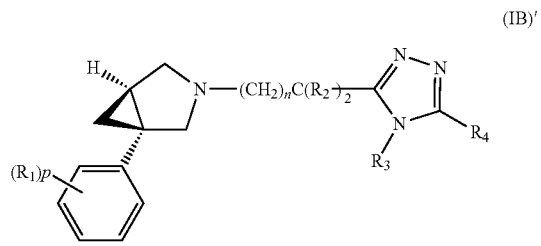

(IB)'

In Formula (IB)', in one embodiment, $R_3$ is methyl; $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.
In one embodiment, n is 3 or 4.
In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl), an optionally substituted benzyl group, an optionally substituted alkyl group (i.e. t-butyl), a thioalkyl group (i.e. thiomethylcyclopropyl, thiomethyl).

In Formula (IB)', in a further embodiment, $R_3$ is methyl; $R_4$ may be a $C_{1-4}$alkyl group, a benzyl group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$, or a group —$SR_6$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.
In one embodiment, n is 3 or 4.
In one embodiment, $R_1$ is halogen or trifluoromethyl.

Examples of $R_4$ include an optionally substituted benzyl group, an optionally substituted alkyl group (i.e. t-butyl), a thioalkyl group (i.e. thiomethylcyclopropyl, thiomethyl).

In Formula (IB)', in a still further embodiment, $R_3$ is methyl; both $R_2$ are at the same time methyl or fluorine.

In Formula (IB)', in another embodiment, both $R_2$ are at the same time methyl or fluorine; $R_3$ is methyl; $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.
In one embodiment, n is 3 or 4.
In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl), an optionally substituted benzyl group, an optionally substituted alkyl group (i.e. t-butyl), a thioalkyl group (i.e. thiomethylcyclopropyl, thiomethyl).

In another embodiment, a stereochemical isomer enriched in the (1S,5R) configuration of formula (IC)' or a pharmaceutically acceptable salt thereof is provided wherein $R_1$, p, n, $R_3$ and $R_4$ are as defined for formula (I):

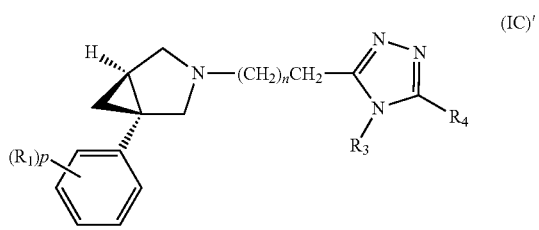

(IC)'

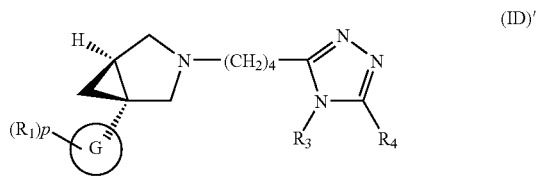

(ID)'

In Formula (IC)', in one embodiment, $R_3$ is methyl; $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.
In one embodiment, n is 3 or 4.
In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl), an optionally substituted benzyl group, an optionally substituted alkyl group (i.e. t-butyl), a thioalkyl group (i.e. thiomethylcyclopropyl, thiomethyl).

In Formula (IC)', in another embodiment, $R_3$ is methyl; $R_4$ may be a $C_{1-4}$alkyl group, a benzyl group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$, or a group —$SR_6$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.
In one embodiment, n is 3 or 4.
In one embodiment, $R_1$ is halogen or trifluoromethyl.

Examples of $R_4$ include an optionally substituted benzyl group, an optionally substituted alkyl group (i.e. t-butyl), a thioalkyl group (i.e. thiomethylcyclopropyl, thiomethyl).

In another embodiment, a stereochemical isomer enriched in the (1S,5R) configuration or (1R,5R) configuration of formula (ID)' or a pharmaceutically acceptable salt thereof is provided, wherein G is 2-pyridyl or 3-pyridyl and $R_1$, p, $R_3$ and $R_4$ are as defined for formula (I):

In Formula (ID)', in one embodiment, G corresponds to 2-pyridyl (Compounds (ID1)') and in another embodiment to 3-pyridyl (Compounds (ID2)'), as illustrated below:

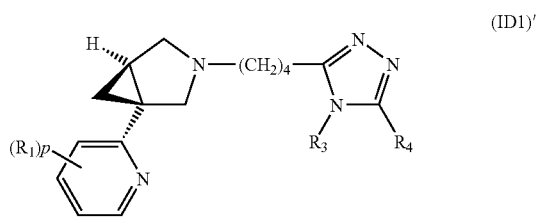

(ID1)'

(1R, 5R)

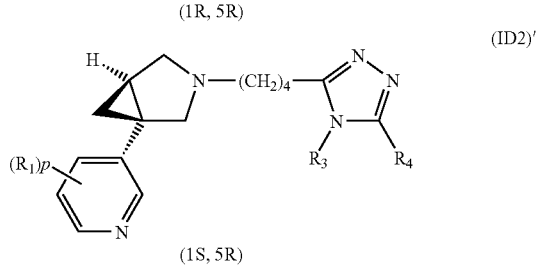

(ID2)'

(1S, 5R)

The configuration will then change depending on the type of pyridine ring, as mentioned above.

In Formulae (ID)', (ID1)' and (ID2)', in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl and $SF_5$; and when $R_1$ is chlorine and p is 1, such $R_1$ is not present in the ortho position with respect to the linking bond to the rest of the molecule; and when $R_1$ corresponds to $R_5$, p is 1.

In one embodiment, p is 1 or 2.
In one embodiment, n is 3 or 4.
In one embodiment, $R_1$ is halogen or trifluoromethyl.

Examples of $R_4$ include an optionally substituted phenyl (e.g. phenyl, trifluoromethyl-phenyl, difluorophenyl, fluorophenyl, chlorophenyl, methoxyphenyl, dichlorophenyl, cyanophenyl, trifluoromethoxyphenyl), an optionally substituted bicyclic group such as quinolinyl (e.g. 2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl, an optionally substituted pyrimidyl (e.g. 5-pyrimidinyl), an optionally substituted pyridazinyl, an optionally substituted pyrazinyl, an optionally substituted furanyl, an optionally substituted thienyl, an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl), an optionally substituted benzyl group, an optionally substituted alkyl group (i.e. t-butyl), a thioalkyl group (i.e. thiomethylcyclopropyl, thiomethyl).

Certain of the compounds of the invention may form acid addition salts with one or more equivalents of the acid. The present invention includes within its scope all possible stoichiometric and non-stoichiometric forms.

Pharmaceutical acceptable salts may also be prepared from other salts, including other salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

In one embodiment of the present invention compounds are provided having a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include:

(1S,5R)-1-[2-fluoro-4-(trifluoromethyl)phenyl]-3-[4-(4-methyl-5-phenyl-4H-1,2,4-triazol-3-yl)butyl]-3-azabicyclo[3.1.0]hexane;
(1R,5S/1S,5R)-3-[4-(4-methyl-5-phenyl-4H-1,2,4-triazol-3-yl)butyl]-1-[6-(trifluoromethyl)-3-pyridinyl]-3-azabicyclo[3.1.0]hexane;
(1S,5R)-3-[4-(4-methyl-5-phenyl-4H-1,2,4-triazol-3-yl)butyl]-1-[4-(trifluoromethyl)phenyl]-3-azabicyclo[3.1.0]hexane;
(1S,5R)-3-{4-[4-methyl-5-(4-pyridazinyl)-4H-1,2,4-triazol-3-yl]butyl}-1-[4-(trifluoromethyl)phenyl]-3-azabicyclo[3.1.0]hexane;
(1S,5R)-3-{4-[4-methyl-5-(2-methyl-3-pyridinyl)-4H-1,2,4-triazol-3-yl]butyl}-1-[4-(trifluoromethyl)phenyl]-3-azabicyclo[3.1.0]hexane;
(1S,5R)-3-{4-[4-methyl-5-(6-methyl-3-pyridinyl)-4H-1,2,4-triazol-3-yl]butyl}-1-[4-(trifluoromethyl)phenyl]-3-azabicyclo[3.1.0]hexane;
(1S,5R)-3-{4-[4-methyl-5-(5-methyl-2-pyrazinyl)-4H-1,2,4-triazol-3-yl]butyl}-1-[4-(trifluoromethyl)phenyl]-3-azabicyclo[3.1.0]hexane;
(1S,5R)-3-{4-[5-(2,4-dimethyl-1,3-oxazol-5-yl)-4-methyl-4H-1,2,4-triazol-3-yl]butyl}-1-[4-(trifluoromethyl)phenyl]-3-azabicyclo[3.1.0]hexane;
(1R,5S/1S,5R )-3-[4-(4-methyl-5-phenyl-4H-1,2,4-triazol-3-yl)butyl]-1-[5-(trifluoromethyl)-2-pyridinyl]-3-azabicyclo[3.1.0]hexane;
(1S,5R)-3-{4-[4-methyl-5-(2-methyl-1,3-thiazol-5-yl)-4H-1,2,4-triazol-3-yl]butyl}-1-[4-(trifluoromethyl)phenyl]-3-azabicyclo[3.1.0]hexane;
(1R,5S/1S,5R)-3-{4-[5-(3,4-difluorophenyl)-4-methyl-4H-1,2,4-triazol-3-yl]butyl}-1-[6-(trifluoromethyl)-3-pyridinyl]-3-azabicyclo[3.1.0]hexane;
(1S,5R )-3-{4-[5-(3,4-difluorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(tetrahydro-2H-pyran-4-yl)-4H-1,2,4-triazol-3-yl]butyl}-1-[4-(trifluoromethyl)phenyl]-3-azabicyclo[3.1.0]hexane;
(1S,5R)-3-[5-(4-methyl-5-phenyl-4H-1,2,4-triazol-3-yl)pentyl]-1-[4-(trifluoromethyl)phenyl]-3-azabicyclo[3.1.0]hexane;
(1S,5R)-3-{5-[4-methyl-5-(5-methyl-2-pyrazinyl)-4H-1,2,4-triazol-3-yl]pentyl}-1-[4-(trifluoromethyl)phenyl]-3-azabicyclo[3.1.0]hexane;
(1S,5R)-3-(4-{methyl-5-[4-(methyloxy)phenyl]-4H-1,2,4-triazol-3-yl}butyl)-1-[4-(trifluoromethyl)phenyl]-3-azabicyclo[3.1.0]hexane;
(1S,5R)-3-{4-[5-(2,4-dichlorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[5-(3-chlorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[5-(2-fluorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(4-methyl-1,3-thiazol-5-yl)-4H-1,2,4-triazol-3-yl]butyl}-1-[4-(trifluoromethyl)phenyl]-3-azabicyclo[3.1.0]hexane;
(1S,5R)-3-{4-[5-(2,4-dimethyl-1,3-thiazol-5-yl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(phenylmethyl)-4H-1,2,4-triazol-3-yl]butyl}-1-[4-(trifluoromethyl)phenyl]-3-azabicyclo[3.1.0]hexane;
(1S,5R)-3-{4-[5-(1,1-dimethylethyl)-4-methyl-4H-1,2,4-triazol-3-yl]butyl}-1-[4-(trifluoromethyl)phenyl]-3-azabicyclo[3.1.0]hexane;
(1S,5R)-3-{5-[5-(4-chlorophenyl)-4-methyl-4H-1,2,4-triazol-3-yl]pentyl}-1-[4-(trifluoromethyl)phenyl]-3-azabicyclo[3.1.0]hexane;
(1S,5R)-3-(4-{4-methyl-5-[2-methyl-6-(trifluoromethyl)-3-pyridinyl]-4H-1,2,4-triazol-3-yl}butyl)-1-[4-(trifluoromethyl)phenyl]-3-azabicyclo[3.1.0]hexane;
(1S,5R)-3-(4-{4-methyl-5-[3-(methyloxy)phenyl]-4H-1,2,4-triazol-3-yl}butyl)-1-[4-(trifluoromethyl)phenyl]-3-azabicyclo[3.1.0]hexane;
(1S,5R)-3-(4-{4-methyl-5-[2-(methyloxy)phenyl]-4H-1,2,4-triazol-3-yl}butyl)-1-[4-(trifluoromethyl)phenyl]-3-azabicyclo[3.1.0]hexane;
3-[4-methyl-5-(4-{(1S,5R)-1-[4-(trifluoromethyl)phenyl]-3-azabicyclo[3.1.0]hex-3-yl}butyl)-4H-1,2,4-triazol-3-yl]benzonitrile;
2-methyl-5-[4-methyl-5-(4-{(1S,5R)-1-[4-(trifluoromethyl)phenyl]-3-azabicyclo[3.1.0]hex-3-yl}butyl)-4H-1,2,4-triazol-3-yl]quinoline;
(1S,5R)-3-{4-[4-methyl-5-(1,3,5-trimethyl-1H-pyrazol-4-yl)-4H-1,2,4-triazol-3-yl]butyl}-1-[4-(trifluoromethyl)phenyl]-3-azabicyclo[3.1.0]hexane;
4-[4-methyl-5-(4-{(1S,5R)-1-[4-(trifluoromethyl)phenyl]-3-azabicyclo[3.1.0]hex-3-yl}butyl)-4H-1,2,4-triazol-3-yl]benzonitrile;
(1S,5R)-3-[4-methyl-4-(4-methyl-5-phenyl-4H-1,2,4-triazol-3-yl)pentyl]-1-[4-(trifluoromethyl)phenyl]-3-azabicyclo[3.1.0]hexane;
(1S,5R)-3-[4,4-difluoro-4-(4-methyl-5-phenyl-4H-1,2,4-triazol-3-yl)butyl]-1-[4-(trifluoromethyl)phenyl]-3-azabicyclo[3.1.0]hexane;
(1S,5R)-3-{4-[5-(3-fluorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[5-(2-chlorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(3-thienyl)-4H-1,2,4-triazol-3-yl]butyl}-1-[4-(trifluoromethyl)phenyl]-3-azabicyclo[3.1.0]hexane;
(1S,5R)-3-{4-[5-(2,4-difluorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(1-methyl-1H-pyrrol-2-yl)-4H-1,2,4-triazol-3-yl]butyl}-1-[4-(trifluoromethyl)phenyl]-3-azabicyclo[3.1.0]hexane;
(1S,5R)-3-{4-[5-(4-fluorophenyl)-4-methyl-4H-1,2,4-triazol-3-yl]butyl}-1-[4-(trifluoromethyl)phenyl]-3-azabicyclo[3.1.0]hexane;
(1S,5R)-3-(4-{4-methyl-5-[6-(methyloxy)-3-pyridinyl]-4H-1,2,4-triazol-3-yl}butyl)-1-[4-(trifluoromethyl)phenyl]-3-azabicyclo[3.1.0]hexane;

(1S,5R)-3-{4-[5-(3,5-difluorophenyl)-4-methyl-4H-1,2,4-triazol-3-yl]butyl}-1-[4-(trifluoromethyl)phenyl]-3-azabicyclo[3.1.0]hexane;

(1S,5R)-3-{5-[4-methyl-5-(4-methyl-1,3-oxazol-5-yl)-4H-1,2,4-triazol-3-yl]pentyl}-1-[4-(trifluoromethyl)phenyl]-3-azabicyclo[3.1.0]hexane (1S,5R)-3-(5-{4-methyl-5-[3-(methyloxy)phenyl]-4H-1,2,4-triazol-3-yl}pentyl)-1-[4-(trifluoromethyl)phenyl]-3-azabicyclo[3.1.0]hexane;

(1S,5R)-3-{5-[5-(2-chlorophenyl)-4-methyl-4H-1,2,4-triazol-3-yl]pentyl}-1-[4-(trifluoromethyl)phenyl]-3-azabicyclo[3.1.0]hexane;

(1S,5R)-3-{5-[5-(2,4-difluorophenyl)-4-methyl-4H-1,2,4-triazol-3-yl]pentyl}-1-[4-(trifluoromethyl)phenyl]-3-azabicyclo[3.1.0]hexane;

(1S,5R)-3-{4-[4-methyl-5-(methylthio)-4H-1,2,4-triazol-3-yl]butyl}-1-[4-(trifluoromethyl)phenyl]-3-azabicyclo[3.1.0]hexane;

(1S,5R)-3-(4-{5-[(cyclopropylmethyl)thio]-4-methyl-4H-1,2,4-triazol-3-yl}butyl)-1-[4-(trifluoromethyl)phenyl]-3-azabicyclo[3.1.0]hexane;

(1S,5R)-3-[4-(4-methyl-5-{4-[(trifluoromethyl)oxy]phenyl}-4H-1,2,4-triazol-3-yl)butyl]-1.-[4-(trifluoromethyl)phenyl]-3-azabicyclo[3.1.0]hexan;

and pharmeutically acceptable salts thereof.

The present invention also provides a process for preparing a compound of formula (I) or a pharmaceutically acceptable salt thereof as defined above.

The process of the present invention for preparing compounds of formula (I) comprises the steps of:

(a) reacting a compound of formula (II):

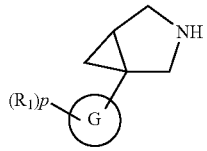

wherein G, $R_1$ and p are as defined for formula (I), with a compound of formula (III):

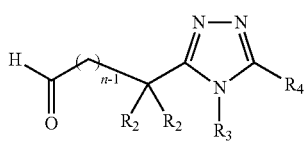

wherein $R_2$, $R_3$ and $R_4$ are as defined for formula (I); or (b) reacting a compound of formula (II):

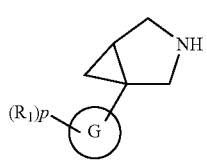

wherein G, $R_1$ and p are as defined for formula (I), with a compound of formula (XIII):

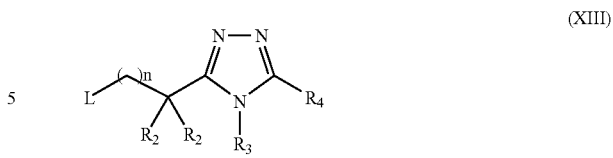

wherein $R_2$, $R_3$ and $R_4$ are as defined for formula (I) and L is a leaving group selected in a group consisting from: halogen or reactive residue of sulphonic acid (e.g. mesylate, tosylate); or (c) for a compound of formula (I) wherein p is 1 or 2, reacting a compound of formula (IV):

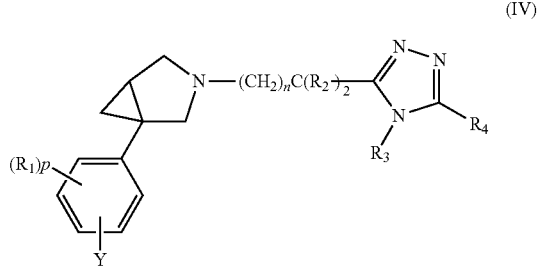

wherein $R_1$, $R_2$, $R_3$, and $R_4$ are as defined for formula (I), p is 0 or 1 and Y is halogen, a perfluoroalkylsulfonyloxy group (e.g. trifluoromethylsulfonyloxy), or Y is a group M selected from a boron derivative (e.g. a boronic acid function $B(OH)_2$) or a metal function such as trialkylstannyl (e.g. $SnBu_3$), zinc halide or magnesium halide; with a compound R1-Y1, wherein Y1 is halogen when Y is a group M; or when Y is halogen or a perfluoroalkylsulfonyloxy group Y1 is a group M as defined above or hydrogen that can be activated by a suitable base (e.g. $Cs_2CO_3$) in the presence of a suitable transition metal (e.g. Pd); "leaving group" is as understood by a skilled chemist, i.e. a group which can be displaced by a nucleophile in e.g. a $S_N2$, $S_N1$ or $S_NAr$ type reaction;

and thereafter optionally for process (a) or (b):
(i) removing any protecting group(s); and/or
(ii) forming a salt; and/or
(iii) converting a compound of formula (I) or a salt thereof to another compound of formula (I) or a salt thereof.

Process (a) may be performed using conventional methods. See Example 1 for typical reaction conditions.

Compounds of formula (II) may be prepared by methods well known in the art (e.g. *J. Med. Chem.* 1981, 24, 481-490). Interconversion of groups $R_1$ may be effected by methodology well known in the art (e.g. demethylation of a methoxy group resulting in a hydroxy group using a suitable Lewis acidic reagent such as boron tribromide in an inert solvent such as dichloromethane), sence of a suitable protecting group for the secondary amine, such as N-trifluoroacetyl.

Compounds of formula (III) may be prepared by methods well known in the art.

Reaction of a compound of formula (IV) with R1-Y1 according to process (b) may be effected in the presence of a transition metal e.g., palladium catalyst such as bis-triphenylphosphinepalladium dichloride, tetrakis-triphenylphosphinepalladium (0) or the complex formed in situ from tris (dibenzylideneacetone) dipalladium(0) and 4,5-bis (diphenylphosphino)-9,9-dimethylxanthene. When M is a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. When M is hydrogen that can be activated by a suitable base (e.g. $Cs_2CO_3$) in the presence of a suitable transition metal (e.g. Pd) the reaction may be carried out in an inert solvent such as dioxane in the presence of a suitable base such as $Cs_2CO_3$. The substituent Y may be halogen such as bromine, or a sulfonyloxy group such as trifluoromethylsulfonyloxy; and Y1 is may be a group M, such as hydrogen that can be activated by a suitable base (e.g. $Cs_2CO_3$) in the presence of a suitable transition metal (e.g. Pd).

In one aspect of the present invention, there is provided a synthetic process for the preparation of compounds of formula (II) wherein G is phenyl. The process may be conveniently performed also for preparing compounds of formula (IIa), in which the phenyl moiety is replaced by pyridine, useful for preparing compounds of formula (IE). This process comprises the following steps:

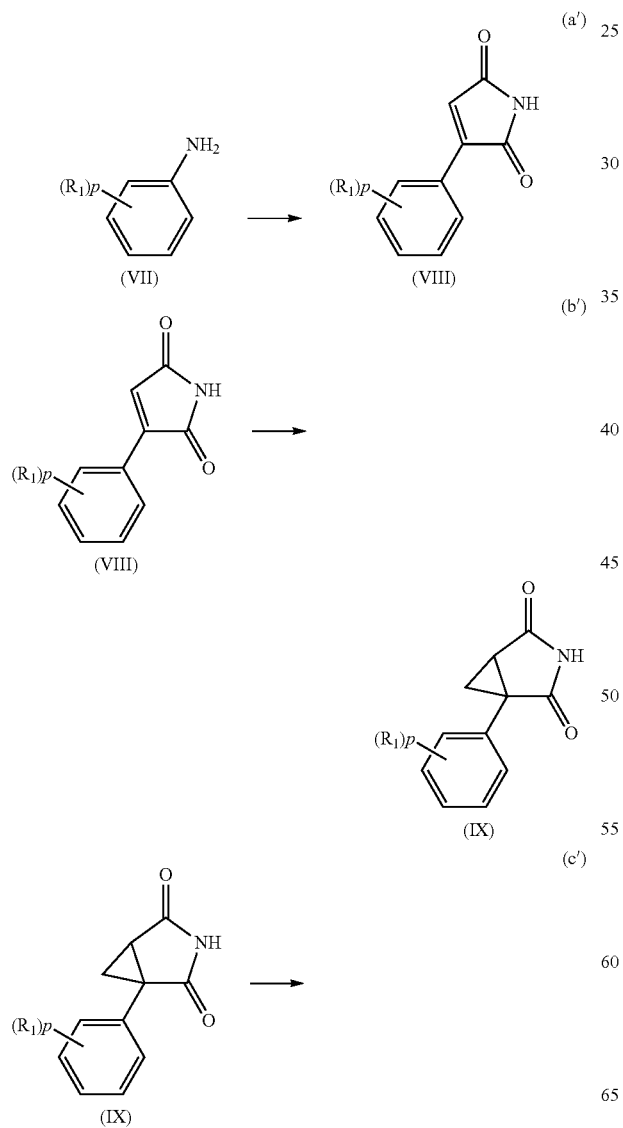

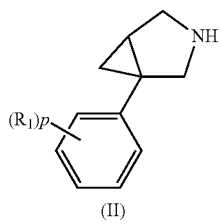

wherein:
step(a') means diazotation of an aniline (VII) followed by reaction with maleimide to give 3-arylmaleimide (VII);

step (b') means cycloropanation of (VIII) to provide bicyclic imide (IX);

step (c') means reduction of imide (IX) to give compounds of formula (II).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous $CuCl_2$, and a suitable organonitrite, such as tert-butyl nitrite, in a compatible solvent, such as acetonitrile, is slowly added a solution of a compound of formula (VII). This is followed by allowing time to react as appropriate and a suitable workup.

Step (b') consists of slow addition of a solution of purified compound of formula (VIII), or mixtures containing a compound of formula (VIII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

In another aspect of the present invention an alternative synthetic process for the preparation of compounds of formula (II) is provided, comprising the following steps:

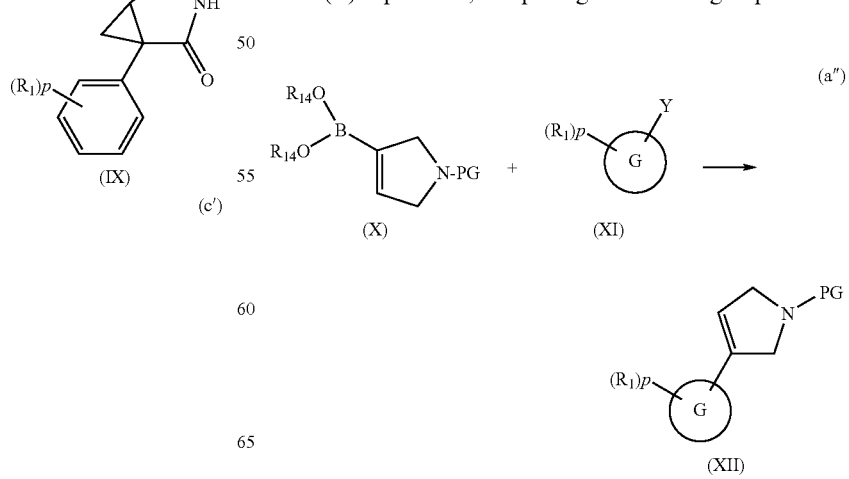

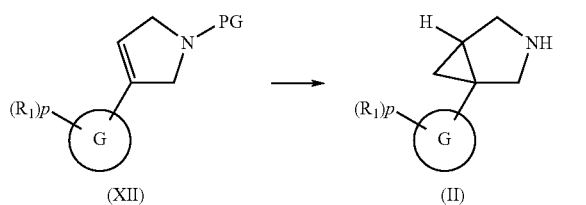

wherein:

$R_1$, p and G are as defined for formula (I), $R_{14}O$ is a suitable alkoxy group, PG is an appropriate protecting group and Y may be halogen such as bromine, or a sulfonyloxy group such as trifluoromethylsulfonyloxy; wherein step (a″) means coupling reaction of a (2,5-dihydro-1H-pyrrol-3-yl)boronate (X) with the aromatic halogen or sulfonyloxy derivative (XI);

step (b″) means cyclopropanation of (XII) followed by, if appropriate, deprotection to provide bicyclic amine (II).

Step (a″) may be effected using conventional methods for the Suzuki coupling, e.g. using tetrakis(triphenylphosphine)palladium(0) as the source of catalytic palladium(0) in the presence of cesium fluoride in an appropriate solvent such as tetrahydrofuran at a suitable temperature. $(R_{14}O)_2B$ may suitably be 4,4,5,5-tetramethyl-1,3,2-dioxaborolan-2-yl and PG benzyl, representing a compound of structure (X) as reported in Synlett 2002, 5, 829-831.

Step (b″) consists of a cyclopropanation reaction effected for example using the reagent generated from trimethylsulfoxonium iodide and a suitable base such as sodium hydride, in a compatible solvent, for example dimethylsulfoxide. This is followed by a deprotection reaction.

Interconversion reactions between compounds of formula (I) and salts thereof may be performed using methods well known in the art. Examples include:

(i) converting one or more of $R_1$ from alkoxy (e.g. methoxy) to hydroxy, (ii) converting one or more of $R_1$ from hydroxy to sulfonyloxy, such as alkylsulfonyloxy or haloalkylsulfonyloxy, e.g. methanesulfonyloxy or alkylsulfonyloxy or trifluoromethanesulfonyloxy, (iii) converting one or more of $R_1$ from halogen or perfluoroalkylsulfonyloxy to cyano; and optionally thereafter forming a salt of formula (I).

Compounds of formula (I) have been found to exhibit affinity for dopamine receptors, in particular the $D_3$ receptor, and are expected to be useful in the treatment of disease states which require modulation of such receptors, such as psychotic conditions. Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, Biochem. Pharmacol. 22:3099, 1973).

In the context of the present invention pKi (corresponding to the antilogarithm of Ki) is used instead of Ki and the compounds of the present invention typically show pKi greater than 7. In one aspect the present invention provides compounds of formula (I) having a pKi comprised between 7 and 8. In another aspect the present invention provides compounds of formula (I) having a pKi between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No.4, 295-314, 1993). In one embodiment compounds of the present invention are provided which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, sexual dysfunction, sleep disorders, emesis, movement disorders, amnesia, aggression, autism, vertigo, dementia, circadian rhythm disorders and gastric motility disorders e.g. IBS.

Other conditions which may be treated with the compounds of the invention include obsessive compulsive (OC) spectrum disorders as below defined.

Compounds of formula (I) may be used for treatment of all aspects of drug dependency including withdrawal symptoms from drugs of abuse such as alcohol, cocaine, opiates, nicotine, benzodiazepines and inhibition of tolerance induced by opioids. In addition, compounds of formula (I) and pharmaceutically acceptable salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242).

Compounds of formula (I) may be used for the treatment of obsessive compulsive disorders (OCD) and of psychiatric and neurospychiatric disorders related to them (OC spectrum disorders).

Compounds of formula (I) may be useful in the treatment of sexual dysfunction, such as premature ejaculation.

Compounds of formula (I) may be useful for the treatment of cognition impairment.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention.

Numbers in brackets after the listed diseases below refer to the classification code in DSM-IV.

Within the context of the present invention, the term "psychotic disorder" includes:

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the present invention, the term "substance-related disorder" includes:

Substance-related disorders including Substance Use Disorders such as Substance Dependence, Substance Craving and Substance Abuse; Substance-Induced Disorders such as Substance Intoxication, Substance Withdrawal, Substance-induced Delirium, Substance-Induced Persisting Dementia, Substance-Induced Persisting Amnestic Disorder, Substance-Induced Psychotic Disorder, Substance-induced Mood Disorder, Substance-Induced Anxiety Disorder, Substance-induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-induced Psychotic Disorder, Alcohol-induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-induced Mood Disorder, Hallucinogen-induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Within the context of the present invention, the term "obsessive compulsive spectrum disorder" includes:

Obsessive compulsive disorders (300.3), somatoform disorders including body dysmorphic disorder (300.7) and hyperchondriasis (300.7), bulimia nervosa (307.51), anorexia nervosa (307.1), eating disorders not elsewhere classified (307.50) such as binge eating, impulse control disorders not elsewhere classified (including intermitted explosive disorder (312.34), compulsive buying or shopping, repetitive self-mutilation, onychophagia, psychogenic excoriation, kleptomania (312.32), pathological gambling (312.31), trichotillomania (312.39) and internet addiction), paraphilia (302.70) and nonparaphilic sexual addictions, Sydeham's chorea, torticollis, autistic disorders (299.0), compulsive hoarding, and movement disorders, including Tourette's syndrome (307.23).

Within the context of the present invention, the term "sexual dysfunction" includes also premature ejaculation (302.75).

Within the present invention the term "cognition impairment" includes cognition impairment in other diseases such as schizophrenia, bipolar disorder, depression, other psychiatric disorders and psychotic conditions associated with cognitive impairment, e.g. Alzheimer's disease.

In a further aspect therefore the present invention provides a method of treating a condition for which modulation [especially inhibition/antagonism (which may also translate into inverse agonism in constitutively active receptor systems)] of dopamine receptors (especially dopamine $D_3$ receptors) is beneficial, which comprises administering to a mammal (e.g. human) in need thereof an effective amount of a compound of formula (I) or a pharmaceutically (i.e. physiologically) acceptable salt thereof.

Thus, a still further aspect the invention provides a method of treating a psychotic condition (e.g. schizophrenia) or substance abuse or obsessive compulsive spectrum disorders (such as binge eating) or sexual dysfunctions (such as premature ejaculation) which comprises administering to a mammal (e.g. human) in need thereof an effective amount of a compound of formula (I) as herein defined or a pharmaceutically acceptable salt thereof.

The invention also provides a compound of formula (I) or a pharmaceutically acceptable salt thereof for use in therapy.

The invention also provides a compound of formula (I) or a pharmaceutically acceptable salt thereof for use in the treatment of a condition in a mammal for which modulation [especially inhibition/antagonism (which may also translate into inverse agonism in constitutively active receptor systems)] of dopamine receptors (especially dopamine $D_3$ receptors) is beneficial.

The invention also provides the use of a compound of formula (I) or a pharmaceutically acceptable salt thereof in the manufacture of a medicament for the treatment of a condition in a mammal for which modulation [especially inhibition/antagonism (which may also translate into inverse agonism in constitutively active receptor systems)] of dopamine receptors (especially dopamine $D_3$ receptors) is beneficial.

In one embodiment, $D_3$ antagonists according to the present invention are used in the treatment of psychoses such as schizophrenia, in the treatment of substance abuse, in the treatment of obsessive compulsive spectrum disorders, in the treatment of sexual dysfunction and in the treatment of cognition impairment.

Also provided is the use of a compound of formula (I) or a pharmaceutically acceptable salt thereof in the manufacture of a medicament for the treatment of a psychotic condition (e.g. schizophrenia), substance abuse in a mammal, obsessive compulsive spectrum disorders, sexual dysfunctions and cognition impairment.

Also provided is a compound of formula (I) or a pharmaceutically acceptable salt thereof for use in the treatment of a psychotic condition (e.g. schizophrenia), substance abuse, obsessive compulsive spectrum disorders, sexual dysfunction and cognition impairment in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e. physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their salts which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line
CHO_D2
CHO_D3

Compounds may be tested according to two alternative protocols:

a) Cell membranes are prepared as follows. Cell pellets are resuspended in 10 volumes of 50 mM HEPES, 1MM EDTA pH 7.4, using KOH. On the day the following proteases are added to the buffer just prior to giving the homogenisation buffer.

$10^{-6}$M Leupeptin (Sigma L2884)–5000×stock=5 mg/ml in buffer 25 ug/ml Bacitracin (Sigma B0125)–1000×stock=25 mg/ml in buffer 1MM PMSF–1000×stock=17 mg/ml in 100% ethanol $2×10^{-6}$M Pepstain A–1000×stock=2 mM in 100% DMSO The cells are homogenised by 2×15 second bursts in a 1 liter Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at −800° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 1MM $MgCl_2$, 60 µg/ml saponin and 30 µM GDP is added. The third addition was a 20% TAV addition of either buffer, (agonist format) or $EC_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160 Ci/mmol, Amersham). After all additions assay plates are spun down for 1Min at 1,000 rpm. Assay plates are counted on a Viewlux, 613/55 filter, for 5 min., between 2-6 hours after the final addition.

The effect of the test drug over the basal generates $EC_{50}$ value by an iterative least squares curve fitting programme, expressed in the table as $pEC_{50}$ (i.e. $-logEC_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: $fKi=IC_{50}/1+([A]/EC_{50})$ where: [A] is the concentration of the agonist 5-HT in the assay and $EC_{50}$ is the 5-HT $EC_{50}$ value obtained in the same experiment. fpKi is defined as $-logfKi$.

b) Cell membranes are prepared as follows. Cell pellets are resuspended in 10 volumes of 50 mM HEPES, 1MM EDTA pH 7.4, using KOH. On the day the following proteases are added to the buffer just prior to giving the homogenisation buffer.

$10^{-4}$M Leupeptin (Sigma L2884)–5000×stock=5 mg/ml in buffer 25 ug/ml Bacitracin (Sigma B0125)–1000×stock=25 mg/ml in buffer 1MM PMSF–1000×stock=17 mg/ml in 100% ethanol $2×10^{-6}$M Pepstain A–1000×stock=2 mM in 100% DMSO The cells were homgenised within a glass waring blender for 2×15 secs in 200 mls of 50 mM HEPES+10-4M leupeptin+25 ug/ml bacitracin+1MM EDTA+1MM PMSF+2uM Pepstatin A, (the latter 2 reagents added as fresh ×100 and ×500 stocks respectively in ethanol). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and Pepstatin A. The material was then forced through a 0.6mm needle, made up to the required volume, (usually ×4 the volume of the original cell pellet), aliquoted and stored frozen at −80 deg C.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 60 mins at RT) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM MgCl2, 60 µg/ml saponin and 30 µM GDP is added. The third addition was a 20% TAV addition of either buffer, (agonist format) or EC80 final assay concentration of agonist, Quinelorane, prepared in assay buffer (antagonist format). The assay was started by the addition of 29% TAV of GTP [35S] 0.38 nM final (37 MBq/ml, 1160 Ci/mmol, Amersham). After all additions assay plates are spun down for 1Min at 1,000 rpm. Assay plates are counted on a Viewlux, 613/55 filter, for 5 min., between 3-6 hours after the final addition.

The effect of the test drug over the basal generates EC50 value by an iterative least squares curve fitting programme, expressed in the table as pEC50 (i.e. −logEC50). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as −logfKi.

The compounds of the invention listed above have pKi values within the range of 7.0-10.5 at the dopamine D3 receptor. pKi results are only estimated to be accurate to about ±0.3-0.5.

The compounds of the invention listed above have a selectivity over D2 greater than 30.

EXAMPLES

The invention is further illustrated by the following non-limiting examples.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from $Me_4Si$, used as internal standard, and are assigned as singlets (s), broad singlets (bs), doublets (d), doublets of doublets (dd), triplets (t), quartets (q) or multiplets (m).

Experimental vibrational circular dichroism (VCD) spectra were measured using a ChiralIR™ VCD spectrometer operating in the 2000-800 cm-1 frequency range. Spectra were measured at room temperature (23° C) using a sealed transmission cell with barium fluoride windows and a path length of 100 microns. (Scan times varied from 60 to 120 minutes per isomer.) Sample solutions were typically prepared by dissolving 10 milligrams of each enantiomer in 100 microliters of deutero-chloroform ($CDCl_3$). For ab initio assignments, VCD and unpolarized IR spectra were calculated using the Gaussian 98 software package.1.

Optical rotations were measured using a (Perkin Elmer Model 241) polarimeter operating at 589 nm (Sodium source). Measurements were made using a 1 decimeter microcell thermostated at 23° C. Concentrations were typically 10 mg/ml (c=0.01). For ab initio OR assignments, the Dalton Quantum Chemistry Program was used.

Column chromatography was carried out over silica gel (Merck AG Darmstaadt, Germany). The following abbreviations are used in the text: NMP=N-methylpyrrolidone; $Et_2O$=dietyl ether; MeOH=methanol; EtOH=ethanol; THF=tetrahydrofuran; DCM=dichloromethane; AcOH=Acetic acid; $NaBH(AcO)_3$=sodium triacetoxy boron hydride; 9-BBN=9-borabicyclo[3.3.1]nonane; $OsO_4$ on resin=Osmium tetroxide, polymer-bound FibreCat (™: trade mark), Aldrich SCX=strong cation exchanger; Tlc refers to thin layer chromatography on silica plates, and dried refers to a solution dried over anhydrous sodium sulphate, r.t. (RT) refers to room temperature, Rt=retention time.

Preparation 1 methyl 5-hexenimidoate hydrochloride

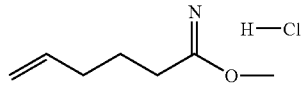

Through a stirred solution of 5-hexenenitrile (3 g, 31Mmol) and MeOH (35 mmol) in $Et_2O$ (30 ml), at 0° C., HCl gas was bubbled for 10 minutes. Solvent was evaporated in vacuo and the residue treated with $Et_2O$ to give 5.1 g of the title compound as white solid, which was used without further purification.

NMR ($^1$H, $CDCl_3$): δ 5.75 (m, 1H), 5.05 (m, 2H), 4.25 (s, 3H), 2.75 (t, 2H), 2.1 (dd, 2H), 1.85 (m, 2H). MS (m/z): 128[MH]$^+$.

Preparation 2

N,N'-dimethyl-5-hexen imidamide hydrochloride

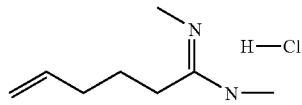

To a solution of methyl 5-hexenimidoate hydrochloride (4.63 g, 28 mmol, Prep. 1) in MeOH (20 ml) was added methylamine 8M in EtOH (142 mmol). The solution was heated to reflux for 6 h and stirred overnight at r.t. Volatiles were evaporated in vacuo to give 4.4 g of the title compound as pale yellow oil, which was used without further purification.

NMR ($^1$H, MeOD): δ 5.75 (m, 1H), 4.97 (m, 2H), 2.95 (s, 3H), 2.75 (s, 3H), 2.43 (m, 2H), 2.08 (m, 2H), 1.65 (m, 2H). MS (m/z): 141[MH]$^+$.

Preparation 3 methyl 4-pyridazinecarboxylic acid

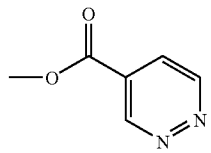

To a solution of 4-pyridazinecarboxylic acid (490 mg, 3.9 mmol) in MeOH/DCM (20/10 ml) was added at 0° C. trimethylsilildiazomethane (25.5 mmol). The solution was warm at r.t. and stirred overnight. Volatiles were evaporated in vacuo, the crude dissolved in DCM, washed with $NaHCO_3$ satured and dried over $Na_2SO_4$. After filtration and concentration to dryness in vacuo, the crude was purified by column chromatography (DCM:MeOH=98 to 2) to give 400 mg of the title compound.

NMR (¹H, CDCl3): δ 9.65 (s, 1H), 9.4 (d, 1H), 7.98 (d, 1H), 4.0 (s, 3H).

MS (m/z): 139[MH]⁺.

Preparation 4

4-pyridazinecarbohydrazide

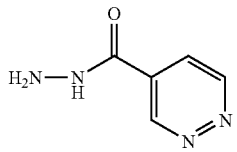

To a solution of methyl 4-pyridazinecarboxylate (400 mg, 2.9 mmol) in MeOH (5 ml) was added hydrazine monohydrate (23 mmol). The solution was heated to reflux for 12 h. Volatiles were evaporated in vacuo to give 395 mg of the title compound as a yellow pale foam, which was used without further purification.

NMR (¹H, DMSO): δ 9.5 (s, 1H), 9.4 (d, 1H), 7.98 (d, 1H), NH and NH2 not observed.

MS (m/z): 139[MH]⁺.

Preparation 5

2-methyl-3-pyridinecarbohydrazide

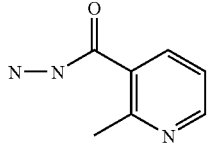

The title compound was prepared in analogy to the method described in Preparation 4 in 0.9 g yield as a white slightly hygroscopic solid from ethyl 2-methyl-3-pyridinecarboxylate (1 g). MS (m/z): 152[MH]+.

Preparation 6

6-methyl-3-pyridinecarbohydrazide

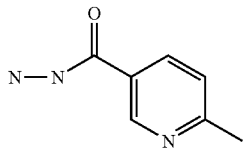

The title compound was prepared in analogy to the method described in Preparation 4 in 1.8 g yield as a white slightly hygroscopic solid from methyl 4-methyl-3-pyridinecarboxylate (1.8 g). MS (m/z): 152[MH]+.

Preparation 7

5-methyl-2-pyrazinecarbohydrazide

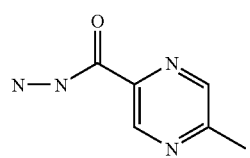

The title compound was prepared in analogy to the method described in Preparation 4 in 1.85 g yield as a white slightly hygroscopic solid from 5-methyl-2-pyrazinecarboxylate (1.85 mg). MS (m/z): 153[MH]+.

Preparation 8

2,4-dimethyl-1,3-oxazole-5-carbohydrazide

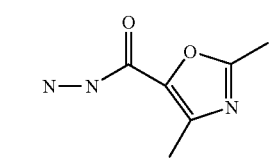

The title compound was prepared in analogy to the method described in Preparation 4 in 460 mg yield as a pale yellow gum from 2,4-dimethyl-1,3-oxazole-5-carboxylate (500 mg). MS (m/z): 459[MH]+.

Preparation 9

2-methyl-1,3-thiazole-5-carbohydrazide

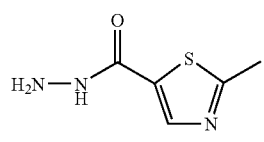

The title compound was prepared in analogy to the method described in Preparation 4 starting from ethyl 2-methyl-1,3- thiazole-5-carboxylate (0.5 g) and used without further purification. Ethanol was used instead of methanol. MS (m/z): 158.1[MH]+.

Preparation 10 tetrahydro-2H-pyran-4-carbohydrazide

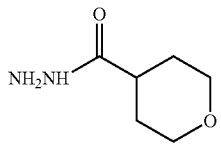

The title compound was prepared in analogy to the method described in Preparation 4 in 1.17 g yield as a white solid from methyl tetrahydro-2H-pyran-4-carboxylate (1.0 g). MS (m/z): 145[MH]+.

Preparation 11

4-methyl-3-(4-penten-1-yl)-5-phenyl-4H-1,2,4-triazole

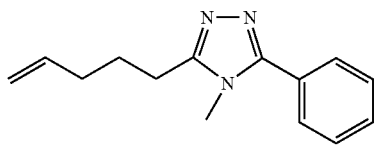

To a solution of N,N'-dimethyl-5-hexenimidamide hydrochloride (3.1Mmol) in MeOH (20 ml) were added K$_2$CO$_3$ (3.1Mmol) and benzhydrazide (3.1Mmol). The solution was heated to reflux for 24 h. Volatiles were evaporated in vacuo, the crude dissolved in DCM, washed with water and dried over Na$_2$SO$_4$. After filtration and concentration to dryness in vacuo, the crude was purified by column chromatography (DCM:MeOH=98 to 2) to give 196 mg of the title compound.

NMR ($^1$H, CDCl$_3$): δ 7.6 (m, 2H), 7.5 (m, 3H), 5.92 (m,1H), 5.03 (m, 2H), 3.52 (s, 3H), 2.8 (t, 2H), 2.2(dd, 2H), 1.95 (m, 2H). MS (m/z): 228[MH]+.

Preparation 12

4-[4-methyl-5-(4-penten-1-yl)-4H-1,2,4-triazol-3-yl]pyridazine

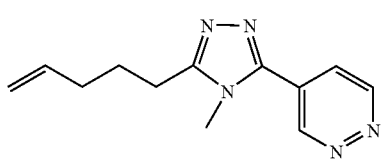

The title compound was prepared in analogy to the method described in Preparation 11 in 272 mg yield as a pale yellow gum from 4-pyridazinecarbohydrazide (400 mg). MS (m/z): 230[MH]+.

Preparation 13

2-methyl-3-[4-methyl-5-(4-penten-1-yl)-4H-1,2,4-triazol-3-yl]pyridine

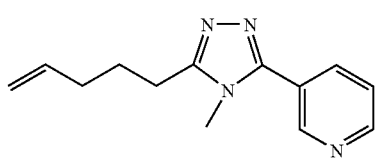

The title compound was prepared in analogy to the method described in Preparation 11 in 215 mg yield as a pale yellow gum from 2-methyl-3-pyridinecarbohydrazide (2.8 mmol). MS (m/z): 243[MH]+.

Preparation 14

2-methyl-5-[4-methyl-5-(4-penten-1-yl)-4H-1,2,4-triazol-3-yl]pyridine

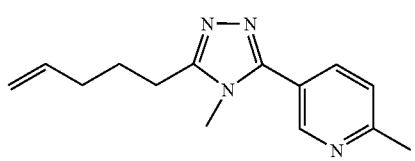

The title compound was prepared in analogy to the metnoa described in Preparation 11 in 550 mg yield as a pale yellow gum from 4-methyl-3-pyridinecarbohydrazide (3.3 mmol). MS (m/z): 242[MH]+.

Preparation 15

2-methyl-5-[4-methyl-5-(4-penten-1-yl)-4H-1,2,4-triazol-3-yl]pyrazine

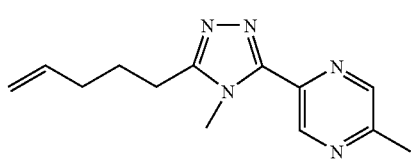

The title compound was prepared in analogy to the method described in Preparation 11 in 380 mg yield as a pale yellow gum from 5-methyl-2-pyrazinecarbohydrazide (3.3 mmol). MS (m/z): 243[MH]+.

Preparation 16

3-(2,4-dimethyl-1,3-oxazol-5-yl)-4-methyl-5-(4-penten-1-yl)-4H-1,2,4-triazole

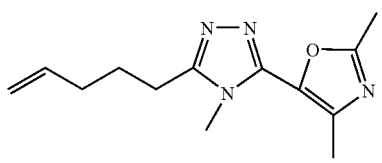

The title compound was prepared in analogy to the method described in Preparation 11 in 40 mg yield as a pale yellow gum from 2,4-dimethyl-1,3-oxazole-5-carbohydrazide (2.9 mmol). MS (m/z): 247[MH]+.

Preparation 17

4-methyl-3-(2-methyl-1,3-thiazol-5-yl)-5-(4-penten-1-yl)-4H-1,2,4-triazole

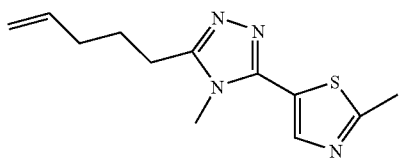

The title compound was prepared in analogy to the method described in Preparation 11 starting from 2-methyl-1,3-thiazole-5-carbohydrazide and N,N'-dimethyl-5-hexenimidamide hydrochloride in 43% yield by column chromatography. MS (m/z): 249.1[MH]+.

Preparation 18

3-(3,4-difluorophenyl)-4-methyl-5-(4-penten-1-yl)-4H-1,2,4-triazole

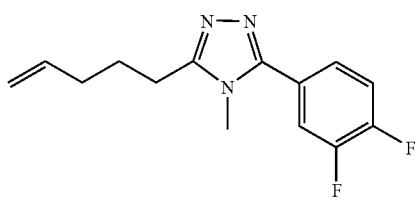

The title compound was prepared in analogy to the method described in Preparation 11 in 222 mg yield as a yellow oil from N,N'-dimethyl-5-hexenimidamide hydrochloride (400 mg) and 3,4-difluorobenzohydrazide (390 mg). MS (m/z): 264 [MH]+

Preparation 19

4-methyl-3-(4-penten-1-yl)-5-(tetrahydro-2H-pyran-4-yl)-4H-1,2,4-triazole

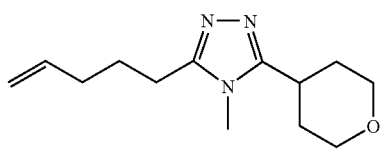

The title compound was prepared in analogy to the method described in Preparation 11 in 84 mg yield as a yellow oil (y=15%) from N,N'-Dimethyl-5-hexenimidamide hydrochloride (400 mg) and tetrahydro-2H-pyran-4-carbohydrazide (327 mg).
MS (m/z): 145[MH]+.

Preparation 20

4-(4-methyl-5-phenyl-4H-1,2,4-triazol-3-yl)butanal

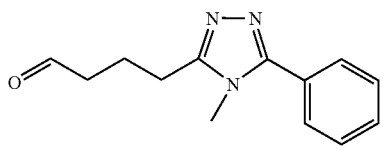

To a solution of 4-methyl-3-(4-penten-1-yl)-5-phenyl-4H-1,2,4-triazole (196 mg, 0.86 mmol) in THF/H$_2$O (7.5/1.5 ml) were added OsO$_4$ (4% solution in water, 0.04 mmol) and NaIO$_4$ (2.6 mmol). The solution was stirred o.n. at r.t. Water was added and product was extract with DCM. The organic phase was separated, dried over Na$_2$SO$_4$ and filtered. Volatiles were evaporated in vacuo to give 178 mg of the title compound as an oil, which was used in the subsequent step without further purification.
NMR ($^1$H, CDCl$_3$): δ 9.8 (s,1H), 7.6 (bm, 2H), 7.5 (bm, 3H), 5.52 (bm,1H), 5.28 (bm, 2H), 3.6 (s, 3H), 2.85 (bm, 2H), 2.7 (bm, 2H), 2.15 (bm, 2H). MS (m/z): 230[MH]+.

Preparation 21

4-[4-methyl-5-(4-pyridazinyl)-4H-1,2,4-triazol-3-yl]butanal

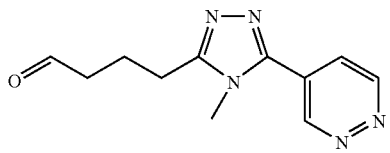

The title compound was prepared in analogy to the method described in Preparation 20 in 155 mg yield as a white slightly hygroscopic solid from 4-[4-methyl-5-(4-penten-1-yl)-4H-1,2,4-triazol-3-yl]pyridazine (272 mg). MS (m/z): 232[MH]+.

Preparation 22

4-[4-methyl-5-(2-methyl-3-pyridinyl)-4H-1,2,4-triazol-3-yl]butanal

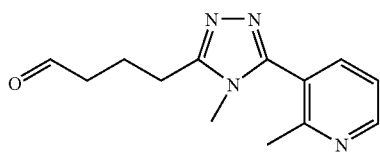

The title compound was prepared in analogy to the method described in Preparation 20 in mg yield as a white slightly hygroscopic solid from 2-methyl-3-[4-methyl-5-(4-penten-1-yl)-4H-1,2,4-triazol-3-yl]pyridine (215 mg). MS (m/z): 244[MH]+.

Preparation 23

4-[4-methyl-5-(6-methyl-3-pyridinyl)-4H-1,2,4-triazol-3-yl]butanal

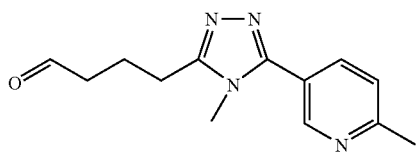

The title compound was prepared in analogy to the method described in Preparation 20 in 470 mg yield as a white slightly hygroscopic solid from 2-methyl-5-[4-methyl-5-(4-penten-1-yl)-4H-1,2,4-triazol-3-yl]pyridine (550 mg). MS (m/z): 244[MH]+.

Preparation 24

2 4-[4-methyl-5-(5-methyl-2-pyrazinyl)-4H-1,2,4-triazol-3-yl]butanal

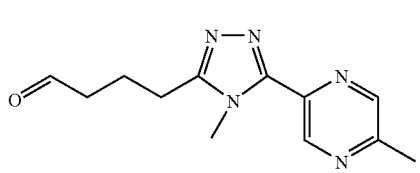

The title compound was prepared in analogy to the method described in Preparation 20 in 220 mg yield as a white slightly hygroscopic solid from 2-methyl-5-[4-methyl-5-(4-penten-1-yl)-4H-1,2,4-triazol-3-yl]pyrazine (300 mg). MS (m/z): 245[MH]+.

Preparation 25

4-[5-(2,4-dimethyl-1,3-oxazol-5-yl)-4-methyl-4H-1,2,4-triazol-3-yl]butanal

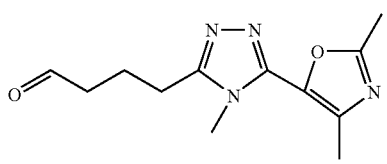

The title compound was prepared in analogy to the method described in Preparation 20 in 19 mg yield as a light yellow oil from 3-(2,4-dimethyl-1,3-oxazol-5-yl)-4-methyl-5-(4-penten-1-yl)-4H-1,2,4-triazole (40 mg). MS (m/z): 249[MH]+.

Preparation 26

4-[4-methyl-5-(2-methyl-1,3-thiazol-5-yl)-4H-1,2,4-triazol-3-yl]butanal

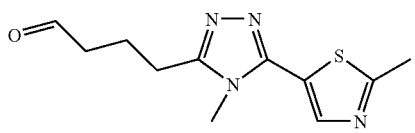

The title compound was prepared in analogy to the method described in Preparation 20 starting from 4-methyl-3-(2-methyl-1,3-thiazol-5-yl)-5-(4-penten-1-yl)-4H-1,2,4-triazole in quantitative yield and used without further purification. MS (m/z): 251.1[MH]+.

Preparation 27

4-[5-(3,4-difluorophenyl)-4-methyl-4H-1,2,4-triazol-3-yl]butanal

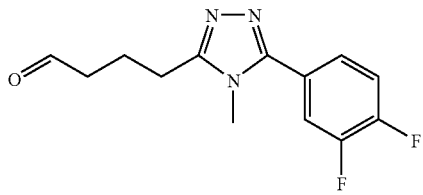

The title compound was prepared in analogy to the method described in Preparation 20 in 112 mg yield as a brown solid starting from 3-(3,4-difluorophenyl)-4-methyl-5-(4-penten-1-yl)-4H-1,2,4-triazole (222 mg). MS (m/z): 266[MH]⁺.

Preparation 28

4-[4-methyl-5-(tetrahydro-2H-pyran4-yl)-4H-1,2,4-triazol-3-yl]butanal

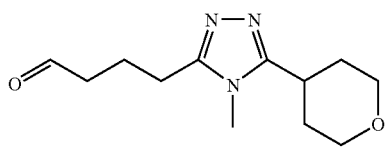

The title compound was prepared in analogy to the method described in Preparation 20 in 36 mg yield as a brown solid from 4-methyl-3-(4-penten-1-yl)-5-(tetrahydro-2H-pyran-4-yl)-4H-1,2,4-triazole (84 mg). MS (m/z): 238[MH]⁺.

Preparation 29

5-(4-methyl-5-phenyl-4H-1,2,4-triazol-3-yl)-1-pentanol

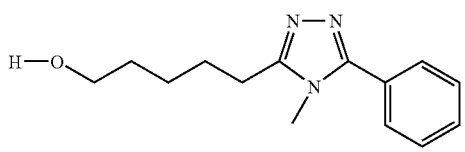

To a solution of 4-methyl-3-(4-penten-1-yl)-5-phenyl-4H-1,2,4-triazole (200 mg, 0.88 mmol) in THF (1 mL) was added 9-BBN (0.5M in THF, 1.76 mmol) and the solution was refluxed for 2 h. Two more portions of 9-BBN (0.88 mmol) were added, each after 1 h. The reaction mixture was cooled down at 0 C and was added NaOH (3M, 21Mmol) in one portion followed by dropwise addition of H₂O₂ (33% in water, 21Mmol). The mixture was stirred for another 2 h at r.t.

Solvent was evaporated in vacuo and the residue was taken in water and extracted with DCM. The organic layer was dried over Na₂SO₄, concentrated and purified by flash chromatography to give the title compound as light yellow oil (127 mg). MS (m/z): 246[MH]+.

Preparation 30

5-[4-methyl-5-(5-methyl-2-pyrazinyl)-4H-1,2,4-triazol-3-yl]-1-pentanol

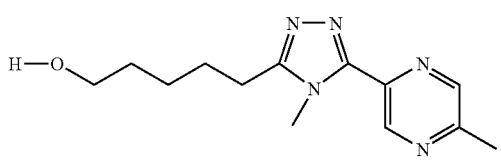

The title compound was prepared in analogy to the method described in Preparation 29 in 58 mg yield as a light yellow oil from 2-methyl-5-[4-methyl-5-(4-penten-1-yl)-4H-1,2,4-triazol-3-yl]pyrazine (80 mg). MS (m/z): 262[MH]+.

Preparation 31

5-(4-methyl-5-phenyl-4H-1,2,4-triazol-3-yl)pentyl methanesulfonate

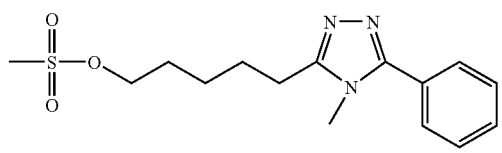

To a solution of 5-(4-methyl-5-phenyl-4H-1,2,4-triazol-3-yl)-1-pentanol (127 mg, 0.52 mmol) in DCM (5 ml) was added trietylamine (0.62 mmol) and methansulfonyl chloride (0.57 mmol). The solution was stirred at r.t. for 2 h and quenched with saturated NaHCO₃. The organic layer was dried over Na₂SO₄ and concentrated to give the title compound as light yellow oil (195 mg). MS (m/z): 324[MH]+.

Preparation 32

5-[4-methyl-5-(5-methyl-2-pyrazinyl)-4H-1,2,4-triazol-3-yl]pentyl methanesulfonate

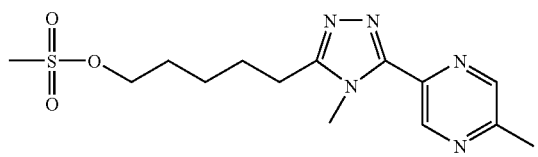

The title compound was prepared in analogy to the method described in Preparation 31 in 40 mg yield as a white oil from 5-[4-methyl-5-(5-methyl-2-pyrazinyl)-4H-1,2,4-triazol-3-yl]-1-pentanol (58 mg). MS (m/z): 339[MH]+.

Preparation 33

(1R,5S/1S,5R)-1-[6-(trifluoromethyl)-3-pyridinyl]-3-azabicyclo[3.1.0]hexane

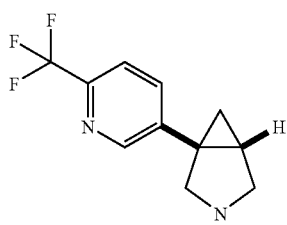

The title compound was prepared as reported in WO 2005/080382.

Preparation 34 ethyl 4-methyl-2-thioxo-2,3-dihydro-1,3-thiazole-5-carboxylate

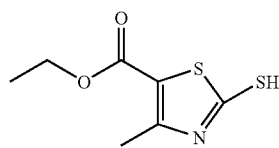

A solution of ethyl 2-chloroacetoacetate (5 g) and ammonium dithiocarbamate (3.37 g, prepared as reported in *Synthesis* (1985), (10), 948-9) in ethanol (20 mL) was refluxed overnight. The solvent was evaporated under vacuum and the crude product purified by flash chromatography on silica gel (eluting with cyclohexane:ethyl acetate from 1:0 to 7:3) to give the title compound (2.5 g). MS (m/z): 204 [MH]+.

Preparation 35 ethyl 4-methyl-1,3-thiazole-5-carboxylate

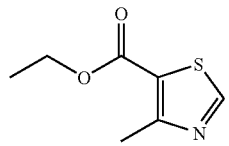

A solution of ethyl 4-methyl-2-thioxo-2,3-dihydro-1,3-thiazole-5-carboxylate (2.51 g) in HCl (37%, 8 mL) was warmed to 50° C., $H_2O_2$ (30%, 4.2 g) was added dropwise over 20 min and the reaction mixture was stirred for 1 h and allowed to reach room temperature. The mixture was then treated with $NaHCO_3$ up to a slightly basic pH and extracted twice with ether (2×20 mL), the organic phase separated and the solvent removed under reduced pressure. The crude product was purified by flash chromatography on silica gel (eluting with cyclohexane : ethyl acetate from 1:0 to 7:3) to give the title compound (0.5 g). MS (m/z): 172 [MH]+.

Preparation 36

4-methyl-1,3-thiazole-5-carbohydrazide

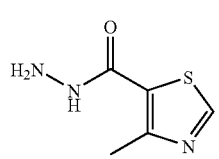

The title compound was prepared in analogy to Preparation 4 in 0.52 g yield starting from ethyl 4-methyl-1,3-thiazole-5-carboxylate (1.18 g). MS (m/z): 158 [MH]+.

Preparation 37

4-methyl-3-(4-methyl-1,3-thiazol-5-yl)-5-(4-penten-1-yl)-4H-1,2,4-triazole

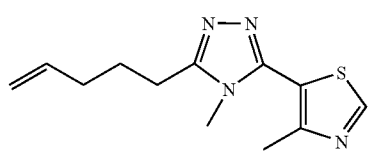

The title compound was prepared in analogy to Preparation 11 in 0.31 g yield starting from 2,4-dimethyl-thiazole-5-carboxylic acid hydrazide (0.52 g) and N,N'-dimethyl-5-hexenimidamide hydrochloride (0.58 g). MS (m/z): 249 [MH]+.

Preparation 38

3-(2,4-dimethyl-1,3-thiazol-5-yl)-4-methyl-5-(4-penten-1-yl)-4H-1,2,4-triazole

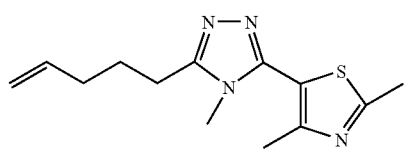

The title compound was prepared in analogy to Preparation 11 in 0.17 g yield starting from 2,4-dimethyl-1,3-thiazole-5-carbohydrazide (0.50 g) and N,N'-dimethyl-5-hexenimidamide hydrochloride (0.51 g). MS (m/z): 263 [MH]+.

Preparation 39

4-methyl-3-(4-penten-1-yl)-5-(phenylmethyl)-4H-1,2,4-triazole

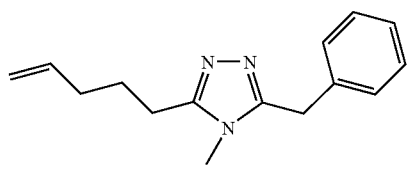

The title compound was prepared in analogy to Preparation 11 in 0.18 g yield starting from phenylacetic hydrazide (0.5 g) and N,N'-dimethyl-5-hexenimidamide hydrochloride (0.62 g). MS (m/z): 242 [MH]+.

Preparation 40

4-methyl-3-[4-(methyloxy)phenyl]-5-(4-penten-1-yl)-4H-1,2,4-triazole

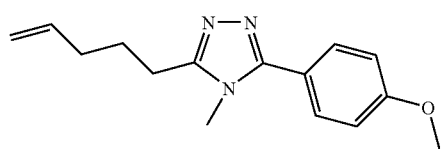

The title compound was prepared in analogy to Preparation 11 in 0.12 g yield starting from 4-methoxybenzhydrazide (0.5 g) and N,N'-dimethyl-5-hexenimidamide hydrochloride (0.48 g). MS (m/z): 258 [MH]+.

Preparation 41

3-(2,4-dichlorophenyl)-4-methyl-5-(4-penten-1-yl)-4H-1,2,4-triazole

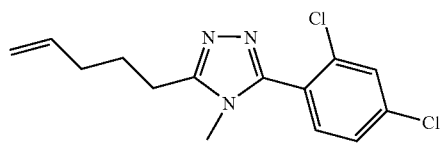

The title compound was prepared in analogy to Preparation 11 in 0.16 g yield starting from 2,4-dichlorobenzohydrazide (0.62 g) and N,N'-dimethyl-5-hexenimidamide hydrochloride (0.48 g). MS (m/z): 296 [MH]+.

Preparation 42

3-(3-chlorophenyl)-4-methyl-5-(4-penten-1-yl)-4H-1,2,4-triazole

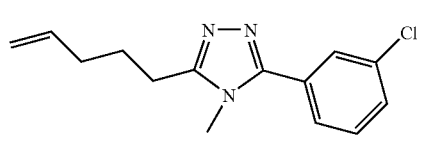

The title compound was prepared in analogy to Preparation 11 in 0.16 g yield starting from 3-chlorobenzhydrazide (0.52 g) and N,N'-dimethyl-5-hexenimidamide hydrochloride (0.48 g). MS (m/z): 262 [MH]+.

Preparation 43

3-(2-fluorophenyl)-4-methyl-5-(4-penten-1-yl)-4H-1,2,4-triazole

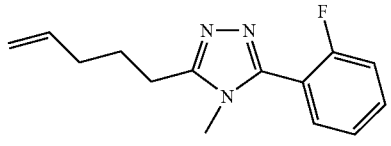

The title compound was prepared in analogy to Preparation 11 in 0.23 g yield starting from 2-fluorobenzoic hydrazide (0.44 g) and N,N'-dimethyl-5-hexenimidamide hydrochloride (0.50 g). MS (m/z): 245 [MH]+.

Preparation 44

4-[4-methyl-5-(4-methyl-1,3-thiazol-5-yl)-4H-1,2,4-triazol-3-yl]butanal

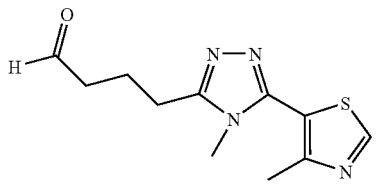

The title compound was prepared in analogy to Preparation 20 in 80 mg yield starting from 4-methyl-3-(4-methyl-1,3-thiazol-5-yl)-5-(4-penten-1-yl)-4H-1,2,4-triazole (0.1 g). MS (m/z): 251 [MH]+.

Preparation 45

4-[5-(2,4-dimethyl-1,3-thiazol-5-yl)-4-methyl-4H-1,2,4-triazol-3-yl]butanal

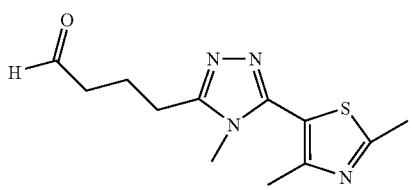

The title compound was prepared in analogy to Preparation 20 in 0.11 g yield starting from 3-(2,4-dimethyl-1,3-thiazol-5-yl)-4-methyl-5-(4-penten-1-yl)-4H-1,2,4-triazole (0.17g). MS (m/z): 264 [MH]+.

Preparation 46

4-{4-methyl-5-[4-(methyloxy)phenyl]-4H-1,2,4-triazol-3-yl}butanal

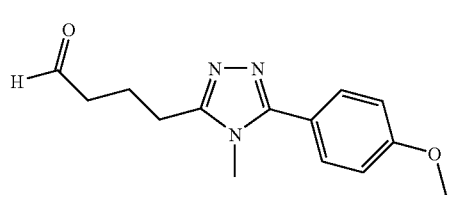

The title compound was prepared in analogy to Preparation 20 (OsO4 on resin was used, 80 mg) in 60 mg yield starting from 4-methyl-3-[4-(methyloxy)phenyl]-5-(4-penten-1-yl)-4H-1,2,4-triazole (0.12 g). MS (m/z): 260 [MH]+.

Preparation 47

4-[5-(2,4-dichlorophenyl)-4-methyl-4H-1,2,4-triazol-3-yl]butanal

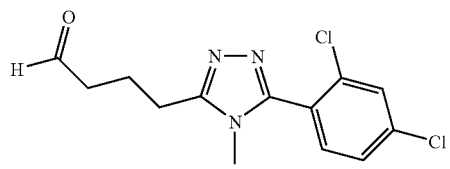

The title compound was prepared in analogy to Preparation 20 (OsO$_4$ on resin was used, 92 mg) in 68 mg yield starting from 3-(2,4-dichlorophenyl)-4-methyl-5-(4-penten-1-yl)-4H-1,2,4-triazole (0.16g). MS (m/z): 297 [MH]+.

Preparation 48

4-[5-(3-chlorophenyl)-4-methyl-4H-1,2,4-triazol-3-yl]butanal

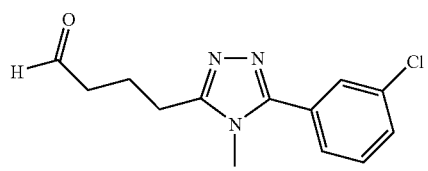

The title compound was prepared in analogy to Preparation 20 (OsO$_4$ on resin was used, 100 mg) in 60 mg yield starting from 3-(3-chlorophenyl)-4-methyl-5-(4-penten-1-yl)-4H-1,2,4-triazole (0. 16g). MS (m/z): 264 [MH]+.

Preparation 49

4-[5-(2-fluorophenyl)-4-methyl-4H-1,2,4-triazol-3-yl]butanal

The title compound was prepared in analogy to Preparation 20 (OsO$_4$ on resin was used, 100 mg) in 57 mg yield starting from 3-(2-fluorophenyl)-4-methyl-5-(4-penten-1-yl)-4H-1,2,4-triazole (0. 14g). MS (m/z): 247 [MH]+.

Preparation 50

4-[4-methyl-5-(phenylmethyl)-4H-1,2,4-triazol-3-yl]butanal

The title compound was prepared in analogy to Preparation 20 in 0.1 g yield starting from 4-methyl-3-(4-penten-1-yl)-5-(phenylmethyl)-4H-1,2,4-triazole (0.18 g). MS (m/z): 243 [MH]+.

Preparation 51

3-(1,1-dimethylethyl)-4-methyl-5-(4-penten-1-yl)-4H-1,2,4-triazole

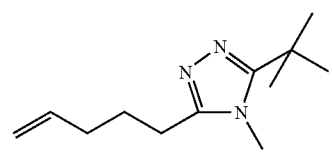

The title compound was prepared in analogy to Preparation 11 in 0.1 g yield as a white solid from N,N'-dimethyl-5- hexenimidamide hydrochloride (0.56 g) and 2,2-dimethyl-propanohydrazide (0.37 g). MS (m/z): 208[MH]⁺.

Preparation 52

4-[5-(1,1-dimethylethyl)-4-methyl-4H-1,2,4-triazol-3-yl]butanal

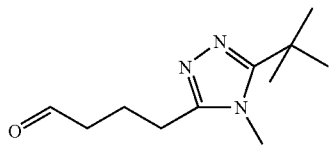

The title compound was prepared in analogy to Preparation 20 in 48 mg yield as an oil from 3-(1,1-dimethylethyl)-4-methyl-5-(4-penten-1-yl)-4H-1,2,4-triazole (0.1 g). MS (m/z): 210[MH]⁺.

Preparation 53

5-[5-(4-chlorophenyl)-4-methyl-4H-1,2,4-triazol-3-yl]-1-pentanol

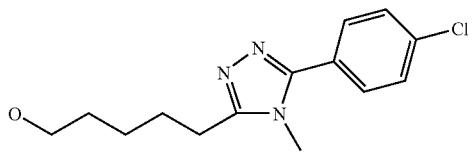

The title compound was prepared in analogy to the method described in Preparation 29 in 80 mg yield as an oil from 3-(4-chlorophenyl)-4-methyl-5-(4-penten-1-yl)-4H-1,2,4-triazole (190 mg). MS (m/z): 280[MH]⁺.

Preparation 54

5-[5-(4-chlorophenyl)-4-methyl-4H-1,2,4-triazol-3-yl]pentyl methanesulfonate

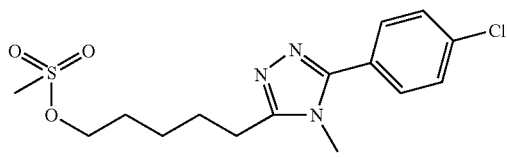

The title compound was prepared in analogy to the method described in Preparation 31 in 40 mg yield as an oil from 5-[5-(4-chlorophenyl)-4-methyl-4H-1,2,4-triazol-3-yl]-1-pentanol (40 mg). MS (m/z): 358[MH]⁺.

Preparation 55

2-methyl-3-[4-methyl-5-(4-penten-1-yl)-4H-1,2,4-triazol-3-yl]-6-(trifluoromethyl)pyridine

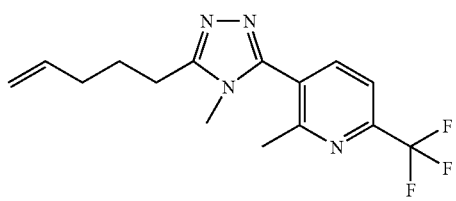

The title compound was prepared in analogy to Preparation 11 in 625 mg yield as a pale yellow gum from N,N'-dimethyl-5-hexenimidamide hydrochloride (500 mg).

MS (m/z): 311 [MH]+.

Preparation 56

4-{4-methyl-5-[2-methyl-6-(trifluoromethyl)-3-pyridinyl]-4H-1,2,4-triazol-3-yl}butanal

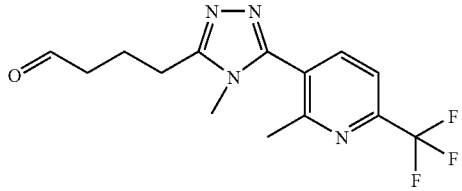

The title compound was prepared in analogy to the method described in Preparation 20 in 190 mg yield as an oil from 2-methyl-3-[4-methyl-5-(4-penten-1-yl)-4H-1,2,4-triazol-3-yl]-6-(trifluoromethyl)pyridine (156 mg). MS (m/z): 313[MH]+.

Preparation 57

4-methyl-3-[3-(methyloxy)phenyl]-5-(4-penten-1-yl)-4H-1,2,4-triazole

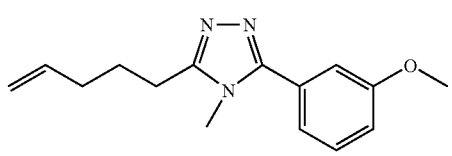

The title compound was prepared in analogy to the method described in Preparation 11 in 284 mg yield as a pale yellow gum from N,N'-dimethyl-5-hexenimidamide hydrochloride (470 mg). MS (m/z): 258[MH]+.

Preparation 58

4-{4-methyl-5-[3-(methyloxy)phenyl]-4H-1,2,4-triazol-3-yl}butanal

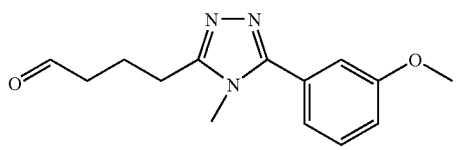

The title compound was prepared in analogy to the method described in Preparation 20 in 100 mg yield as an oil from 4-methyl-3-[3-(methyloxy)phenyl]-5-(4-penten-1-yl)-4H-1,2,4-triazole (100 mg). MS (m/z): 260[MH]+.

Preparation 59

4-methyl-3-[2-(methyloxy)phenyl]-5-(4-penten-1-yl)-4H-1,2,4-triazole

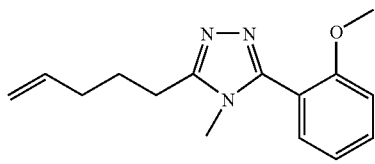

The title compound was prepared in analogy to the method described in Preparation 11 in 175 mg yield as a pale yellow gum from N,N'-dimethyl-5-hexenimidamide hydrochloride (470 mg). MS (m/z): 258[MH]+.

Preparation 60

4-{4-methyl-5-[2-(methyloxy)phenyl]-4H-1,2,4-triazol-3-yl}butanal

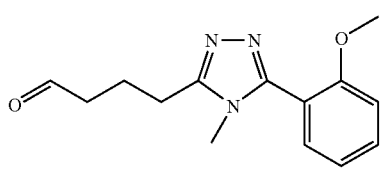

The title compound was prepared in analogy to the method described in Preparation 20 in 100 mg yield as an oil from 4-methyl-3-[3-(methyloxy)phenyl]-5-(4-penten-1-yl)-4H-1,2,4-triazole (100 mg). MS (m/z): 260[MH]+.

Preparation 61

3-(4-chlorophenyl)-4-methyl-5-(4-penten-1-yl)-4H-1,2,4-triazole

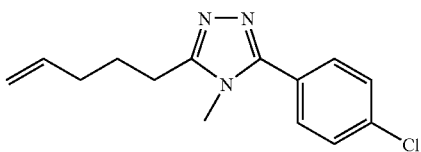

The title compound was prepared in analogy to the method described in Preparation 11 in 260 mg yield as a pale yellow gum from N,N'-dimethyl-5-hexenimidamide hydrochloride (500 mg). MS (m/z): 262[MH]+.

Preparation 62

4-{4-methyl-5-[2-(methyloxy)phenyl]-4H-1,2,4-triazol-3-yl}butanal

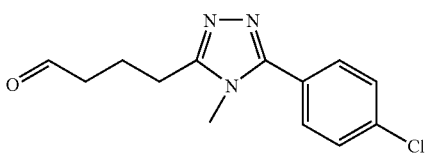

The title compound was prepared in analogy to the method described in Preparation 20 in 100 mg yield as an oil from 4-[5-(4-chlorophenyl)-4-methyl-4H-1,2,4-triazol-3-yl]butanal (100 mg). MS (m/z): 264[MH]+.

Preparation 63

3-[4-methyl-5-(4-penten-1-yl)-4H-1,2,4-triazol-3-yl]benzonitrile

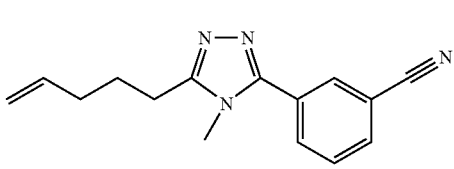

The title compound was prepared in analogy to the method described in Preparation 11 in 70 mg yield as a pale yellow gum from N,N'-dimethyl-5-hexenimidamide hydrochloride (220 mg). MS (m/z): 253[MH]+.

Preparation 64

3-[4-methyl-5-(4-oxobutyl)-4H-1,2,4-triazol-3-yl]benzonitrile

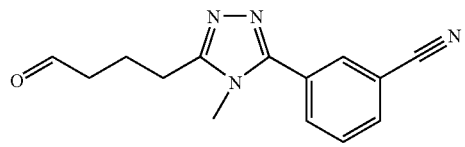

The title compound was prepared in analogy to the method described in Preparation 20 in 60 mg yield as an oil from 3-[4-methyl-5-(4-penten-1-yl)-4H-1,2,4-triazol-3-yl]benzonitrile (61 mg). MS (m/z): 255[MH]+.

Preparation 65

2-methyl-5-[4-methyl-5-(4-penten-1-yl)-4H-1,2,4-triazol-3-yl]quinoline

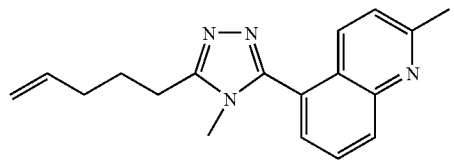

The title compound was prepared in analogy to the method described in Preparation 11 in 350 mg yield as a pale yellow gum from N,N'-dimethyl-5-hexenimidamide hydrochloride (368 mg). MS (m/z): 293[MH]+.

Preparation 66

4-[4-methyl-5-(2-methyl-5-quinolinyl)-4H-1,2,4-triazol-3-yl]butanal

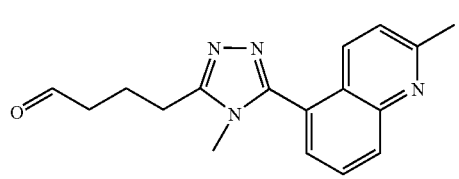

The title compound was prepared in analogy to the method described in Preparation 20 in 100 mg yield as an oil from 2-methyl-5-[4-methyl-5-(4-penten-1-yl)-4H-1,2,4-triazol-3-yl]quinoline (117 mg). MS (m/z): 295[MH]+.

Preparation 67

4-methyl-3-(4-penten-1-yl)-5-(1,3,5-trimethyl-1H-pyrazol4-yl)4H-1,2,4-triazole

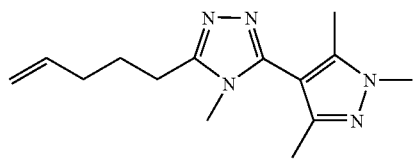

The title compound was prepared in analogy to the method described in Preparation 11 in 10 mg yield as a pale yellow gum from N,N'-dimethyl-5-hexenimidamide hydrochloride (42 mg). MS (m/z): 260[MH]+.

Preparation 68

4-[4-methyl-5-(1,3,5-trimethyl-1H-pyrazol4-yl)4H-1,2,4-triazol-3-yl]butanal

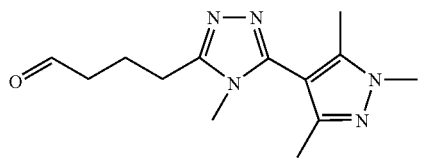

The title compound was prepared in analogy to the method described in Preparation 20 in 10 mg yield as an oil from 4-methyl-3-(4-penten-1-yl)-5-(1,3,5-trimethyl-1H-pyrazol-4-yl)-4H-1,2,4-triazole (10 mg). MS (m/z): 262[MH]+.

Preparation 69

4-[4-methyl-5-(4-penten-1-yl)4H-1,2,4-triazol-3-yl]benzonitrile

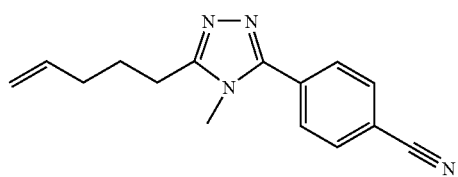

The title compound was prepared in analogy to the method described in Preparation 11 in 180 mg yield as a pale yellow gum from N,N'-dimethyl-5-hexenimidamide hydrochloride (565 mg). MS (m/z): 253[MH]+.

Preparation 70

4-[4-methyl-5-(4-oxobutyl)4H-1,2,4-triazol-3-yl]benzonitrile

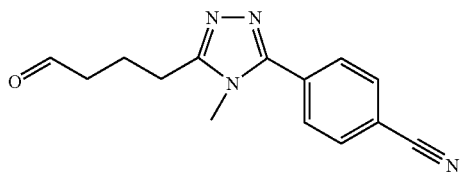

The title compound was prepared in analogy to the method described in Preparation 20 in 6 mg yield as an oil from 4-[4-methyl-5-(4-penten-1-yl)-4H-1,2,4-triazol-3-yl]benzonitrile (6.5 mg). MS (m/z): 255[MH]+.

Preparation 71 methyl 2,2-dimethyl-4-pentenoate

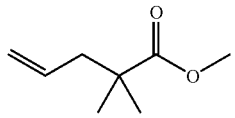

To a solution of diisopropilamide (7.6 ml) in THF (12 ml) was added drop by drop n-butil lithium (2.5M in hexane, 21.6 ml) at −78° C. After stirring the reaction mixture at −78° C. for 30 minutes, a solution of methyl isobutyrate (5 g) in THF (12 ml) was added in 10 minutes and the mixture stirred at −78° C. for 1 h. A solution of allyl bromide (4.7 ml) in THF (12 ml) was dropped into the mixture reaction and it was stirred at −78° C. for 1 h. After adding some drop of water, volatiles were evaporated in vacuo, the crude dissolved in ethyl acetate, washed with water and dried over Na$_2$SO$_4$. After filtration volatiles were evaporated in vacuo to give 1.8 g of the title compound as a yellow pale liquid, which was used without further purification.

Preparation 72

2,2-dimethyl-4-pentenohydrazide

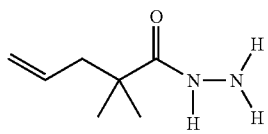

To a solution of methyl 2,2-dimethyl-4-pentenoate (1 g) in MeOH (2 ml) was added hydrazine monohydrate (2.7 ml). The solution was heated in a close microwave vial at 60° C. for 12 h. Volatiles were evaporated in vacuo to give 1 g of the title compound as a yellow pale foam, which was used without further purification.

Preparation 73

3-(1,1-dimethyl-3-buten-1-yl)-4-methyl-5-phenyl-4H-1,2,4-triazole

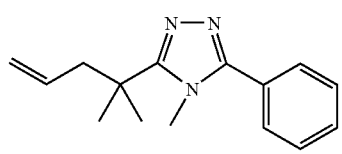

To a solution of 2,2-dimethyl-4-pentenohydrazide (360 mg) in NMP(2.5 ml) were added K$_2$CO$_3$ (348 mg) and N,N'-dimethylbenzenecarboximidamide hydrochloride (463 mmol). The solution was heated to the microwave at 240° C. for 30 minutes. Volatiles were evaporated in vacuo, the crude dissolved in DCM, washed with water and dried over Na$_2$SO$_4$. After filtration and concentration to dryness in vacuo, the crude was purified by column chromatography (DCM:MeOH=98 to 2) to give 196 mg of the title compound. MS (m/z): 242[MH]+.

Preparation 74

4-methyl-4-(4-methyl-5-phenyl-4H-1,2,4-triazol-3-yl)-1-pentanol

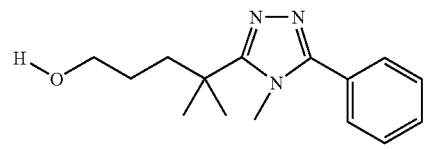

The title compound was prepared in analogy to the method described in Preparation 29 in 69 mg yield as a light yellow oil from 3-(1,1-dimethyl-3-buten-1-yl)-4-methyl-5-phenyl-4H-1,2,4-triazole (124 mg). MS (m/z): 260[MH]+.

Preparation 75

4-methyl-4-(4-methyl-5-phenyl-4H-1,2,4-triazol-3-yl)pentanal

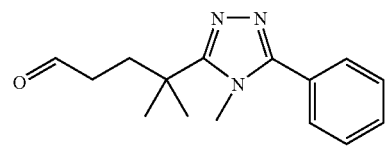

To a solution of 4-methyl-4-(4-methyl-5-phenyl-4H-1,2,4-triazol-3-yl)-1-pentanol (11 mg, 0.04 mmol) in DCM (0.5 ml) was added Dess Martin reagent (22 mg). The solution was stirred at r.t. for 2 h, then Na$_2$S$_2$O$_3$ (68 mg) was added and the mixture stirred for 30 minutes more. The mixture was diluted in DCM and washed with water. The organic phase was recovered and dried over Na₂SO₄. After filtration, volatiles were evaporated in vacuo to give 11 mg of the title compound as pale yellow oil, which was used without further purification. MS (m/z): 258[MH]+.

Preparation 76 ethyl 2,2-difluoro-5-hexenoate

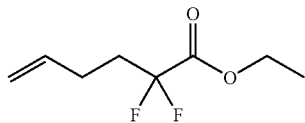

To a solution of ethyl 2-oxo-5-hexenoate (300 mg) in DCM (2 ml) was added DAST reagent (0.35 ml) at 0° C. and the reaction mixture was stirred at 0° C. for 3 h. Ice was added to the reaction and the product extracted with DCM. The organic phase was recovered and dried over Na₂SO₄. After filtration, volatiles were evaporated in vacuo to give 300 mg of the title compound as pale yellow oil, which was used without further purification.

Preparation 77

2,2-difluoro-5-hexenohydrazide

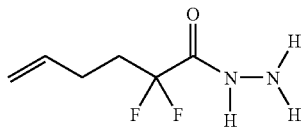

The title compound was prepared in analogy to the method described in Preparation 4 in 275 mg yield as a white slightly hygroscopic solid from ethyl 2,2-difluoro-5-hexenoate (300 mg).

Preparation 78

3-(1,1-difluoro-4-penten-1-yl)-4-methyl-5-phenyl-4H-1,2,4-triazole

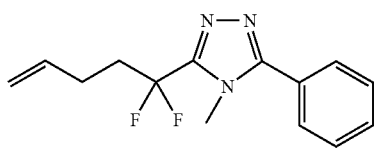

To a solution of 2,2-difluoro-5-hexenohydrazide (275 mg) in MeOH (8 ml) were added K₂CO₃ (232 mg) and N,N'-dimethylbenzenecarboximidamide hydrochloride (309 mmol). The solution was heated at reflux for 3 days. Volatiles were evaporated in vacuo and the crude was purified by column chromatography (DCM:MeOH=95 to 5) to give 45 mg of the title compound. MS (m/z): 264[MH]+.

Preparation 79

4,4-difluoro-4-(4-methyl-5-phenyl-4H-1,2,4-triazol-3-yl)butanal

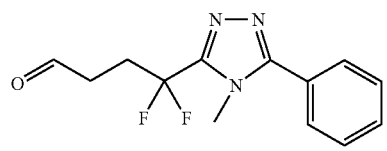

The title compound was prepared in analogy to the method described in Preparation 20 in 30 mg yield as a white slightly hygroscopic solid from 3-(1,1-difluoro-4-penten-1-yl)-4-methyl-5-phenyl-4H-1,2,4-triazole (45 mg). MS (m/z): 266 [MH]+.

Preparation 80

5-[4-methyl-5-(4-methyl-1,3-oxazol-5-yl)-4H-1,2,4-triazol-3-yl]-1-pentanol

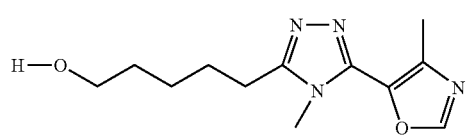

The title compound was prepared in analogy to the method described in Preparation 29 in 9 mg yield as a light yellow oil from 4-methyl-3-(4-methyl-1,3-oxazol-5-yl)-5-(4-penten-1-yl)-4H-1,2,4-triazole (60 mg). MS (m/z): 251 [MH]+.

Preparation 81

5-[4-methyl-5-(4-methyl-1,3-oxazol-5-yl)-4H-1,2,4-triazol-3-yl]pentyl methanesulfonate

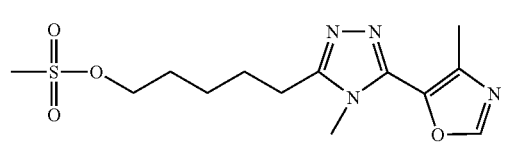

The title compound was prepared in analogy to the method described in Preparation 31 in 12 mg yield as a white oil from 5-[4-methyl-5-(4-methyl-1,3-oxazol-5-yl)-4H-1,2,4-triazol-3-yl]-1-pentanol (9 mg). MS (m/z): 329 [MH]+.

Preparation 82

5-{4-methyl-5-[3-(methyloxy)phenyl]-4H-1,2,4-triazol-3-yl}-1-pentanol

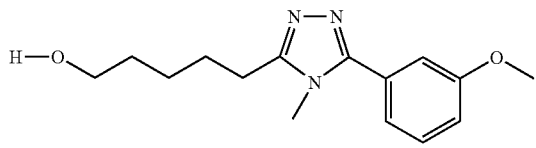

The title compound was prepared in analogy to the method described in Preparation 29 in 110 mg yield as a light yellow oil from 4-methyl-3-[3-(methyloxy)phenyl]-5-(4-penten-1-yl)-4H-1,2,4-triazole (184 mg). MS (m/z): 251[MH]+.

Preparation 83

5-{4-methyl-5-[3-(methyloxy)phenyl]-4H-1,2,4-triazol-3-yl}pentyl methanesulfonate

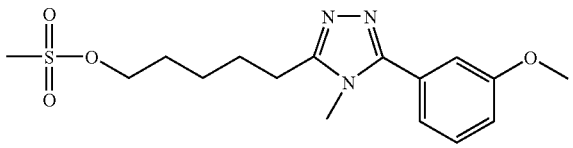

The title compound was prepared in analogy to the method described in Preparation 31 in 65 mg yield as a white oil from 5-{4-methyl-5-[3-(methyloxy)phenyl]-4H-1,2,4-triazol-3-yl}-1-pentanol (50 mg). MS (m/z): 354 [MH]+.

Preparation 84

5-[5-(3-chlorophenyl)-4-methyl-4H-1,2,4-triazol-3-yl]-1-pentanol

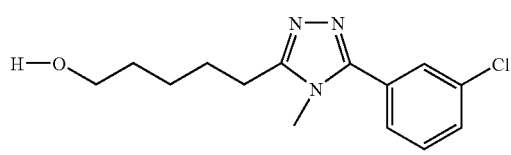

The title compound was prepared in analogy to the method described in Preparation 29 in 83 mg yield as a light yellow oil from 3-(3-chlorophenyl)-4-methyl-5-(4-penten-1-yl)-4H-1,2,4-triazole (117 mg). MS (m/z): 280 [MH]+.

Preparation 85

5-[5-(3-chlorophenyl)-4-methyl-4H-1,2,4-triazol-3-yl]pentyl methanesulfonate

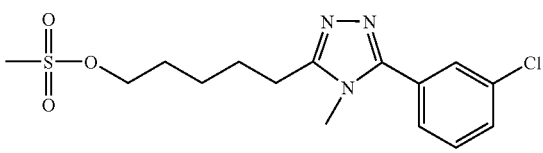

The title compound was prepared in analogy to the method described in Preparation 31 in 51 mg yield as a white oil from 5-[5-(3-chlorophenyl)-4-methyl-4H-1,2,4-triazol-3-yl]-1-pentanol (40 mg). MS (m/z)-358 [MH]+.

Preparation 86

3-(2-chlorophenyl)-4-methyl-5-(4-penten-1-yl)-4H-1,2,4-triazole

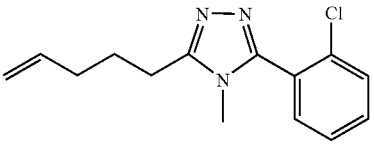

The title compound was prepared in 224 mg yield (30%) as a colourless oil from 2-chlorobenzohydrazide (485 mg) and N,N'-dimethyl-5-hexenimidamide hydrochloride (500 mg) in analogy to the method described in Preparation 11. MS (m/z): 262 [MH]+.

Preparation 87

4-[5-(2-chlorophenyl)-4-methyl-4H-1,2,4-triazol-3-yl]butanal

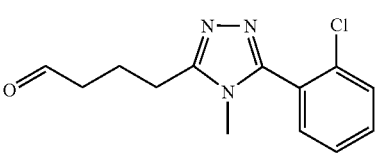

The title compound was prepared in 90 mg yield (83%) as a brown oil from 3-(2-chlorophenyl)-4-methyl-5-(4-penten- 1-yl)4H-1,2,4-triazole (108 mg) in analogy to the method described in Preparation 20. MS (m/z): 264 [MH]⁺.

Preparation 88 methyl 3-thiophenecarboxylate

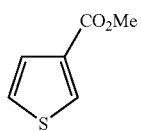

3-thiophenecarboxylic acid (2.0 g) was dissolved in MeOH (27 mL) and concentrated sulphuric acid (1.5 mL) was added. The reaction mixture was refluxed for 3 hours and 30 min., then concentrated under reduced pressure. A saturated NaHCO₃ solution was added and the mixture was extracted with ethyl acetate. The organic phase was dried over Na₂SO₄ and concentrated in vacuo to give 1.98 g of the title compound as a colourless liquid which was used without further purification.

NMR (¹H, CDCl₃): δ 8.12 (m, 1H), 7.55 (m, 1H), 7.33 (m, 1H), 3.88 (s, 3H).

Preparation 89

3-thiophenecarbohydrazide

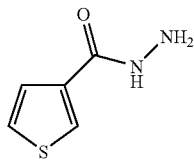

The title compound was prepared in 1.6 g yield as a pale yellow solid from methyl 3-thiophenecarboxylate (1.0 g) in analogy to the method described in Preparation 4 and used without further purification. MS (m/z): 143 [MH]⁺.

Preparation 90

4-methyl-3-(4-penten-1-yl)-5-(3-thienyl)-4H-1,2,4-triazole

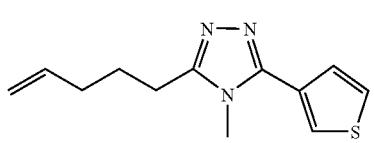

The title compound was prepared in 80 mg yield (12%) as a colourless oil from 3-thiophenecarbohydrazide (404 mg) and N,N'-Dimethyl-5-hexenimidamide hydrochloride (500 mg) in analogy to the method described in Preparation 11. MS(m/z): 234 [MH]⁺.

Preparation 91

4-[4-methyl-5-(3-thienyl)-4H-1,2,4-triazol-3-yl]butanal

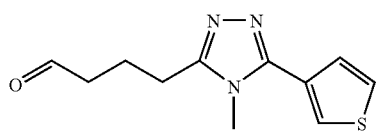

The title compound was prepared in 53 mg yield (68%) as a colourless oil from 4-methyl-3-(4-penten-1-yl)-5-(3-thienyl)-4H-1,2,4-triazole (77 mg) in analogy to the method described in Preparation 20. MS (m/z): 236 [MH]⁺.

Preparation 92

3-(2,4-difluorophenyl)-4-methyl-5-(4-penten-1-yl)-4H-1,2,4-triazole

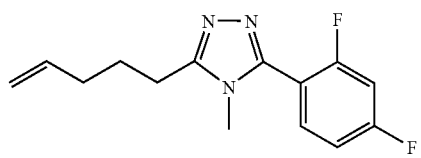

The title compound was prepared in 199 mg yield (26%) as a colourless oil from 2,4-difluorobenzohydrazide (504 mg) and N,N'-Dimethyl-5-hexenimidamide hydrochloride (520 mg) in analogy to the method described in Preparation 11. MS (m/z): 264 [MH]⁺.

Preparation 93

4-[5-(2,4-difluorophenyl)-4-methyl-4H-1,2,4-triazol-3-yl]butanal

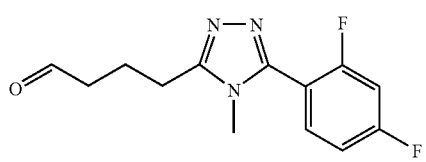

The title compound was prepared in 103 mg yield as a brown oil from 3-(2,4-difluorophenyl)-4-methyl-5-(4- penten-1-yl)-4H-1,2,4-triazole (100 mg) in analogy to the method described in Preparation 20. MS (m/z): 266 [MH]⁺.

Preparation 94

3,5-difluorobenzohydrazide

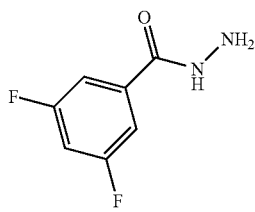

The title compound was prepared in 1.0 g yield as a white solid from 3,5-difluorobenzoic acid (1.0 g) in analogy to the method described in Preparation 4 and used without further purification. MS (m/z): 173 [MH]⁺.

Preparation 95

3-(3,5-difluorophenyl)-4-methyl-5-(4-penten-1-yl)-4H-1,2,4-triazole

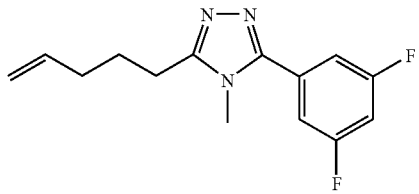

The title compound was prepared in 452 mg yield as a colourless oil from 3,5-difluorobenzohydrazide (482 mg) and N,N'-Dimethyl-5-hexenimidamide hydrochloride (500 mg) in analogy to the method described in Preparation 11. MS (m/z): 264 [MH]⁺.

Preparation 96

4-[5-(3,5-difluorophenyl)-4-methyl-4H-1,2,4-triazol-3-yl]butanal

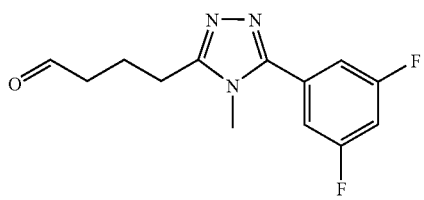

The title compound was prepared in 73 mg yield as a colourless oil from 3-(3,5-difluorophenyl)-4-methyl-5-(4-penten-1-yl)-4H-1,2,4-triazole (100 mg) in analogy to the method described in Preparation 20. MS (m/z): 266 [MH]⁺.

Preparation 97

1-methyl-1H-pyrrole-2-carbohydrazide

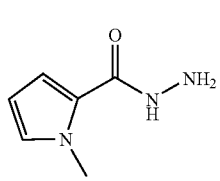

The title compound was prepared in 1.1 g yield as a white solid from methyl 1-methyl-1H-pyrrole-2-carboxylate (1.0 g) in analogy to the method described in Preparation 4 and used without further purification. MS (m/z): 140 [MH]⁺.

Preparation 98

4-methyl-3-(1-methyl-1H-pyrrol-2-yl)-5-(4-penten-1-yl)-4H-1,2,4-triazole

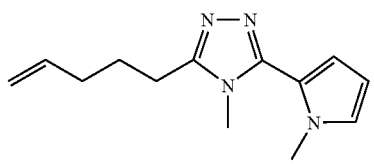

The title compound was prepared in 79 mg yield as a colourless oil from 1-methyl-1H-pyrrole-2-carbohydrazide (390 mg) and N,N'-Dimethyl-5-hexenimidamide hydrochloride (500 mg) in analogy to the method described in Preparation 11. MS (m/z): 231 [MH]⁺.

Preparation 99

4-[4-methyl-5-(1-methyl-1H-pyrrol-2-yl)-4H-1,2,4-triazol-3-yl]butanal

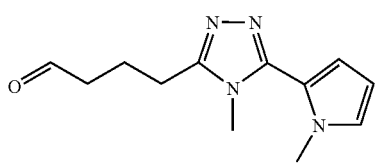

The title compound was prepared in 54 mg yield as a brown oil from 4-methyl-3-(1-methyl-1H-pyrrol-2-yl)-5-(4- penten-1-yl)-4H-1,2,4-triazole (79 mg) in analogy to the method described in Preparation 20. MS (m/z): 233 [MH]⁺.

Preparation 100

6-(methyloxy)-3-pyridinecarbohydrazide

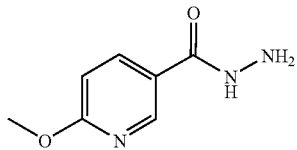

The title compound was prepared in 563 mg yield as a white solid from methyl 6-(methyloxy)-3-pyridinecarboxylate (1.0 g) in analogy to the method described in Preparation 4 and used without further purification. MS (m/z): 168 [MH]⁺.

Preparation 101

2-(methyloxy)-5-[4-methyl-5-(4-penten-1-yl)-4H-1,2,4-triazol-3-yl]pyridine

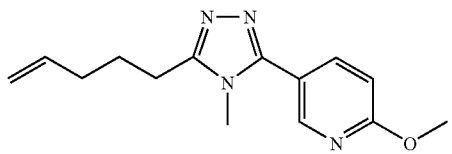

The title compound was prepared in 310 mg yield as a colourless oil from 6-(methyloxy)-3-pyridinecarbohydrazide (468 mg) and N,N'-Dimethyl-5-hexenimidamide hydrochloride (500 mg) in analogy to the method described in Preparation 11. MS (m/z): 259 [MH]⁺.

Preparation 102

4-{4-methyl-5-[6-(methyloxy)-3-pyridinyl]-4H-1,2,4-triazol-3-yl}butanal

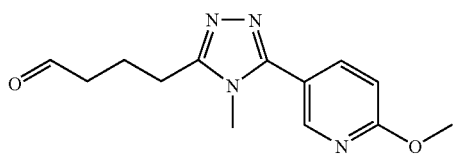

The title compound was prepared in 37 mg yield as a colourless oil from 2-(methyloxy)-5-[4-methyl-5-(4-penten-1-yl)-4H-1,2,4-triazol-3-yl]pyridine (100 mg) in analogy to the method described in Preparation 20 using polymer supported OsO₄ (loading 0.3 mmol/g, 63 mg) instead of aqueous OsO₄ and THF/1,2-dichloroethane/H₂O (3.5/1/1, 9.4 mL) instead of THF/H₂O. MS (m/z): 261 [MH]⁺.

Preparation 103

3-(4-fluorophenyl)-4-methyl-5-(4-penten-1-yl)-4H-1,2,4-triazole

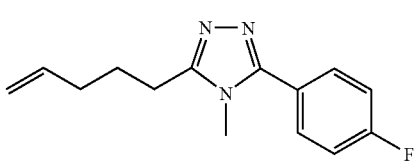

The title compound was prepared in 270 mg yield as a colourless oil from 4-fluorobenzohydrazide (437 mg) and N,N'-Dimethyl-5-hexenimidamide hydrochloride (500 mg) in analogy to the method described in Preparation 11. MS (m/z): 246 [MH]⁺.

Preparation 104

4-[5-(4-fluorophenyl)-4-methyl-4H-1,2,4-triazol-3-yl]butanal

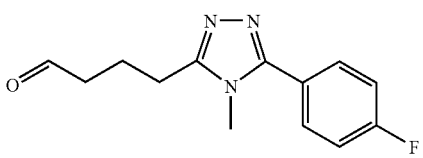

The title compound was prepared in 115 mg yield as a brown oil from 3-(4-fluorophenyl)-4-methyl-5-(4-penten-1-yl)-4H-1,2,4-triazole (141 mg) in analogy to the method described in Preparation 20. MS (m/z): 248 [MH]⁺.

Preparation 105

3-(3-fluorophenyl)-4-methyl-5-(4-penten-1-yl)-4H-1,2,4-triazole

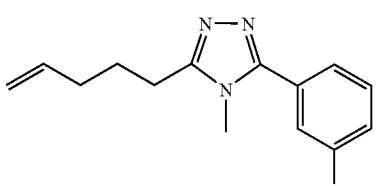

The title compound was prepared in 223 mg yield as a colourless oil from 3-fluorobenzohydrazide (431 mg) and N,N'-dimethyl-5-hexenimidamide hydrochloride (500 mg) in analogy to the method described in Preparation 11. MS (m/z): 246 [MH]+.

Preparation 106

4-[5-(3-fluorophenyl)-4-methyl-4H-1,2,4-triazol-3-yl]butanal

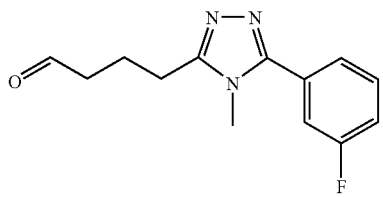

The title compound was prepared in 84 mg yield as a brown oil from 3-(3-fluorophenyl)-4-methyl-5-(4-penten-1-yl)-4H-1,2,4-triazole (100 mg) in analogy to the method described in Preparation 20. MS (m/z): 248 [MH]+.

Preparation 107

5-[5-(2,4-difluorophenyl)-4-methyl-4H-1,2,4-triazol-3-yl]-1-pentanol

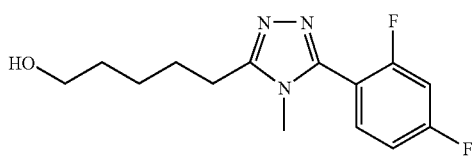

The title compound was prepared in 70 mg yield as a colourless oil from 3-(2,4-difluorophenyl)-4-methyl-5-(4-penten-1-yl)-4H-1,2,4-triazole (103 mg) in analogy to the method described in Preparation 29. MS (m/z): 282 [MH]+.

Preparation 108

4-[5-(2,4-difluorophenyl)-4-methyl-4H-1,2,4-triazol-3-yl]butyl methanesulfonate

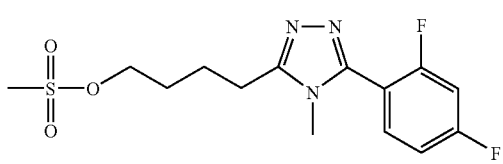

The title compound was prepared in 95 mg yield as a yellow oil from 5-[5-(2,4-difluorophenyl)-4-methyl-4H-1,2,4-triazol-3-yl]-1-pentanol (70 mg) in analogy to the method described in Preparation 31 and used without further purification.

MS (m/z): 360 [MH]+.

Preparation 109

5-(4-hydroxybutyl)-4-methyl-2,4-dihydro-3H-1,2,4-triazole-3-thione

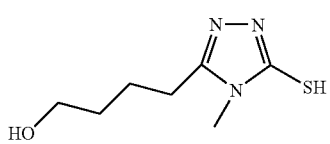

Tetrahydro-2H-pyran-2-one (2 ml), N-methylhydrazinecarbothioamide (3.4 g) and acetic acid (0.3 ml) were suspended in methanol (10 ml). The reaction was heated in microwave oven at 120° C. for 20' followed by further 10' at 110° C. Acetic acid was added (0.3 ml) and reaction was heated in a microwave oven at 140° C. for 20', further acetic acid (0.3 ml) was added and the reaction was in a microwave oven at 140° C. for 20'. The solvent was removed under reduced pressure, DCM was added to the crude and solid filtered-off. Solvent was removed under reduced pressure to give a crude product that was purified by flash chromatography on silica gel (DCM/MeOH from 0 to 10%) to give the title compound as a white solid (1 g).

NMR ($^1$H, DMSO-D$_6$): 6.2 (bs, 1H), 3.3 (m, 2H), 3.15 (m, 4H), 2.95 (d, 2H), 2.35 (t, 2H), 2.2 (m, 1H), 1.95 (t, 2H), 1.75 (d, 2H), 1.35 (m, 2H). MS (m/z): 266 [MH]+.

Preparation 110

4-[4-methyl-5-(methylthio)-4H-1,2,4-triazol-3-yl]-1-butanol

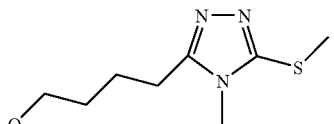

5-(4-hydroxybutyl)-4-methyl-2,4-dihydro-3H-1,2,4-triazole-3-thione (1 g) was dissolved in ethanol (6 ml), Iodomethane (0.4 ml) was added dropwise and the reaction was refluxed for 1 h. Dichloromethane and NaHCO$_3$ saturated solution were added. Solvent was removed under reduced to give a crude product that was purified by flash chromatography on silica gel (eluting with DCM/MeOH from 0 to 10%) to give the title compound (0.73 g).

NMR (¹H, CDCl3): 3.7 (t, 2H), 3.5 (sb, 3H), 2.8 (m, 2H), 2.7 (m, 3H), 1.9 (m, 2H), 1.7 (m, 2H). MS (m/z): 202 [MH]⁺.

Preparation 111

4-{5-[(cyclopropylmethyl)thio]-4-methyl-4H-1,2,4-triazol-3-yl}-1-butanol

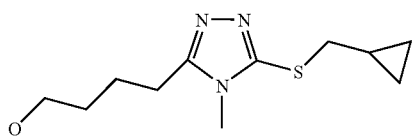

5-(4-hydroxybutyl)-4-methyl-2,4-dihydro-3H-1,2,4-triazole-3-thione (0.3 g), (bromomethyl)cyclopropane (0.17 ml) and triethyl ammine (0.27 ml) were dissolved in dimethylformamide (2 ml). Reaction was heated at 60° C. for 2 h. Dichloromethane and NaHCO₃ saturated solution were added. Solvent was removed, under reduced pressure to give a crude that was purified by Silica column (eluting with DCM/MeOH from 0 to 10%) to give the title compound (0.2 g).
NMR (¹H, CDCl3): 3.7 (t, 2H), 3.5 (s, 3H), 3.1 (d, 2H), 2.8 (d, 2H), 2.7 (m, 1H), 1.9 (m, 2H), 1.7 (m, 2H), 1.15 (m, 1H), 0.6 (m, 2H), 0.25 (sb, 2H). MS (m/z): 242 [MH]⁺.

Preparation 112

4-[4-methyl-5-(methylthio)-4H-1,2,4-triazol-3-yl]butanal

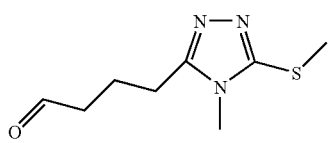

To a stirred solution of 4-[4-methyl-5-(methylthio)-4H-1,2,4-triazol-3-yl]-1-butanol (0.115 g) in dichloromethane (2 ml) Dess-Martin periodinane (0.24 g) was added at room temperature. After 1.5 h aqueous NaHCO₃ saturated solution (2 mL) was added to the reaction mixture, the organic phase extracted with DCM (6 mL) and the solvent removed under reduced pressure to give the title compound as an oil (40 mg) that was used in the following step as a such.
NMR (¹H, CDCl3): 9.8 (s, 1H), 3.45 (s, 3H), 2.8 (t, 2H), 2.7 (m, 5H), 2.1 (m, 2H). MS (m/z): 200 [MH]⁺.

Preparation 113

4-methyl-3-(4-penten-1-yl)-5-{4-[(trifluoromethyl)oxy]phenyl}-4H-1,2,4-triazole

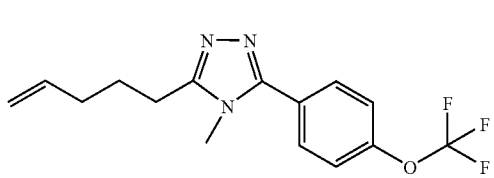

The title compound was prepared in analogy to the method described in Preparation 11 in 120 mg yield as a pale yellow gum from N,N'-dimethyl-5-hexenimidamide hydrochloride (400 mg). MS (m/z): 312[MH]+.

Preparation 114

4-(4-methyl-5-{4-[(trifluoromethyl)oxy]phenyl}-4H-1,2,4-triazol-3-yl)butanal

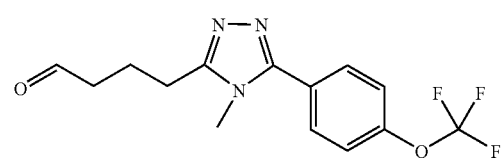

The title compound was prepared in analogy to the method described in Preparation 20 in 100 mg yield as a white oil from 4-methyl-3-(4-penten-1-yl)-5-{4-[(trifluoromethyl)oxy]phenyl}-4H-1,2,4-triazole (120 mg). MS (m/z): 314[MH]+.

Preparation 115

(1S,5R)-1-[2-fluoro-4-(trifluoromethyl)phenyl]-3-azabicyclo[3.1.0]hexane

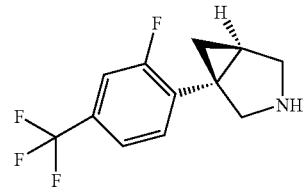

The title compound was prepared as reported in WO 2005/080382

Preparation 116

(1R,5S/1S,5R)-1-[5-(trifluoromethyl)-2-pyridinyl]-3-azabicyclo[3.1.0]hexane

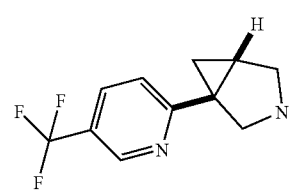

The title compound was prepared as reported in WO 2005/080382

Example 1

(1S,5R)-1-[2-fluoro-4-(trifluoromethyl)phenyl]-3-[4-(4-methyl-5-phenyl-4H-1,2,4-triazol-3-yl)butyl]-3-azabicyclo[3.1.0]hexane hydrochloride

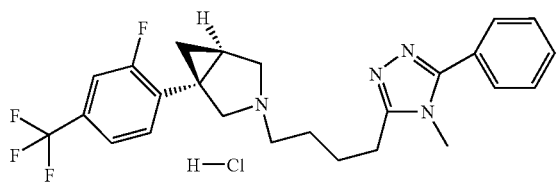

A mixture of (1S,5R)-1-[2-fluoro-4-(trifluoromethyl)phenyl]-3-azabicyclo[3.1.0]hexane (47 mg), 4-(4-methyl-5-phenyl-4H-1,2,4-triazol-3-yl)butanal (0.28 mmol), NaBH(OAc)$_3$ (0.38 mmol) and AcOH (0.28 mmol) in THF (anhydrous, 2 mL) was stirred at r.t. for 2 h. The organic phase was washed with NaOH 1N, dried over Na$_2$SO$_4$ and filtered. The filtrate was concentrated in vacuo and the crude was purified by column chromatography (eluting with dichloromethane/methanole 95/5) to give 38 mg of the free base of the title compound. To a solution of this material in dichloromethane (0.2 mL) was added 0.085 mmol of HCl (1M in Et$_2$O), the solvent evaporated under vacuum and the material thus obtained triturated with Et$_2$O to give 38 mg of the title compound as a white slightly hygroscopic solid.

NMR ($^1$H, CDCl$_3$): 7.73-7.70 (m, 2H), 7.67-7.60 (m, 4H), 7.57-7.52 (m, 2H), 4.1 (bd, 1H), 3.89 (bm, 1H), 3.62 (bm, 1H), 3.72 (s, 3H), 3.38 (t, 2H), 3..0 (t, 2H), 2.41 (m, 1H), 1.97 (m, 4H), 1.48 (m, 1H), 1.37 (m, 1H). MS (m/z): 459[MH]$^+$.

Example 2

(1R,5S/1S,5R)-3-[4-(4-methyl-5-phenyl-4H-1,2,4-triazol-3-yl)butyl]-1-[6-(trifluoromethyl)-3-pyridinyl]-3-azabicyclo[3.1.0]hexane hydrochloride

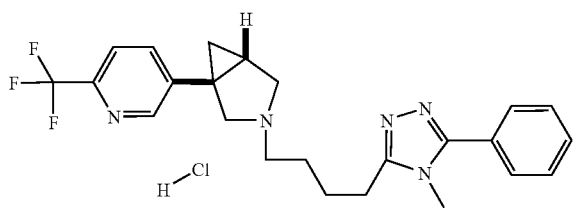

The title compound was prepared in analogy to the method described in Example 1 in 44 mg yield as a white slightly hygroscopic solid from (1R,5S)-1-[6-(trifluoromethyl)-3-pyridinyl]-3-azabicyclo[3.1.0]hexane (44mg).

NMR ($^1$H, CD$_3$OD): 8.701(s, 1H), 7.99 (d, 1H), 7.81 (d, 1H), 7.61 (t, 2H), 7.6 (d, 3H), 4.16 (bd, 1H), 3.86 (bd, 1H), 3.79 (db, 1H), 3.71 (bd, 1H), 3.68 (s, 3H), 3.38 (t, 2H), 2.97 (t, 2H), 2.46 (m, 1H), 1.97 (m, 4H), 1.48 (d, 2H). MS (m/z): 442[MH]$^+$.

Example 3

(1S,5R)-3-[4-(4-methyl-5-phenyl-4H-1,2,4-triazol-3-yl)butyl]-1-[4-(trifluoromethyl)phenyl]-3-azabicyclo[3.1.0]hexane hydrochloride

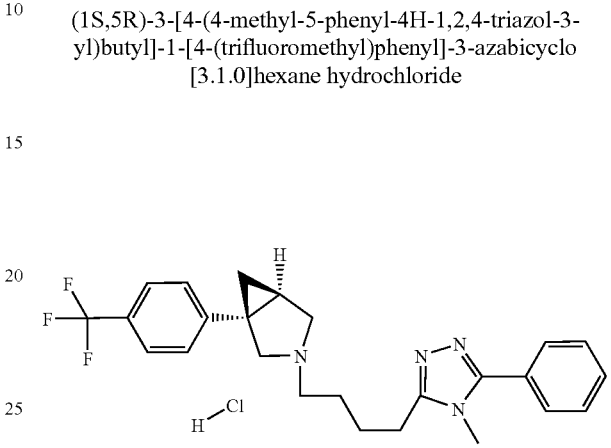

The title compound was prepared in analogy to the method described in Example 1 in 46 mg yield as a white slightly hygroscopic solid from (1S,5R)-1-(4-trifluorophenyl)-3-azabicyclo[3.1.0]hexane (36 mg).

NMR ($^1$H, CD$_3$OD): 7.58 (t, 2H), 7.57 (d, 2H), 7.52 (t,1H), 7.51 (d, 2H), 7.41 (d, 2H), 4.03 (bs, 1H), 3.74 (bs, 1H), 3.7-3.55 (bm, 2H), 3.59 (s, 3H), 3.27 (t, 2H), 2.88 (t, 2H), 2.25 (m, 1H), 1.87 (bm, 4H), 1.34 (t,1H), 1.29 (bt,1H). MS (m/z): 441 [MH]$^+$.

Example 4

(1S,5R)-3-{4-[4-methyl-5-(4-pyridazinyl)-4H-1,2,4-triazol-3-yl]butyl}-1-[4-(trifluoromethyl)phenyl]-3-azabicyclo[3.1.0]hexane hydrochloride

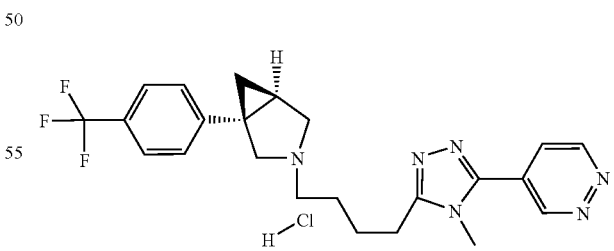

The title compound was prepared in analogy to the method described in Example 1 in 13.5 mg yield as a white slightly hygroscopic solid from (1S,5R)-1-(4-trifluorophenyl)-3-azabicyclo[3.1.0]hexane (36 mg).

NMR ($^1$H, CD$_3$OD): 9.67 (s, 1H), 9.51 (d, 1H), 8.23 (dd, 1H), 7.67 (d, 2H), 7.51 (d, 2H), 4.17 (d, 1H), 3.9 (s, 3H), 3.89

(d, 1H), 3.71 (d, 1H), 3.67 (d, 1H), 3.39 (bt, 2H), 3.12 (bt, 2H), 2.34 (bm, 1H), 1.99 (bs, 4H), 1.51 (bm, 1H), 1.36 (bm, 1H). MS (m/z): 443[MH]+.

Example 5

(1S,5R)-3-{4-[4-methyl-5-(2-methyl-3-pyridinyl)-4H-1,2,4-triazol-3-yl ]butyl}-1-[4-(trifluoromethyl)phenyl]-3-azabicyclo[3.1.0]hexane hydrochloride

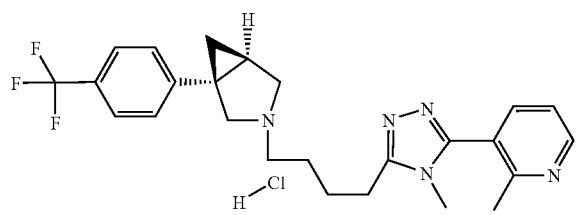

The title compound was prepared in analogy to the method described in Example 1 in 24 mg yield as a white slightly hygroscopic solid from (1S,5R)-1-(4-trifluorophenyl)-3-azabicyclo[3.1.0]hexane (52 mg).

NMR (¹H, CD₃OD): 8.68 (dd, 1H), 7.95 (dd, 1H), 7.68 (d, 2H), 7.54 (dd, 1H), 7.52 (d, 2H), 4.17 (m, 1H), 3.90 (m, 1H), 3.70 (m, 2H), 3.49 (s, 3H), 3.39 (t, 2H), 2.99 (t, 2H), 2.49 (s, 3H), 2.35 (m, 1H),1.97 (m, 4H), 1.42 (m, 2H). MS (m/z): 456[MH]+.

Example 6

(1S,5R)-3-{4-[4-methyl-5-(6-methyl-3-pyridinyl)-4H-1,2,4-triazol-3-yl]butyl}-1-[4-(trifluoromethyl)phenyl]-3-azabicyclo[3.1.0]hexane hydrochloride

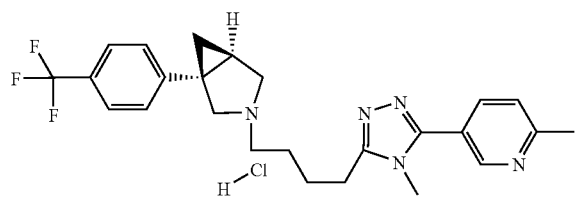

The title compound was prepared in analogy to the method described in Example 1 in 24 mg yield as a white slightly hygroscopic solid from (1S,5R)-1-(4-trifluorophenyl)-3-azabicyclo[3.1.0]hexane (52 mg).

NMR (¹H, CD₃OD): 8.83 (s, 1H), 8.24 (d, 1H), 7.69 (d, 1H), 7.67 (d, 2H), 7.51 (d, 2H), 4.16 (m, 1H), 3.88 (m, 1H), 3.74 (s, 3H), 3.71 (m, 2H), 3.38 (m, 2H), 3.01 (t, 2H), 2.71 (s, 3H), 2.35 (m, 1H),1.97 (m, 4H), 1.47 (m, 1H), 1.38 (m, 1H). MS (m/z): 456[MH]+.

Example 7

(1S,5R)-3-{4-[4-methyl-5-(5-methyl-2-pyrazinyl)-4H-1,2,4-triazol-3-yl]butyl}-1-[4-(trifluoromethyl)phenyl]-3-azabicyclo[3.1.0]hexane hydrochloride

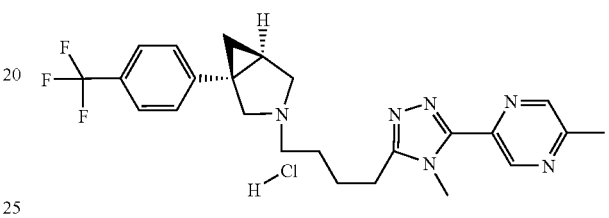

The title compound was prepared in analogy to the method described in Example 1 in 26 mg yield as a white slightly hygroscopic solid from (1S,5R)-1-(4-trifluorophenyl)-3-azabicyclo[3.1.0]hexane (52 mg).

NMR (¹H, CD₃OD): 9.17(m, 1H), 8.69 (m, 1H), 7.66 (d, 2H), 7.51 (d, 2H), 4.19 (m, 1H), 4.07 (m, 3H), 3.88 (m, 1H), 3.67 (m, 2H), 3.39 (m, 2H), 3.08 (m, 2H), 2.66 (m, 3H), 2.35 (m, 1H),1.96 (m, 4H), 1.49 (m, 1H), 1.34 (m, 1H). MS (m/z): 457MH]+.

Example 8

(1S,5R)-3-{4-[5-(2,4-dimethyl-1,3-oxazol-5-yl)-4-methyl-4H-1,2,4-triazol-3-yl]butyl}-1-[4-(trifluoromethyl)phenyl]-3-azabicyclo[3.1.0]hexane hydrochloride

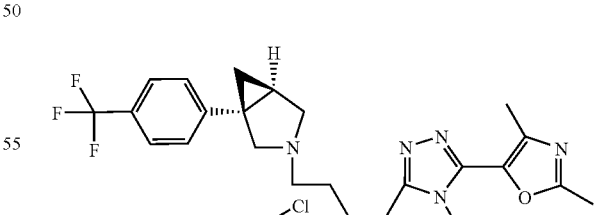

The title compound was prepared in analogy to the method described in Example 1 in 8 mg yield as a white slightly hygroscopic solid from (1S,5R)-1-(4-trifluorophenyl)-3-azabicyclo[3.1.0]hexane (19 mg).

NMR (¹H, CDCl₃): 7.66 (d, 2H), 7.49 (d, 2H), 4.05 (m, 1H), 3.76 (m, 1H), 3.74 (s, 3H), 3.60 (m, 2H), 3.29 (m, 2H), 2.94 (t, 2H), 2.53 (s, 3H), 2.34 (s, 3H), 2.28 (m, 1H), 1.92 (m, 4H), 1.46 (m, 1H), 1.32 (m, 1H). MS (m/z): 460[MH]⁺.

Example 9

(1R,5S/1S,5R )-3-[4-(4-methyl-5-phenyl-4H-1,2,4-triazol-3-yl)butyl]-1-[5-(trifluoromethyl)-2-pyridinyl]-3-azabicyclo[3.1.0]hexane dihydrochloride

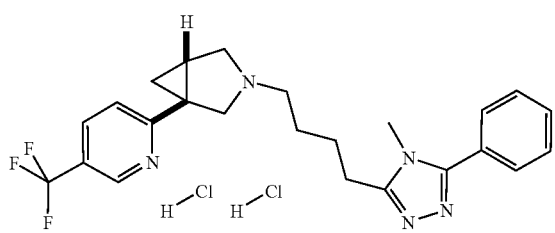

The title compound was prepared in analogy to the method described in Example 1 in 11 mg yield as a white slightly hygroscopic solid starting from (1R,5S/1S,5R )-1-[5-(trifluoromethyl)-2-pyridinyl]-3-azabicyclo[3.1.0]hexane (44 mg) and 4-(4-methyl-5-phenyl-4H-1,2,4-triazol-3-yl) butanal (66 mg).

NMR (¹H, Methanol-d⁴): δ 8.80 (s, 1H), 8.07 (dd, 1H), 7.80 (m, 3H), 7.72 (m, 2H), 7.43 (d, 1H), 4.20 (d, 1H), 4.08 (d, 1H), 3.91 (d, 1H), 3.85 (s, 3H), 3.62 (m, 1H), 3.42 (m, 2H), 3.14 (m, 2H), 2.52 (m, 1H), 2.03 (m, 4H), 1.67 (m, 2H). MS (m/z): 442 [MH]⁺.

Example 10

(1S,5R)-3-{4-[4-methyl-5-(2-methyl-1,3-thiazol-5-yl)-4H-1,2,4-triazol-3-yl ]butyl}-1-[4-(trifluoromethyl)phenyl]-3-azabicyclo[3.1.0]hexane hydrochloride

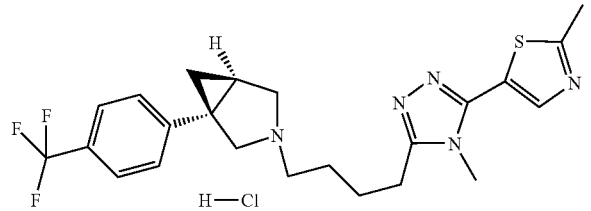

The title compound was prepared in analogy to the method described in Example 1 as a white slightly hygroscopic solid starting from (1S,5R)-1-[4-(trifluoromethyl)phenyl]-3-azabicyclo[3.1.0]hexane and 4-[4-methyl-5-(2-methyl-1,3-thiazol-5-yl)-4H-1,2,4-triazol-3-yl]butanal in 20% yield.

NMR (¹H, DMSO-d6): δ 10.52 (bs, 1H), 8.13 (s, 1H), 7.71 (d, 2H), 7.50 (d, 2H), 4.05 (m, 1H), 3.71 (s, 3H), 3.62 (m, 4H), 3.50 (m, 2H), 3.25 (m, 2H), 2.83 (t, 2H), 2.30 (m, 1H), 1.84 (m, 2H), 1.76 (m, 3H), 1.19 (m, 1H). MS (m/z): 462.0 [MH]⁺.

Example 11

(1R,5S/1S,5R)-3-{4-[5-(3,4-difluorophenyl)-4-methyl-4H-1,2,4-triazol-3-yl]butyl}-1-[6-(trifluoromethyl)-3-pyridinyl]-3-azabicyclo[3.1.0]hexane hydrochloride

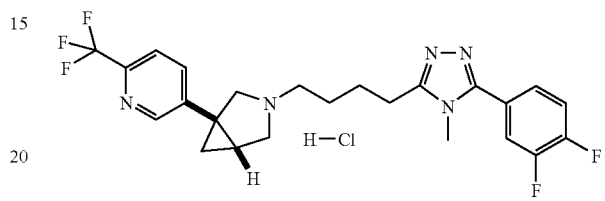

The title compound was prepared in analogy to the method described in Example 1 in 50 mg yield as a light brown solid from 4-[5-(3,4-difluorophenyl)-4-methyl-4H-1,2,4-triazol-3-yl]butanal (58 mg) and (1R,5S/1S,5R)-1-[6-(trifluoromethyl)-3-pyridinyl]-3-azabicyclo[3.1.0]hexane (50 mg).

NMR (¹H, DMSO): 10.6 (bs, 1H), 8.72 (s, 1H), 7.99 (d, 1H), 7.89 (d, 1H), 7.80 (td, 1H), 7.64 (dd, 1H), 7.56 (bm, 1H), 4.08 (bd, 1H), 3.73 (bd, 1H), 3.68 (bd, 1H), 3.61 (s, 3H), 3.52 (bd, 1H), 3.24 (t, 2H), 2.83 (t, 2H), 2.4 (m, 1H), 1.86 (m, 2H), 1.78 (m, 3H), 1.3 (bt, 1H). MS (m/z): 478[MH]⁺.

Example 12

(1S, 5R )-3-{4-[5-(3,4-difluorophenyl)-4-methyl-4H-1,2,4-triazol-3-yl]butyl}-1-[4-(trifluoromethyl)phenyl]-3-azabicyclo[3.1.0]hexane hydrochloride

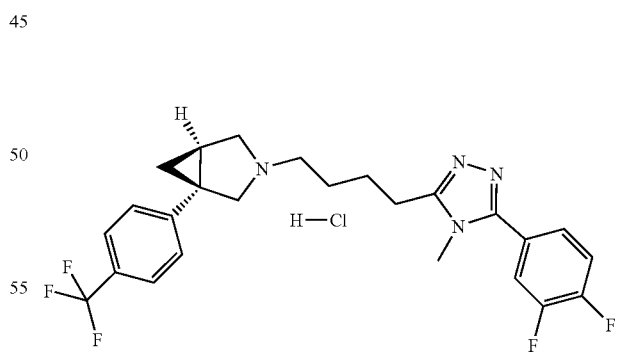

The title compound was prepared in analogy to the method described in Example 1 in 28 mg yield as a light brown solid from 4-[5-(3,4-difluorophenyl)-4-methyl-4H-1,2,4-triazol-3-yl]butanal (60 mg) and (1S,5R)-1-[4-(trifluoromethyl)phenyl]-3-azabicyclo[3.1.0]hexane (51 mg).

NMR (¹H, DMSO): 10.59 (bs, 1H), 7.81 (m, 1H), 7.71 (d, 2H), 7.65 (m, 1H), 7.57 (m, 1H), 7.50 (d, 2H), 4.06 (d, 1H), 3.74 (d, 1H), 3.62 (m, 3H), 3.43 (m, 2H), 3.25 (m, 2H), 2.84 (m, 2H), 2.30 (m, 1H), 1.84 (m, 5H), 1.19 (m, 1H). MS (m/z): 477[MH]+.

Example 13

(1S,5R)-3-{4-[4-methyl-5-(tetrahydro-2H-pyran-4-yl)-4H-1,2,4-triazol-3-yl]butyl}-1-[4-(trifluoromethyl)phenyl]-3-azabicyclo[3.1.0]hexane hydrochloride

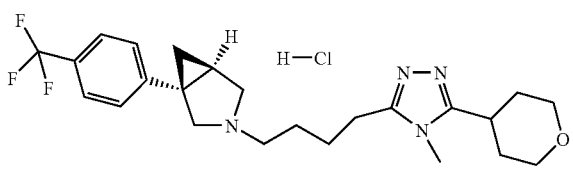

The title compound was prepared in analogy to the method described in Example 1 in 10 mg yield as a light brown solid from 4-[4-methyl-5-(tetrahydro-2H-pyran-4-yl)-4H-1,2,4-triazol-3-yl]butanal (35 mg) and (1S, 5R)-1-[4-(trifluoromethyl)phenyl]-3-azabicyclo[3.1.0]hexane (35 mg).

NMR (1H, DMSO): 10.69 (bs, 1H), 7.70 (d, 2H), 7.48 (d, 2H), 4.02 (bs, 1H), 3.92 (d, 2H), 3.66 (m, 4H), 3.47 (m, 2H), 3.35 (m, 5H), 2.84 (m, 2H), 2.29 (m, 1H), 1.78 (m, 9H), 1.21 (m, 1H). MS (m/z): 449[MH]+.

Example 14

(1S,5R)-3-[5-(4-methyl-5-phenyl-4H-1,2,4-triazol-3-yl)pentyl]-1-[4-(trifluoromethyl)phenyl]-3-azabicyclo[3.1.0]hexane hydrochloride

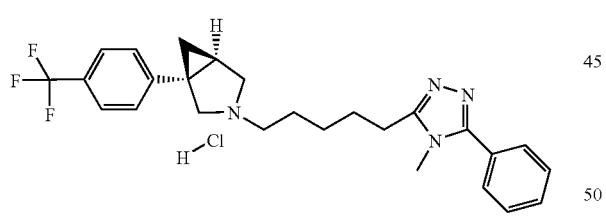

A mixture of (1S,5R)-1-[2-fluoro-4-(trifluoromethyl)phenyl]-3-azabicyclo[3.1.0]hexane (35 mg), 5-(4-methyl-5-phenyl-4H-1,2,4-triazol-3-yl)pentyl methanesulfonate (65 mg), K2CO3 (32 mg) and NaI (38 mg) in DMF (anhydrous, 0.3 mL) was stirred at 60° C. for 20 h. The reaction mixture was deposited on SCX column, washed with MeOH and the product eluted with NH3 (MeOH solution 2M). The collected ammonia methanolic solution was concentrated in vacuo and the crude was purified by column chromatography (eluting with dichloromethane/methanole 95/5) to give 50 mg of the free base of the title compound. To a solution of this material in dichloromethane (0.2 mL) was added 0.085 mmol of HCl (1M in Et2O), the solvent evaporated under vacuum and the material thus obtained triturated with Et2O to give 48 mg of the title compound as a white slightly hygroscopic solid.

NMR (1H, CD3OD): 7.69 (m, 4H), 7.56 (m, 3H), 7.49 (d, 2H), 4.03 (d, 1H), 3.70 (d, 1H), 3.61 (m, 1H), 3.61 (s, 3H), 3.49 (m, 1H), 3.17 (m, 2H), 2.82 (t, 2H), 2.28 (m, 1H), 1.77 (m, 6H), 1.44 (m, 1H), 1.18 (m, 1H). MS (m/z): 455[MH]+.

Example 15

(1S,5R)-3-{5-[4-methyl-5-(5-methyl-2-pyrazinyl)-4H-1,2,4-triazol-3-yl]pentyl}-1-[4-(trifluoromethyl)phenyl]-3-azabicyclo[3.1.0]hexane hydrochloride

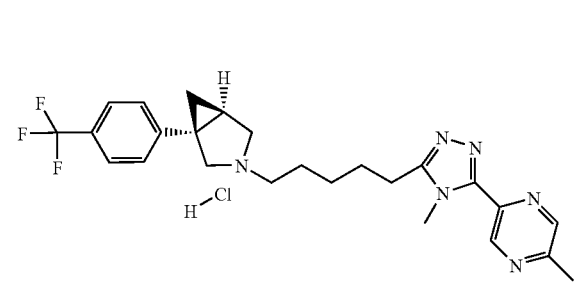

The title compound was prepared in analogy to the method described in Example 14 in 23 mg yield as a white slightly hygroscopic solid from (1S,5R)-1-(4-trifluorophenyl)-3-azabicyclo[3.1.0]hexane (27 mg) and 5-[4-methyl-5-(5-methyl-2-pyrazinyl)-4H-1,2,4-triazol-3-yl]pentyl methanesulfonate (40 mg).

NMR (1H, CD3OD): 9.14(m, 1H), 8.66 (m, 1H), 7.65 (d, 2H), 7.50 (d, 2H), 4.17 (d, 1H), 3.99 (m, 3H), 3.85 (d, 1H), 3.64 (m, 2H), 3.30 (m, 2H), 2.94 (t, 2H), 2.64 (m, 3H), 2.34 (bs, 1H),1.88 (m, 4H), 1.55 (m, 2H), 1.42 (m, 1H), 1.35 (m, 1H). MS (m/z): 455[MH]+.

Example 16

(1S,5R)-3-(4-{4-methyl-5-[4-(methyloxy)phenyl]-4H-1,2,4-triazol-3-yl}butyl)-1-[4-(trifluoromethyl)phenyl]-3-azabicyclo[3.1.0]hexane hydrochloride

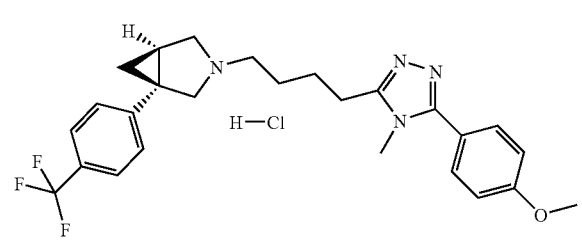

The title compound was prepared in analogy to the method described in Example 1 in 35 mg yield as a white slightly hygroscopic solid from (1S,5R)-1-(4-trifluorophenyl)-3-azabicyclo[3.1.0]hexane (40 mg) and 4-{4-methyl-5-[4-(methyloxy)phenyl]-4H-1,2,4-triazol-3-yl}butanal (60 mg)

MS (m/z): 471 [MH]+..

Example 17

(1S,5R)-3-{4-[5-(2,4-dichlorophenyl)-4-methyl-4H-1,2,4-triazol-3-yl]butyl}-1-[4-(trifluoromethyl)phenyl]-3-azabicyclo[3.1.0]hexane hydrochloride

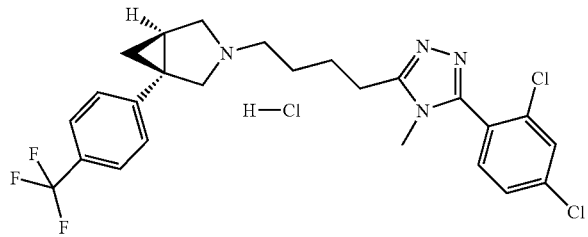

The title compound was prepared in analogy to the method described in Example 1 in 40 mg yield as a white slightly hygroscopic solid from (1S,5R)-1-(4-trifluorophenyl)-3-azabicyclo[3.1.0]hexane (40 mg) and 4-[5-(2,4-dichlorophenyl)-4-methyl-4H-1,2,4-triazol-3-yl]butanal (68mg).

MS (m/z): 509 [MH]+.

Example 18

(1S,5R)-3-{4-[5-(3-chlorophenyl)-4-methyl-4H-1,2,4-triazol-3-yl]butyl}-1-[4-(trifluoromethyl)phenyl]-3-azabicyclo[3.1.0]hexane hydrochloride

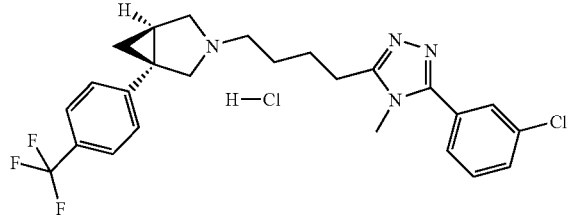

The title compound was prepared in analogy to the method described in Example 1 in 35 mg yield as a white slightly hygroscopic solid from (1S,5R)-1-(4-trifluorophenyl)-3-azabicyclo[3.1.0]hexane (40 mg) and 4-[5-(3-chlorophenyl)-4-methyl-4H-1,2,4-triazol-3-yl]butanal (60 mg).

NMR(1H, DMSO-D6): δ=1.19 (m, 1H), 1.73 (m, 1H), 1.79 (m, 2H), 1.89 (m, 2H), 2.29 (m, 1H), 2.85 (m, 2H), 3.26 (m, 2H), 3.42 (m, 2H), 3.63 (m, 4H), 3.71 (d, 1H), 4.02 (d, 1H), 7.49 (d, 2H), 7.63 (m, 3H), 7.70 (d, 2H), 7.76 (bs, 1H), 10.51 (bs,1H).

MS (m/z): 475 [MH]+.

Example 19

(1S,5R)-3-{4-[5-(2-fluorophenyl)-4-methyl-4H-1,2,4-triazol-3-yl]butyl}-1-[4-(trifluoromethyl)phenyl]-3-azabicyclo[3.1.0]hexane

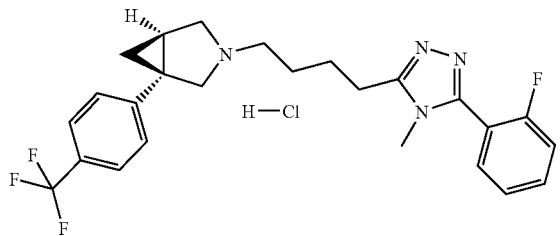

The title compound was prepared in analogy to the method described in Example 1 in 31 mg yield as a white slightly hygroscopic solid from (1S,5R)-1-(4-trifluorophenyl)-3-azabicyclo[3.1.0]hexane (40 mg) and 4-[5-(2-fluorophenyl)-4-methyl-4H-1,2,4-triazol-3-yl]butanal (58mg).

MS (m/z): 459 [MH]+.

Example 20

(1S,5R)-3-{4-[4-methyl-5-(4-methyl-1,3-thiazol-5-yl)-4H-1,2,4-triazol-3-yl]butyl}-1-[4-(trifluoromethyl)phenyl]-3-azabicyclo[3.1.0]hexane hydrochloride

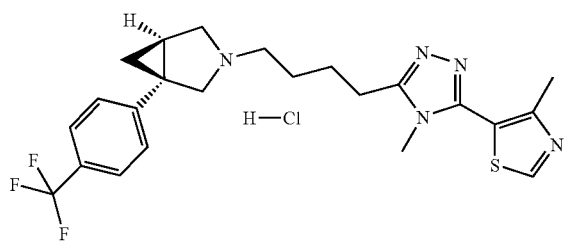

The title compound was prepared in analogy to the method described in Example 1 in 25 mg yield as a white slightly hygroscopic solid from (1S,5R)-1-(4-trifluorophenyl)-3-azabicyclo[3.1.0]hexane (87 mg) and 4-[4-methyl-5-(4-methyl-1,3-thiazol-5-yl)-4H-1,2,4-triazol-3-yl]butanal (80 mg).

NMR (1H, DMSO-D6) δ=1.20 (m, 1H), 1.69 (m, 1H), 1.83 (m, 4H), 2.29 (m, 1H), 2.40 (s, 3H), 2.82 (t, 2H), 3.24 (m, 2H), 3.41 (m, 1H), 3.49 (s, 3H), 3.63 (m, 1H), 3.71 (m, 1H), 4.05 (m, 1H), 7.49 (d, 2H), 7.70 (d, 2H), 9.27 (s, 1H), 10.38 (bs, 1H).

MS (m/z): 462 [MH]+.

Example 21

(1S,5R)-3-{4-[5-(2,4-dimethyl-1,3-thiazol-5-yl)-4-methyl-4H-1,2,4-triazol-3-yl]butyl}-1-[4-(trifluoromethyl)phenyl]-3-azabicyclo[3.1.0]hexane hydrochloride

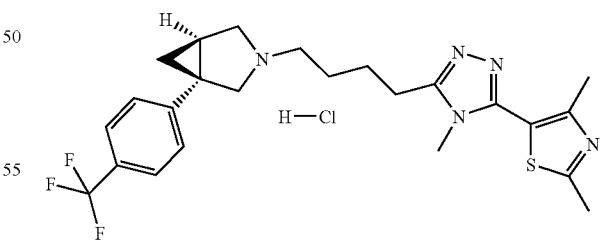

The title compound was prepared in analogy to the method described in Example 1 in 50 mg yield as a white slightly hygroscopic solid from (1S,5R)-1-(4-trifluorophenyl)-3-azabicyclo[3.1.0]hexane (80 mg) and 4-[5-(2,4-dimethyl-1,3-thiazol-5-yl)-4-methyl-4H-1,2,4-triazol-3-yl]butanal (104 mg).

NMR (1H, DMSO-D6) δ=1.19 (m, 1H), 1.70 (m, 1H), 1.83 (m, 4H), 2.29 (m, 1H), 2.30 (s, 3H), 2.68 (s, 3H), 2.81 (t, 2H), 3.24 (m, 2H), 3.49 (s, 3H), 3.50 (m,1H), 3.62 (m, 1H), 3.71 (m, 1H), 4.05 (m, 1H), 7.50 (d, 2H), 7.70 (d, 2H), 10.47 (bs, 1H).

MS (m/z): 476 [MH]+.

Example 22

(1S,5R)-3-{4-[4-methyl-5-(phenylmethyl)-4H-1,2,4-triazol-3-yl]butyl}-1-[4-(trifluoromethyl)phenyl]-3-azabicyclo[3.1.0]hexane hydrochloride

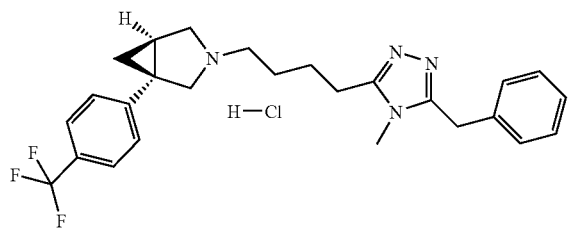

The title compound was prepared in analogy to the method described in Example 1 in 25 mg yield as a white slightly hygroscopic solid from (1S,5R)-1-(4-trifluorophenyl)-3-azabicyclo[3.1.0]hexane (50 mg) and 4-[4-methyl-5-(phenylmethyl)-4H-1,2,4-triazol-3-yl]butanal (60 mg).

MS (m/z): 455 [MH]+.

Example 23

(1S,5R)-3-{4-[5-(1,1-dimethylethyl)-4-methyl-4H-1,2,4-triazol-3-yl]butyl}-1-[4-(trifluoromethyl)phenyl]-3-azabicyclo[3.1.0]hexane hydrochloride

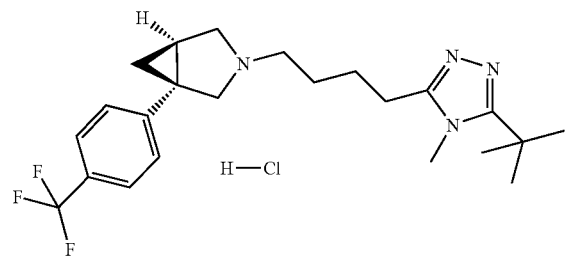

The title compound was prepared in analogy to the method described in Example 1 in 7 mg yield as a white solid starting from 4-[5-(1,1-dimethylethyl)-4-methyl-4H-1,2,4-triazol-3-yl]butanal (48 mg) and (1S,5R)-1-[4-(trifluoromethyl)phenyl]-3-azabicyclo[3.1.0]hexane (40 mg).

1H NMR (500 MHz, CD$_3$OD) δ ppm 7.67 (d, 2 H), 7.51 (d, 2 H) , 4.00-4.23 (m, 1 H), 3.91 (s, 3 H), 3.91 (s, 3 H), 3.91 (s, 3 H), 3.54-3.80 (m, 2 H), 3.34-3.42 (m, 2 H), 2.95-3.05 (m, 2 H), 2.28-2.42 (m, 1 H), 1.85-2.07 (m, 4 H), 1.48-1.59 (m, 10 H), 1.28-1.42 (m, 1 H). MS (m/z): 421[MH]+.

Example 24

(1S,5R)-3-{5-[5-(4-chlorophenyl)-4-methyl-4H-1,2,4-triazol-3-yl]pentyl}-1-[4-(trifluoromethyl)phenyl]-3-azabicyclo[3.1.0]hexane hydrochloride

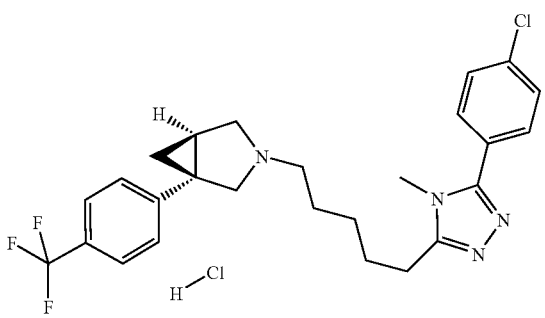

The title compound was prepared in analogy to the method described in Example 14 in 19 mg yield as a white solid starting from 5-[5-(4-chlorophenyl)-4-methyl-4H-1,2,4-triazol-3-yl]pentyl methanesulfonate (31 mg) and (1S,5R)-1-[4-(trifluoromethyl)phenyl]-3-azabicyclo[3.1.0]hexane (21 mg ).

1H NMR (500 MHz, CD$_3$OD): ppm 7.75 (d, 2 H), 7.67 (d, 4 H), 7.51 (d, 2 H), 4.16 (d, 1 H), 3.88 (d, 1 H), 3.76 (s, 3 H), 3.60-3.73 (m, 2 H), 3.27-3.42 (m, 2 H), 3.00 (t, 2 H), 2.28-2.40 (m, 1 H), 1.82-2.02 (m, 4 H), 1.56-1.66 (m, 2 H), 1.47-1.55 (m, 1 H), 1.31-1.40 (m, 1 H). MS: 489 [MH]+

Example 25

(1S,5R)-3-(4-{4-methyl-5-[2-methyl-6-(trifluoromethyl)-3-pyridinyl]-4H-1,2,4-triazol-3-yl}butyl)-1-[4-(trifluoromethyl)phenyl]-3-azabicyclo[3.1.0]hexane hydrochloride

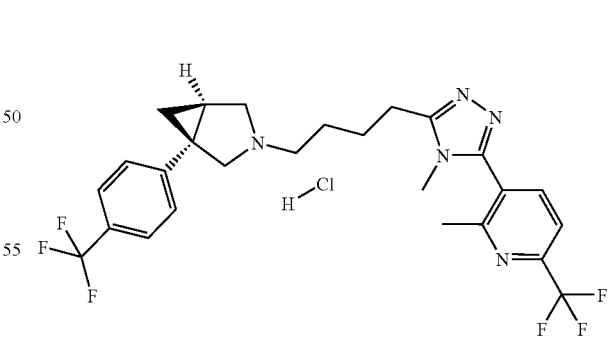

The title compound was prepared in analogy to the method described in Example 1 in 31 mg yield as a white slightly hygroscopic solid from (1S,5R)-1-(4-trifluorophenyl)-3-azabicyclo[3.1.0]hexane (35 mg).

NMR (DMSO-d$_6$) ppm 1.15-1.25 (m, 1 H) 1.67-1.73 (m, 1 H) 1.72-1.95 (m, 4 H) 2.23-2.35 (m, 1 H) 2.52 (s, 3 H) 2.78-2.94 (m, 2 H) 3.14-3.49 (m, 2 H) 3.43 (s, 3 H) 3.47-3.56

(m, 1 H) 3.59-3.68 (m, 1 H) 3.73 (d, 1 H) 4.07 (d, 1 H) 7.49 (d, 2 H) 7.70 (d, 2 H) 7.91 (d, 1 H) 8.13 (d, 1 H) 10.38 (br. s., 1 H). MS (m/z): 525 [MH]⁺.

Example 26

(1S,5R)-3-(4-{4-methyl-5-[3-(methyloxy)phenyl]-4H-1,2,4-triazol-3-yl}butyl)-1-[4-(trifluoromethyl)phenyl]-3-azabicyclo[3.1.0]hexane hydrochloride

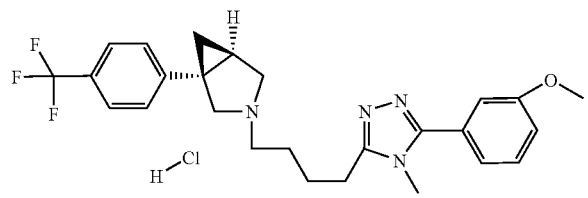

The title compound was prepared in analogy to the method described in Example 1 in 45 mg yield as a white slightly hygroscopic solid from (1S,5R)-1-(4-trifluorophenyl)-3-azabicyclo[3.1.0]hexane (35 mg).

NMR (¹H, METHANOL-d₄) ppm 1.32-1.43 (m, 1 H) 1.42-1.51 (m, 1 H) 1.89-2.05 (m, 4 H) 2.30-2.41 (m, 1 H) 2.97-3.06 (m, 2 H) 3.35-3.43 (m, 2 H) 3.60-3.79 (m, 2 H) 3.74 (s, 3 H) 3.79-3.98 (m, 1 H) 3.89 (s, 3 H) 4.03-4.28 (m, 1 H) 7.18-7.30 (m, 3 H) 7.48-7.60 (m, 3 H) 7.67 (d, 2 H). MS (m/z): 471 [MH]⁺.

Example 27

(1S,5R)-3-(4-{4-methyl-5-[2-(methyloxy)phenyl]-4H-1,2,4-triazol-3-yl}butyl)-1-[4-(trifluoromethyl)phenyl]-3-azabicyclo[3.1.0]hexane hydrochloride

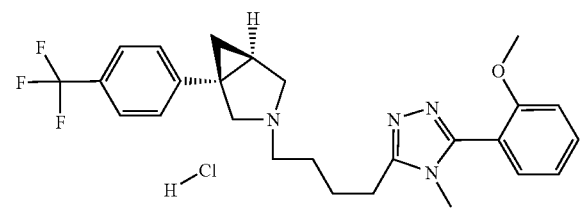

The title compound was prepared in analogy to the method described in Example 1 in 12 mg yield as a white slightly hygroscopic solid from (1S,5R)-1-(4-trifluorophenyl)-3-azabicyclo[3.1.0]hexane (35 mg).

NMR (¹H, METHANOL-d₄) ppm 1.33-1.44 (m, 1 H) 1.44-1.53 (m, 1 H) 1.88-2.08 (m, 4 H) 2.30-2.42 (m, 1 H) 2.94-3.07 (m, 2 H) 3.35-3.43 (m, 2 H) 3.56 (s, 3 H) 3.63-3.79 (m, 2 H) 3.80-3.91 (m, 1 H) 3.90 (s, 3 H) 4.01-4.27 (m, 1 H) 7.19 (t, 1 H) 7.27 (d, 1 H) 7.48 (d, 1 H) 7.53 (d, 2 H) 7.63-7.72 (m, 3 H). MS (m/z): 471 [MH]⁺.

Example 28

3-[4-methyl-5-(4-{(1S,5R)-1-[4-(trifluoromethyl)phenyl]-3-azabicyclo[3.1.0]hex-3-yl}butyl)-4H-1,2,4-triazol-3-yl]benzonitrile hydrochloride

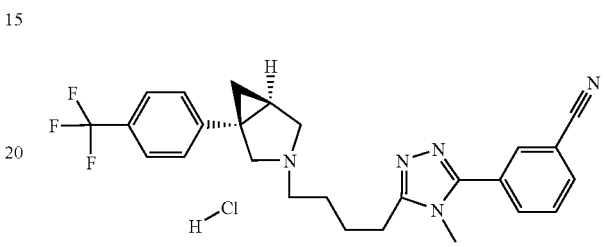

The title compound was prepared in analogy to the method described in Example 1 in 2.5 mg yield as a white slightly hygroscopic solid from (1S,5R)-1-(4-trifluorophenyl)-3-azabicyclo[3.1.0]hexane (39 mg).

NMR (¹H, CDCl3): ppm 1.47-2.03 (m, 7 H) 2.47-2.69 (m, 4 H) 2.77-2.92 (m, 2 H) 3.09-3.23 (m, 1 H) 3.35-3.47 (m, 1 H) 3.65 (s, 3 H) 7.23 (d, 2 H) 7.54 (d, 2 H) 7.67 (t, 1 H) 7.81 (d, 1 H) 7.90-7.99 (m, 2 H), acid proton not detected.

MS (m/z): 466[MH]⁺.

Example 29

2-methyl-5-[4-methyl-5-(4-{(1S,5R)-1-[4-(trifluoromethyl)phenyl]-3-azabicyclo[3.1.0]hex-3-yl}butyl)-4H-1,2,4-triazol-3-yl]quinoline hydrochloride

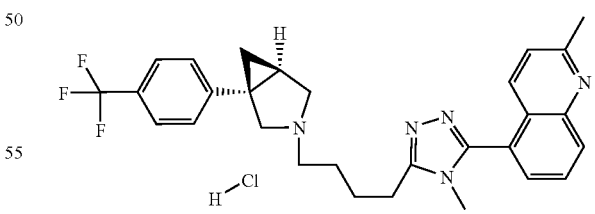

The title compound was prepared in analogy to the method described in Example 1 in 32 mg yield as a white slightly hygroscopic solid from (1S,5R)-1-(4-trifluorophenyl)-3-azabicyclo[3.1.0]hexane (36 mg).

NMR (¹H, CD₃OD) ppm 1.35-1.54 (m, 2 H) 1.92-2.11 (m, 4 H) 2.29-2.45 (m, 1 H) 2.84 (s, 3 H) 3.03 (t, 2 H) 3.41 (t, 2 H) 3.53 (s, 3 H) 3.61-3.83 (m, 2 H) 3.81-4.00 (m, 1 H) 4.07-4.28

(m, 1 H) 7.53 (d, 2 H) 7.64 (d, 1 H) 7.68 (d, 2 H) 7.84 (d, 1 H) 8.02 (t, 1 H) 8.25 (d, 1 H) 8.32 (d, 1 H). MS (m/z): 506 [MH]⁺.

Example 30

(1S,5R)-3-{4-[4-methyl-5-(1,3,5-trimethyl-1H-pyrazol-4-yl)-4H-1,2,4-triazol-3-yl]butyl}-1-[4-(trifluoromethyl)phenyl]-3-azabicyclo[3.1.0]hexane hydrochloride

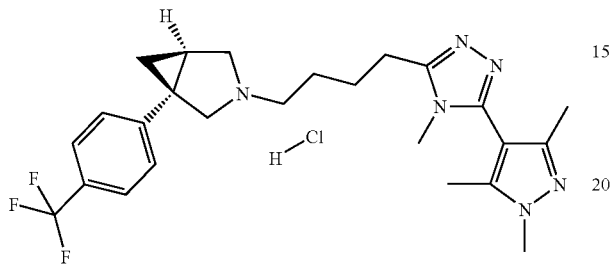

The title compound was prepared in analogy to the method described in Example 1 in 8.5 mg yield as a white slightly hygroscopic solid from (1S,5R)-1-(4-trifluorophenyl)-3-azabicyclo[3.1.0]hexane (9 mg).

NMR (¹H, CD₃OD) ppm 1.34-1.44 (m, 1 H) 1.42-1.53 (m, 1 H) 1.92-2.04 (m, 4 H) 2.17 (s, 3 H) 2.26 (s, 3 H) 2.32-2.38 (m, 1 H) 2.99 (t, 2 H) 3.39 (t, 2 H) 3.57 (s, 3 H) 3.64-3.79 (m, 2 H) 3.80-3.91 (m, 1 H) 3.82 (s, 3 H) 4.04-4.25 (m, 1 H) 7.52 (d, 2 H) 7.67 (d, 2 H). MS (m/z): 473 [MH]⁺.

Example 31

4-[4-methyl-5-(4-{(1S,5R)-1-[4-(trifluoromethyl)phenyl]-3-azabicyclo[3.1.0]hex-3-yl}butyl)-4H-1,2,4-triazol-3-yl]benzonitrile hydrochloride

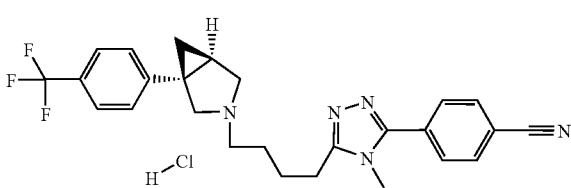

The title compound was prepared in analogy to the method described in Example 1 in 7.5 mg yield as a white slightly hygroscopic solid from (1S,5R)-1-(4-trifluorophenyl)-3-azabicyclo[3.1.0]hexane (7 mg).

NMR (¹H, CD₃OD) ppm 1.23-1.42 (m, 2 H) 1.76-1.96 (m, 4 H) 2.20-2.30 (m, 1 H) 2.88 (t, 2 H) 3.27 (t, 2 H) 3.49-3.70 (m, 2 H) 3.61 (s, 3 H) 3.70-3.84 (m, 1 H) 3.96-4.18 (m, 1 H) 7.41 (d, 2 H) 7.57 (d, 2 H) 7.79 (d, 2 H) 7.86 (d, 2 H).

MS (m/z): 466 [MH]⁺.

Example 32

(1S,5R)-3-[4-methyl-4-(4-methyl-5-phenyl-4H-1,2,4-triazol-3-yl)pentyl]-1-[4-(trifluoromethyl)phenyl]-3-azabicyclo[3.1.0]hexane hydrochloride

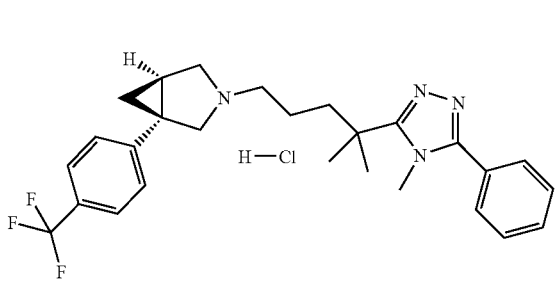

The title compound was prepared in analogy to the method described in Example 1 in 2 mg yield as a white slightly hygroscopic solid from (1S,5R)-1-(4-trifluorophenyl)-3-azabicyclo[3.1.0]hexane (10 mg).

NMR (¹H, CD₃OD) ppm 1.26-1.35 (m, 1 H) 1.51-1.61 (m, 1 H) 1.61 (s, 6 H) 1.74-1.88 (m, 2 H) 1.92-2.02 (m, 2 H) 2.24-2.38 (m, 1 H) 3.23-3.36 (m, 2 H) 3.57-3.65 (m, 1 H) 3.65-3.74 (m, 1 H) 3.78-3.89 (m, 1 H) 3.92 (s, 3 H) 4.07-4.20 (m, 1 H) 7.45-7.55 (m, 2 H) 7.63-7.74 (m, 5 H) 7.74-7.82 (m, 2 H). MS (m/z): 469 [MH]⁺.

Example 33

(1S,5R)-3-[4,4-difluoro-4-(4-methyl-5-phenyl-4H-1,2,4-triazol-3-yl)butyl]-1-[4-(trifluoromethyl)phenyl]-3-azabicyclo[3.1.0]hexane hydrochloride

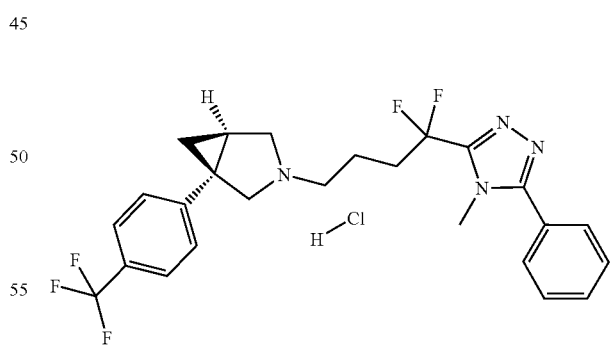

The title compound was prepared in analogy to the method described in Example 1 in 30 mg yield as a white slightly hygroscopic solid from (1S,5R)-1-(4-trifluorophenyl)-3-azabicyclo[3.1.0]hexane (25 mg).

NMR (¹H, CD₃OD) ppm 1.17-1.32 (m, 1 H) 1.55-1.69 (m, 1 H) 2.02-2.21 (m, 2 H) 2.26-2.35 (m, 1 H) 2.58-2.77 (m, 2 H) 3.23-3.43 (m, 2 H) 3.50-3.61 (m, 1 H) 3.64-3.73 (m, 1 H)

3.74-3.83 (m, 1 H) 3.79 (s, 3 H) 4.11 (dd, 1 H) 7.49 (d, 2 H) 7.57-7.65 (m, 3 H) 7.70 (d, 2 H) 7.75 (d, 2 H) 10.31 (br. s., 1 H). MS (m/z): 477 [MH]+.

Example 34

(1S,5R)-3-{4-[5-(3-fluorophenyl)-4-methyl-4H-1,2,4-triazol-3-yl]butyl}-1-[4-(trifluoromethyl)phenyl]-3-azabicyclo[3.1.0]hexane hydrochloride

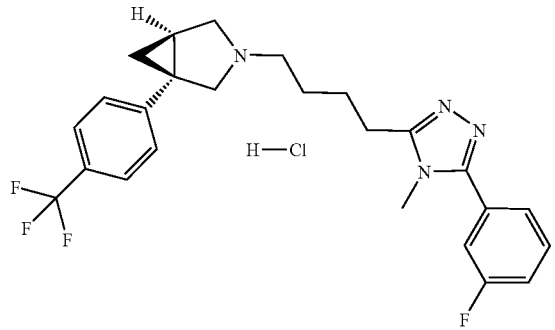

The title compound was prepared in 51 mg yield as a brown slightly hygroscopic solid from 4-[5-(3-fluorophenyl)-4-methyl-4H-1,2,4-triazol-3-yl]butanal (46 mg) and (1S,5R)-1-[4-(trifluoromethyl)phenyl]-3-azabicyclo[3.1.0]hexane (42 mg) in analogy to the method described in Example 1.

NMR ($^1$H, DMSO-D6): δ=1.16-1.31 (m, 1H), 1.65-1.76 (m, 1H), 1.74-2.00 (m, 4H), 2.24-2.40 (m,1H), 2.85 (t, 2H), 3.20-3.34 (m, 2H), 3.46-3.59 (m, 1H), 3.57-3.83 (m, 2H), 3.64 (s,3H), 3.97-4.22 (m, 1H), 7.42 (td, 1H), 7.48-7.68 (m, 3H), 7.52-7.59 (m, 2H), 7.73 (d, 2H), 10.40 (bs, 1H). MS (m/z): 459 [MH]+.

Example 35

(1S,5R)-3-{4-[5-(2-chlorophenyl)-4-methyl-4H-1,2,4-triazol-3-yl]butyl}-1-[4-(trifluoromethyl)phenyl]-3-azabicyclo[3.1.0]hexane hydrochloride

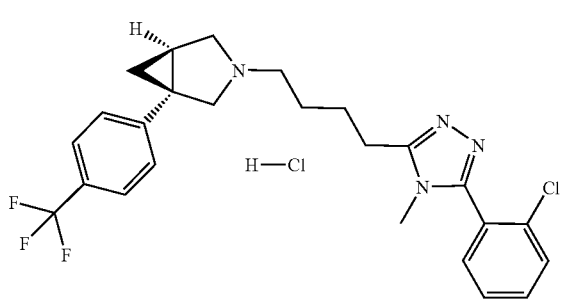

The title compound was prepared in 27 mg yield (31%) as a white slightly hygroscopic solid from 4-[5-(2-chlorophenyl)-4-methyl-4H-1,2,4-triazol-3-yl]butanal (45 mg) and (1S,5R)-1-[4-(trifluoromethyl)phenyl]-3-azabicyclo[3.1.0]hexane (38 mg) in analogy to the method described in Example 1.

NMR ($^1$H, DMSO-D6) δ=1.09-1.30 (m, 1H), 1.60-1.70 (m, 1H), 1.72-1.93 (m, 4H), 2.26-2.34 (m, 1H), 2.75-2.87 (m, 2H), 3.19-3.38 (m, 2H), 3.37 (s, 3H), 3.46-3.56 (m, 1H), 3.58-3.67 (m, 1H), 3.68-3.78 (m, 1H), 3.94-4.14 (m, 1H), 7.42-7.54 (m, 4H), 7.57-7.65 (m, 1H), 7.64-7.76 (m, 3H), 10.26 (bs, 1H). MS (m/z): 475 [MH]+.

Example 36

(1S,5R)-3-{4-[4-methyl-5-(3-thienyl)-4H-1,2,4-triazol-3-yl]butyl}-1-[4-(trifluoromethyl)phenyl]-3-azabicyclo[3.1.0]hexane hydrochloride

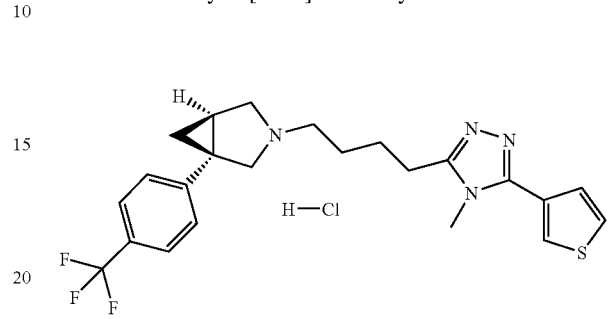

The title compound was prepared in 45 mg yield as a brown slightly hygroscopic solid from 4-[4-methyl-5-(3-thienyl)-4H-1,2,4-triazol-3-yl]butanal (54 mg) and (1S,5R)-1-[4-(trifluoromethyl)phenyl]-3-azabicyclo[3.1.0]hexane (53 mg) in analogy to the method described in Example 1.

NMR ($^1$H, DMSO-D6) δ=1.10-1.25 (m, 1H), 1.6-1.95 (m, 5H), 2.22-2.33 (m, 1H), 2.89 (t, 2H), 3.16-3.29 (m, 2H), 3.29-3.84 (m, 3H), 3.74 (s, 3H), 3.96-4.08 (m, 1H), 7.49 (d, 2H), 7.57 (d, 1H), 7.69 (d, 2H), 7.80-7.87 (m, 1H), 8.21 (s, 1H), 10.79 (bs, 1 H). MS (m/z): 447 [MH]+.

Example 37

(1S,5R)-3-{4-[5-(2,4-difluorophenyl)-4-methyl-4H-1,2,4-triazol-3-yl]butyl}-1-[4-(trifluoromethyl)phenyl]-3-azabicyclo[3.1.0]hexane hydrochloride

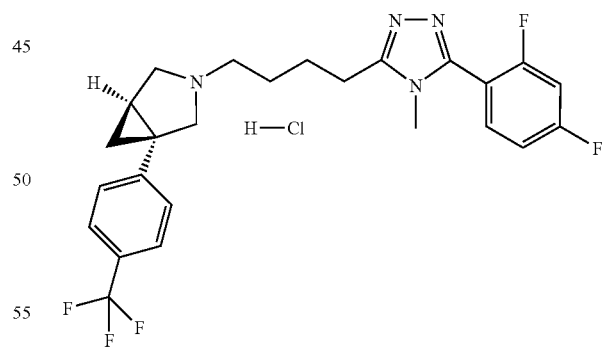

The title compound was prepared in 62 mg yield as a light brown slightly hygroscopic solid from 4-[5-(2,4-difluorophenyl)-4-methyl-4H-1,2,4-triazol-3-yl]butanal (50 mg) and (1S,5R)-1-[4-(trifluoromethyl)phenyl]-3-azabicyclo[3.1.0]hexane (43 mg) in analogy to the method described in Example 1.

NMR ($^1$H, DMSO-D6): δ=1.16-1.27 (m, 1H), 1.65-1.71 (m, 1H), 1.75-1.97 (m, 4H), 2.26-2.34 (m, 1H), 2.81 (t, 2H), 3.15-3.32 (m, 2H), 3.44 (s, 3H), 3.46-3.58 (m, 1H), 3.57-3.67

(m, 1H), 3.74 (d, 1H), 4.04 (d, 1H), 7.30 (dt, 1H), 7.49 (d, 2H), 7.54 (dd, 1H), 7.61-7.69 (m, 1H), 7.71 (d, 2H), 10.37 (bs, 1H). MS (m/z): 477 [MH]+.

Example 38

(1S,5R)-3-{4-[4-methyl-5-(1-methyl-1H-pyrrol-2-yl)-4H-1,2,4-triazol-3-yl]butyl}-1-[4-(trifluoromethyl)phenyl]-3-azabicyclo[3.1.0]hexane hydrochloride

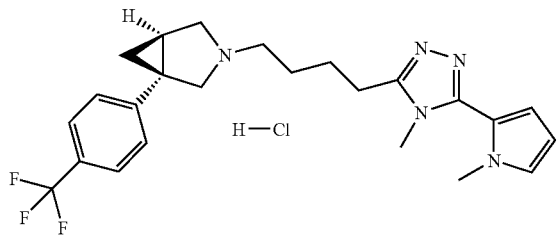

The title compound was prepared in 37 mg yield as a white slightly hygroscopic solid from 4-[4-methyl-5-(1-methyl-1H-pyrrol-2-yl)-4H-1,2,4-triazol-3-yl]butanal (54 mg) and (1S,5R)-1-[4-(trifluoromethyl)phenyl]-3-azabicyclo[3.1.0]hexane (53 mg) in analogy to the method described in Example 1.

NMR (¹H, DMSO-D6) δ=1.16-1.24 (m, 1H), 1.69-1.77 (m, 1H), 1.75-1.94 (m, 4H), 2.25-2.34 (m, 1H), 2.86 (t, 2H), 3.14-3.32 (m, 2H), 3.52-3.67 (m, 2H), 3.60 (s, 3H), 3.66-3.77 (m, 1H), 3.74 (s, 3H), 3.97-4.13 (m, 1H), 6.22 (t, 1H), 6.55 (d, 1H), 7.02-7.08 (m, 1H), 7.49 (d, 2H), 7.70 (d, 2H), 10.53 (bs, 1H). MS (m/z): 444 [MH]+.

Example 39

(1S,5R)-3-{4-[5-(4-fluorophenyl)-4-methyl-4H-1,2,4-triazol-3-yl]butyl}-1-[4-(trifluoromethyl)phenyl]-3-azabicyclo[3.1.0]hexane hydrochloride

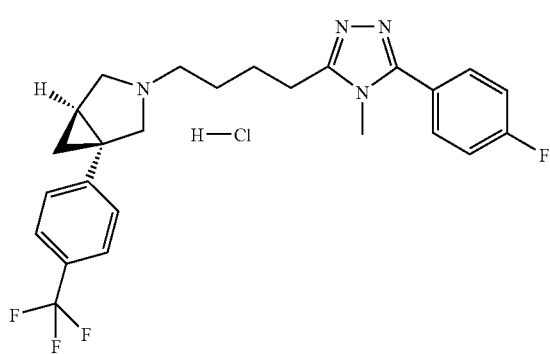

The title compound was prepared in 55 mg yield as a brown slightly hygroscopic solid from 4-[5-(4-fluorophenyl)-4-methyl-4H-1,2,4-triazol-3-yl]butanal (65 mg) and (1S,5R)-1-[4-(trifluoromethyl)phenyl]-3-azabicyclo[3.1.0]hexane (60 mg) in analogy to the method described in Example 1.

NMR (¹H, DMSO-D6): δ=1.15-1.23 (m, 1H), 1.68-1.75 (m, 1H), 1.74-1.91 (m, 4H), 2.25-2.34 (m, 1H), 2.80 (t, 2H), 3.19-3.28 (m, 2H), 3.46-3.57 (m, 1H), 3.57-3.67 (m, 1H), 3.59 (s, 3H), 3.65-3.81 (m, 1H), 3.95-4.10 (m, 1H), 7.40 (t, 2H), 7.49 (d, 2H), 7.64-7.78 (m, 4H), 10.50 (bs, 1H). MS (m/z): 459 [MH]+.

Example 40

(1S,5R)-3-(4-{4-methyl-5-[6-(methyloxy)-3-pyridinyl]-4H-1,2,4-triazol-3-yl}butyl)-1-[4-(trifluoromethyl)phenyl]-3-azabicyclo[3.1.0]hexane hydrochloride

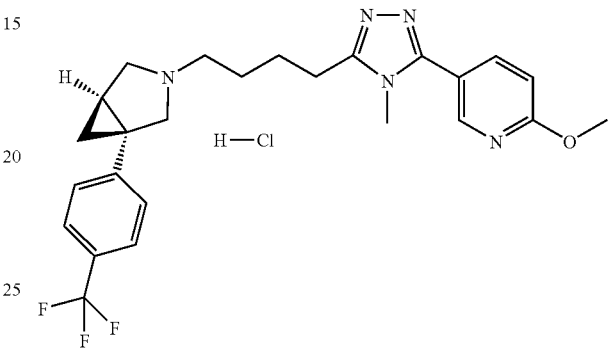

The title compound was prepared in 5 mg yield as a white slightly hygroscopic solid from 4-{4-methyl-5-[6-(methyloxy)-3-pyridinyl]-4H-1,2,4-triazol-3-yl}butanal (37mg) and (1S,5R)-1-[4-(trifluoromethyl)phenyl]-3-azabicyclo[3.1.0]hexane (32 mg) in analogy to the method described in Example 1.

NMR (¹H, DMSO-D6, free base of the title compound): δ=8.41 (s, 1H), 7.88 (d, 1H), 7.55 (d, 2H), 7.23 (d, 2H), 7.89 (d, 1H), 4.02 (s, 3H), 3.62 (s, 3H), 3.40 (d, 1H), 3.15 (d, 1H), 2.82 (t, 2H), 2.68-2.47 (m, 4H), 1.98-1.60 (m, 4H), 1.52 (m, 1H), 0.85 (m, 2H). MS (m/z): 472 [MH]+.

Example 41

(1S,5R)-3-{4-[5-(3,5-difluorophenyl)-4-methyl-4H-1,2,4-triazol-3-yl]butyl}-1-[4-(trifluoromethyl)phenyl]-3-azabicyclo[3.1.0]hexane hydrochloride

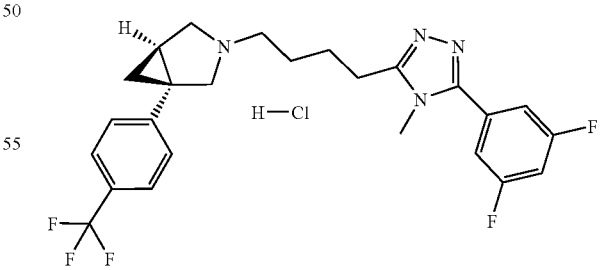

The title compound was prepared in 55 mg yield as a light brown slightly hygroscopic solid from 4-[5-(3,5-difluorophenyl)-4-methyl-4H-1,2,4-triazol-3-yl]butanal (73 mg) and (1S,5R)-1-[4-(trifluoromethyl)phenyl]-3-azabicyclo[3.1.0] hexane (62 mg) in analogy to the method described in Example 1.

NMR (¹H, DMSO-D6): δ=1.16-1.24 (m, 1H), 1.61-1.69 (m, 1H), 1.72-1.93 (m, 4H), 2.25-2.34 (m, 1H), 2.82 (t, 2H), 3.17-3.30 (m, 2H), 3.44-3.56 (m, 1H), 3.59-3.68 (m, 1H), 3.64 (s, 3H), 3.67-3.79 (m, 1H), 3.97-4.15 (m, 1H), 7.40-7.53 (m, 5H), 7.71 (d, 2H), 10.33 (bs, 1H). MS (m/z): 477 [MH]⁺.

Example 42

(1S,5R)-3-{5-[4-methyl-5-(4-methyl-1,3-oxazol-5-yl)-4H-1,2,4-triazol-3-yl]pentyl}-1-[4-(trifluoromethyl)phenyl]-3-azabicyclo[3.1.0]hexane hydrochloride

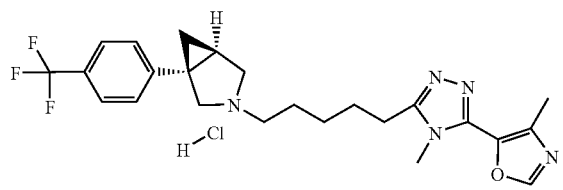

The title compound was prepared in analogy to the method described in Example 14 in 7 mg yield as a white slightly hygroscopic solid from (1S,5R)-1-(4-trifluorophenyl)-3-azabicyclo[3.1.0]hexane (8 mg).

NMR (¹H, CD₃OD) ppm 1.11-1.26 (m, 1 H) 1.35-1.47 (m, 1 H) 1.48-1.62 (m, 2 H) 1.76-1.97 (m, 4 H) 2.25-2.37 (m, 1 H) 2.43 (s, 3 H) 2.91 (t, 2 H) 3.22-3.32 (m, 2 H) 3.54-3.72 (m, 3 H) 3.75 (s, 3 H) 3.83 (d, 1 H) 7.50 (d, 2 H) 7.66 (d, 2 H) 8.35 (s, 1 H). MS (m/z): 460 [MH]⁺.

Example 43

(1S,5R)-3-(5-{4-methyl-5-[3-(methyloxy)phenyl]-4H-1,2,4-triazol-3-yl}pentyl)-1-[4-(trifluoromethyl)phenyl]-3-azabicyclo[3.1.0]hexane hydrochloride

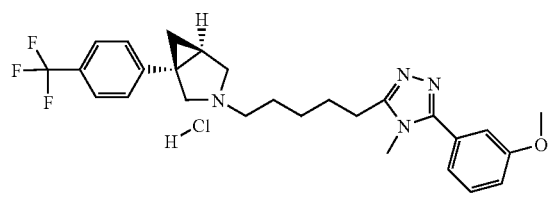

The title compound was prepared in analogy to the method described in Example 14 in 40 mg yield as a white slightly hygroscopic solid from (1S,5R)-1-(4-trifluorophenyl)-3-azabicyclo[3.1.0]hexane (37 mg).

NMR (¹H, DMSO-d₆) ppm 1.16-1.24 (m, 1 H) 1.28-1.37 (m, 1 H) 1.38-1.51 (m, 2 H) 1.74-1.85 (m, 4 H) 2.20-2.33 (m, 1 H) 2.79 (t, 2 H) 3.11-3.25 (m, 2 H) 3.45-3.56 (m, 1 H) 3.59 (s, 3 H) 3.59-3.67 (m, 1 H) 3.67-3.78 (m, 1 H) 3.82 (s, 3 H) 4.08 (d, 1 H) 7.10 (dd, 1 H) 7.19 (d, 1 H) 7.22 (d, 1 H) 7.46-7.53 (m, 3 H) 7.69 (d, 2 H) 10.40 (br. s., 1 H). MS (m/z): 485 [MH]⁺.

Example 44

(1S,5R)-3-{5-[5-(2-chlorophenyl)-4-methyl-4H-1,2,4-triazol-3-yl]pentyl}-1-[4-(trifluoromethyl)phenyl]-3-azabicyclo[3.1.0]hexane hydrochloride

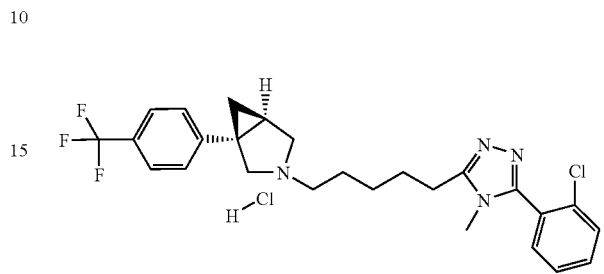

The title compound was prepared in analogy to the method described in Example 14 in 20 mg yield as a white slightly hygroscopic solid from (1S,5R)-1-(4-trifluorophenyl)-3-azabicyclo[3.1.0]hexane (29 mg).

(¹H, DMSO-d₆) ppm 1.33-1.41 (m, 1 H) 1.39-1.48 (m, 1 H) 1.50-1.63 (m, 2 H) 1.79-1.91 (m, 2 H) 1.91-2.01 (m, 2 H) 2.36 (br. s., 1 H) 2.97 (t, 2 H) 3.25-3.37 (m, 2 H) 3.51 (s, 3 H) 3.61-3.67 (m, 1 H) 3.68-3.76 (m, 1 H) 3.78-3.95 (m, 1 H) 4.07-4.22 (m, 1 H) 7.47-7.53 (m, 2 H) 7.54-7.59 (m, 2 H) 7.63-7.71 (m, 4 H) H), acid proton not detected. MS (m/z): 489 [MH]⁺.

Example 45

(1S,5R)-3-{5-[5-(2,4-difluorophenyl)-4-methyl-4H-1,2,4-triazol-3-yl]pentyl}-1-[4-(trifluoromethyl)phenyl]-3-azabicyclo[3.1.0]hexane hydrochloride

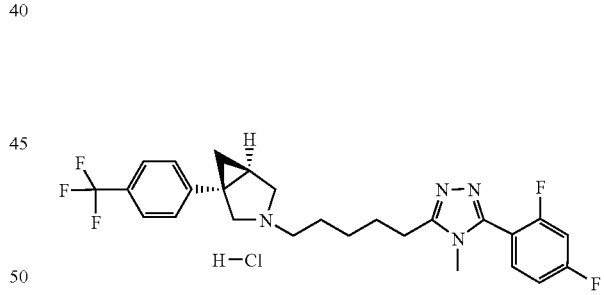

The title compound was prepared in 30 mg yield as a white slightly hygroscopic solid from 4-[5-(2,4-difluorophenyl)-4-methyl-4H-1,2,4-triazol-3-yl]butyl methanesulfonate (95 mg) and (1S,5R)-1-[4-(trifluoromethyl)phenyl]-3-azabicyclo[3.1.0]hexane (43 mg) in analogy to the method described in Example 14, using Na₂CO₃ instead of K₂CO₃.

NMR (¹H, DMSO-d6): δ=1.17-1.27 (m, 1H), 1.44 (t, 2H), 1.59-1.66 (m, 1H), 1.70-1.83 (m, 4H), 2.25-2.33 (m, 1H), 2.79 (t, 2H), 3.12-3.27 (m, 2H), 3.43 (s, 3H), 3.46-3.55 (m, 1H), 3.58-3.67 (m, 1H), 3.66-3.78 (m, 1H), 3.93-4.13 (m, 1H), 7.30 (td, 1H), 7.48 (d, 2H), 7.50-7.57 (m, 1H), 7.60-7.67 (m, 1H), 7.70 (d, 2H), 10.18 (bs, 1H).

MS (m/z): 491 [MH]⁺.

Example 46

(1S,5R)-3-{4-[4-methyl-5-(methylthio)-4H-1,2,4-triazol-3-yl]butyl}-1-[4-(trifluoromethyl)phenyl]-3-azabicyclo[3.1.0]hexane hydrochloride

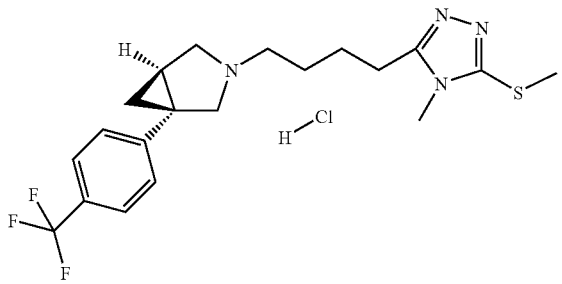

To a stirred solution of (1S,5R)-1-[4-(trifluoromethyl)phenyl]-3-azabicyclo[3.1.0]hexane (40 mg) and 4-[4-methyl-5-(methylthio)-4H-1,2,4-triazol-3-yl]butanal (40 mg) in 1,2-dichloroethane (4 ml) sodium borohydride (76 mg) and acetic acid (20 μl) were added and the reaction mixture was stirred overnight at room temperature. Then an additional amount of 4-[4-methyl-5-(methylthio)-4H-1, 2,4-triazol-3-yl]butanal (48 mg), sodium borohydride (76 mg) and acetic acid (20 μl) were added and the stirring continued for 2 days then DCM and water were added to the reaction mixture. The solvent was removed under reduced pressure affording a crude product that was purified by chromatography to give the free base of the title compound. To a solution of this compound in DCM (1 mL) HCL 1N in diethylehter was added (0.12 mL) and the solvent removed under reduced pressure to give the title compound (67 mg) as a slightly hygroscopic solid.

MS (m/z): 411 [MH]$^+$.

Example 47

(1S,5R)-3-(4-{5-[(cyclopropylmethyl)thio]-4-methyl-4H-1,2,4-triazol-3-yl}butyl)-1-[4-(trifluoromethyl)phenyl]-3-azabicyclo[3.1.0]hexane hydrochloride

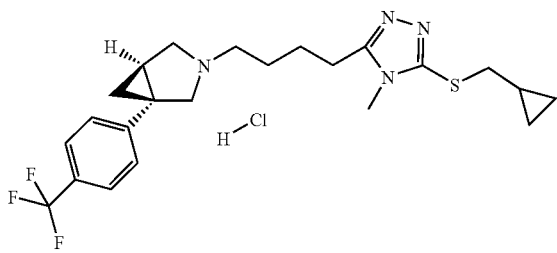

(1S,5R)-1-[4-(trifluoromethyl)phenyl]-3-azabicyclo[3.1.0]hexane (70 mg) and 4-{5-[(cyclopropylmethyl)thio]-4-methyl-4H-1,2,4-triazol-3-yl}butyl methanesulfonate (70 mg) were dissolved in dimethylformamide (0.6 ml). Sodium Iodide (12 mg) and potassium carbonate (35 mg) were added. Reaction was heated at 60° C. for 20 h. Dichloromethane and NaHCO3 saturated solution were added. Solvent was removed, under reduced pressure, from organic phase. Crude was purified by silica column to give the free base of the title compound (5.5 mg). To a solution of this compound in DCM (0.5 mL), HCl 1N in diethylether (0.012 mL) was added and the solvent removed under reduced pressure to give the title compound as a slightly hygroscopic solid. (6.7 mg).

NMR ($^1$H, CD3O): 7.67 (d, 2H), 7.50 (d, 2H), 4.15 (m, 1H), 3.86(m, 1H), 3.73 (s, 3H), 3.67 (m, 2H), 3.37 (m, 2H), 3.24 (d, 2H), 3.04 (m, 2H), 2.33 (m, 1 H), 1.93 (m, 4H), 1.53 (m, 1H), 1.35 (m, 1H), 1.21 (m, 1H), 0.66 (m, 2H), 0.36 (m, 2H).

MS (m/z): 242 [MH]$^+$.

Example 48

(1S,5R)-3-[4-(4-methyl-5-{4-[(trifluoromethyl)oxy]phenyl}-4H-1,2,4-triazol-3-yl)butyl]-1-[4-(trifluoromethyl)phenyl]-3-azabicyclo[3.1.0]hexane hydrochloride

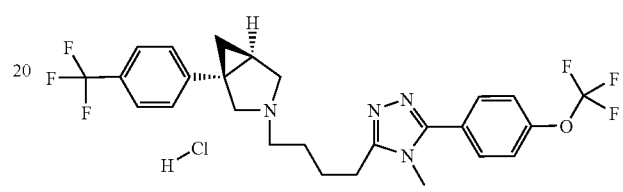

The title compound was prepared in analogy to the method described in Example 1 in 24 mg yield as a white slightly hygroscopic solid from (1S,5R)-1-(4-trifluorophenyl)-3-azabicyclo[3.1.0]hexane (29 mg).

NMR (1H, DMSO-d$_6$) ppm 1.17-1.28 (m, 1 H) 1.56-1.64 (m, 1 H) 1.72-1.92 (m, 4 H) 2.27-2.34 (m, 1 H) 2.83 (t, 2 H) 3.19-3.33 (m, 2 H) 3.45-3.58 (m, 1 H) 3.58-3.67 (m, 1 H) 3.61 (s, 3 H) 3.69-3.79 (m, 1 H) 4.07 (d, 1 H) 7.50 (d, 2 H) 7.56 (d, 2 H) 7.71 (d, 2 H) 7.83 (d, 2 H) 10.15 (br. s., 1 H). MS (m/z): 525 [MH]$^+$.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The invention claimed is:

1. A compound of formula (I) or a pharmaceutically acceptable salt thereof:

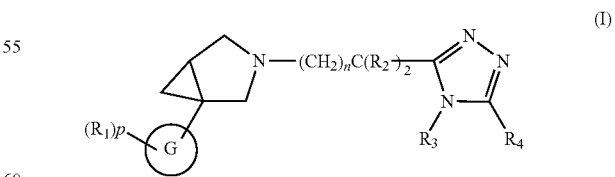

wherein
G is;
p is 0 to 5;
R$_1$ is independently selected from a group consisting of: halogen, hydroxy, cyano, C$_{1-4}$alkyl haloC$_{1-4}$alkyl, C$_{1-4}$alkoxy, haloC$_{1-4}$alkoxy, C$_{1-4}$alkanoyl and SF$_5$;

each R₂ is independently hydrogen, fluorine or $C_{1-4}$alkyl;
n is 2, 3, 4, or 5;
R₃ is $C_{1-4}$alkyl;
R₄ is hydrogen, $C_{1-4}$alkyl, benzyl, phenyl, heterocyclyl, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, halo$C_{1-4}$alkoxy, $C_{1-4}$alkanoyl and $SF_5$; or R₄ is a —SR₆ group;
R₆ is $C_{1-4}$alkyl or —$CH_2C_{3-4}$cycloalkyl;
and when R₁ is chlorine and p is 1, such R₁ is not present in the ortho position with respect to the linking bond to the rest of the molecule; and when R₁ corresponds to R₅, p is 1.

2. A compound as claimed in claim 1 which corresponds to a stereochemical isomer of a compound of formula (I)', enriched in configuration(1S,5R):

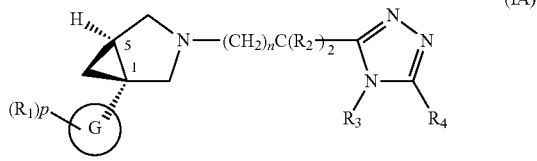

(IA)

wherein G, p, n, R₁, R₂, R₃, R₄, R₅ and R₆ are defined in claim 1.

3. A compound as claimed in claim 1 wherein R₁ is halogen or trifluoromethyl.

4. A compound as claimed in claim 1 wherein R₂ is hydrogen.

5. A compound as claimed in claim 1 wherein both R₂ groups are methyl or fluorine.

6. A compound as claimed in claim 1 wherein n is 3 or 4.

7. A compound as claimed in claim 1 wherein R₄ is optionally substituted phenyl, an optionally substituted quinolinyl, an optionally substituted pyranyl, an optionally substituted pyridinyl, an optionally substituted pyrazolyl, an optionally substituted pyrimidyl, an optionally substituted pyridazinyl, an optionally substituted pyrazinyl, an optionally substituted furanyl, an optionally substituted thienyl, an optionally substituted oxazolyl, an optionally substituted isoxazolyl, an optionally substituted thiazolyl, an optionally substituted triazolyl, an optionally substituted benzyl group, a t-butyl group, a thiomethylcyclopropyl, or a thiomethyl; any of which groups is optional substituted by 1, 2, 3 or 4 substituents selected from the group consisting of: halogen, cyano, $C_{1-4}$alkyl, halo$C_{1-4}$alkyl, $C_{1-4}$alkoxy, halo$C_{1-4}$alkoxy, $C_{1-4}$alkanoyl and $SF_5$.

8. A compound as claimed in claim 1 wherein R₃ is methyl.

9. A compound as claimed in claim 1 which is
(1S,5R)-1-[2-fluoro-4-(trifluoromethyl)phenyl]-3-[4-(4-methyl-5-phenyl-4H-1,2,4-triazol-3-yl)butyl]-3-azabicyclo[3.1.0]hexane;
(1S,5R)-3-[4-(4-methyl-5-phenyl-4H-1,2,4-triazol-3-yl)butyl]-1-[4-(trifluoromethyl)phenyl]-3-azabicyclo[3.1.0]hexane;
(1S,5R)-3-{4-[4-methyl-5-(4-pyridazinyl)-4H-1,2,4-triazol-3-yl]butyl}-1-[4-(trifluoromethyl)phenyl]-3-azabicyclo[3.1.0]hexane;
(1 S,5R)-3-{4-[4-methyl-5-(2-methyl-3-pyridinyl)-4H-1,2,4-triazol-3-yl]butyl}-1-[4-(trifluoromethyl)phenyl]-3-azabicyclo[3.1.0]hexane;
(1S,5R)-3-{4-[4-methyl-5-(6-methyl-3-pyridinyl)-4H-1,2,4-triazol-3-yl]butyl}-1-[4-(trifluoromethyl)phenyl]-3-azabicyclo[3.1.0]hexane;
(1S,5R)-3-{4-[4-methyl-5-(5-methyl-2-pyrazinyl)-4H-1,2,4-triazol-3-yl]butyl}-1-[4-(trifluoromethyl)phenyl]-3-azabicyclo[3.1.0]hexane;
(1S,5R)-3-{4-[5-(2,4-dimethyl-1,3-oxazol-5-yl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(2-methyl-1,3-thiazol-5-yl)-4H-1,2,4-triazol-3-yl]butyl}-1-[4-(trifluoromethyl)phenyl]-3-azabicyclo[3.1.0]hexane;
(1S,5R )-3-{4-[5-(3,4-difluorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(tetrahydro-2H-pyran-4-yl)-4H-1,2,4-triazol-3-yl]butyl}-1-[4-(trifluoromethyl)phenyl]-3-azabicyclo[3.1.0]hexane;
(1S,5R)-3-[5-(4-methyl-5-phenyl-4H-1,2,4-triazol-3-yl)pentyl]-1-[4-(trifluoromethyl)phenyl]-3-azabicyclo[3.1.0]hexane;
(1S,5R)-3-{5-[4-methyl-5-(5-methyl-2-pyrazinyl)-4H-1,2,4-triazol-3-yl]pentyl}-1-[4-(trifluoromethyl)phenyl]-3-azabicyclo[3.1.0]hexane;
(1S,5R)-3-(4-{4-methyl-5-[4-(methyloxy)phenyl]-4H-1,2,4-triazol-3-yl}butyl)-1-[4(trifluoromethyl)phenyl]-3-azabicyclo[3.1.0]hexane;
(1S,5R)-3-{4-[5-(2,4-dichlorophenyl)-4-methyl-4H-1,2,4-triazol-3-yl]butyl}-1-[49-(trifluoromethyl)phenyl]-3-azabicyclo[3.1.0]hexane;
(1S,5R)-3-{4-[5-(3-chlorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[5-(2-fluorophenyl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(4-methyl-1,3-thiazol-5-yl)-4H-1,2,4-triazol-3-yl]butyl}-1-[4(trifluoromethyl)phenyl]-3-azabicyclo[3.1.0]hexane;
(1S,5R)-3-{4-[5-(2,4-dimethyl-1,3-thiazol-5-yl)-4-methyl-4H-1,2,4-triazol-3-yl]butyl}-1-[4-(trifluoromethyl)phenyl]-3-azabicyclo[3.1.0]hexane;
(1S,5R)-3-{4-[4-methyl-5-(phenylmethyl)-4H-1,2,4-triazol-3-yl]butyl}-1-[4-(trifluoromethyl)phenyl]-3-azabicyclo[3.1.0]hexane;
(1S,5R)-3-{4-[5-(1,1-dimethylethyl)-4-methyl-4H-1,2,4-triazol-3-yl]butyl}-1-[4-(trifluoromethyl)phenyl]-3-azabicyclo[3.1.0]hexane;
(1S,5R)-3-{5-[5-(4-chlorophenyl)-4-methyl-4H-1,2,4-triazol-3-yl]pentyl}-1-[4-(trifluoromethyl)phenyl]-3-azabicyclo[3.1.0]hexane;
(1S,5R)-3-(4-{4-methyl-5-[2-methyl-6-(trifluoromethyl)-3-pyridinyl]-4H-1,2,4-triazol-3-yl}butyl)-1-[4-(trifluoromethyl)phenyl]-3-azabicyclo[3.1.0]hexane;
(1S,5R)-3-(4-{4-methyl-5-[3-(methyloxy)phenyl]-4H-1,2,4-triazol-3-yl}butyl)-1-[4-(trifluoromethyl)phenyl]-3-azabicyclo[3.1.0]hexane;
(1S,5R)-3-(4-{4-methyl-5-[2-(methyloxy)phenyl]-4H-1,2,4-triazol-3-yl}butyl)-1-[4-(trifluoromethyl)phenyl]-3-azabicyclo[3.1.0]hexane;
3-[4-methyl-5-(4-{(1S,5R)-1-[4-(trifluoromethyl)phenyl]-3-azabicyclo[3.1.0]hex-3-yl}butyl)-4H-1,2,4-triazol-3-yl]benzonitrile;
2-methyl-5-[4-methyl-5-(4-{(1S,5R)-1-[4-(trifluoromethyl)phenyl]-3-azabicyclo[3.1.0]hex-3-yl}butyl)-4H-1,2,4-triazol-3-yl]quinoline;

(1S,5R)-3-{4-[4-methyl-5-(1,3,5-trimethyl-1H-pyrazol-4-yl)-4H-1,2,4-triazol-3-yl]butyl}-1-[4-(trifluoromethyl)phenyl]-3-azabicyclo[3.1.0]hexane;

4-[4-methyl-5-(4-{(1S,5R)-1-[4-(trifluoromethyl)phenyl]-3-azabicyclo[3.1.0]hex-3-yl}butyl)-4H-1,2,4-triazol-3-yl]benzonitrile;

(1S,5R)-3-[4-methyl-4-(4-methyl-5-phenyl-4H-1,2,4-triazol-3-yl)pentyl]-1-[4-(trifluoromethyl)phenyl]-3-azabicyclo[3.1.0]hexane;

(1S,5R)-3-[4,4-difluoro-4-(4-methyl-5-phenyl-4H-1,2,4-triazol-3-yl)butyl]-1-[4-(trifluoromethyl)phenyl]-3-azabicyclo[3.1.0]hexane;

(1S,5R)-3-{4-[5-(3-fluorophenyl)-4-methyl-4H-1,2,4-triazol-3-yl]butyl}-1-[4-(trifluoromethyl)phenyl]-3-azabicyclo[3.1.0]hexane;

(1S,5R)-3-{4-[5-(2-chlorophenyl)-4-methyl-4H-1,2,4-triazol-3-yl]butyl}-1-[4-(trifluoromethyl)phenyl]-3-azabicyclo[3.1.0]hexane;

(1S,5R)-3-{4-[4-methyl-5-(3-thienyl)-4H-1,2,4-triazol-3-yl]butyl}-1-[4-(trifluoromethyl)phenyl]-3-azabicyclo[3.1.0]hexane;

(1S,5R)-3-{4-[5-(2,4-difluorophenyl)-4-methyl-4H-1,2,4-triazol-3-yl]butyl}-1-[4-(trifluoromethyl)phenyl]-3-azabicyclo[3.1.0]hexane;

(1S,5R)-3-{4-[4-methyl-5-(1-methyl-1H-pyrrol-2-yl)-4H-1,2,4-triazol-3-yl]butyl}-1-[4-(trifluoromethyl)phenyl]-3-azabicyclo[3.1.0]hexane;

(1S,5R)-3-{4-[5-(4-fluorophenyl)-4-methyl-4H-1,2,4-triazol-3-yl]butyl}-1-[4-(trifluoromethyl)phenyl]-3-azabicyclo[3.1.0]hexane;

(1S,5R)-3-(4-{4-methyl-5-[6-(methyloxy)-3-pyridinyl]-4H-1,2,4-triazol-3-yl}butyl)-1-[4-(trifluoromethyl)phenyl]-3-azabicyclo[3.1.0]hexane;

(1S,5R)-3-{4-[5-(3,5-difluorophenyl)-4-methyl-4H-1,2,4-triazol-3-yl]butyl}-1-[4-(trifluoromethyl)phenyl]-3-azabicyclo[3.1.0]hexane;

(1S,5R)-3-{5-[4-methyl-5-(4-methyl-1,3-oxazol-5-yl)-4H-1,2,4-triazol-3-yl]pentyl}-1-[4-(trifluoromethyl)phenyl]-3-azabicyclo[3.1.0]hexane;

(1S,5R)-3-(5-{4-methyl-5-[3-(methyloxy)phenyl]-4H-1,2,4-triazol-3-yl}pentyl)-1-[4-(trifluoromethyl)phenyl]-3-azabicyclo[3.1.0]hexane;

(1S,5R)-3-{5-[5-(2-chlorophenyl)-4-methyl-4H-1,2,4-triazol-3-yl]pentyl}-1-[4-(trifluoromethyl)phenyl]-3-azabicyclo[3.1.0]hexane;

(1S,5R)-3-{5-[5-(2,4-difluorophenyl)-4-methyl-4H-1,2,4-triazol-3-yl]pentyl}-1-[4-(trifluoromethyl)phenyl]-3-azabicyclo[3.1.0]hexane;

(1S,5R)-3-{4-[4-methyl-5-(methylthio)-4H-1,2,4-triazol-3-yl]butyl}-1-[4-(trifluoromethyl)phenyl]-3-azabicyclo[3.1.0]hexane;

(1S,5R)-3-(4-{5-[(cyclopropylmethyl)thio]-4-methyl-4H-1,2,4-triazol-3-yl}butyl)-1-[4-(trifluoromethyl)phenyl]-3-azabicyclo[3.1.0]hexane; or (1S,5R)-3-[4-(4-methyl-5-{4-[(trifluoromethyl)oxy]phenyl}-4H-1,2,4-triazol-3-yl)butyl]-1-[4-(trifluoromethyl)phenyl]-3-azabicyclo[3.1.0]hexane;

or pharmaceutically acceptable salts thereof.

10. A pharmaceutical composition comprising a compound according to claim 1 and a pharmaceutically acceptable carrier.

* * * * *